United States Patent [19]

Klessing et al.

[11] 4,363,805
[45] Dec. 14, 1982

[54] AMINODESOXY-1.4;3.6-DIANHYDROHEXITOL NITRATES AND PHARMACEUTICAL COMPOSITION

[75] Inventors: Klaus Klessing, Ettlingen; Shyam S. Chatterjee; Bernard L. Gabard, both of Karlsruhe, all of Fed. Rep. of Germany

[73] Assignee: Firma Willmar Schwabe, Karlsruhe, Fed. Rep. of Germany

[21] Appl. No.: 285,036

[22] Filed: Jul. 20, 1981

[30] Foreign Application Priority Data

Jul. 25, 1980 [DE] Fed. Rep. of Germany ....... 3028340

[51] Int. Cl.³ .................. A61K 31/34; A61K 31/455; C07D 493/04
[52] U.S. Cl. ................................ 424/230; 260/330.9; 542/421; 542/422; 544/148; 544/377; 546/197; 546/270; 548/526; 549/464; 424/232; 424/248.57; 424/250; 424/266; 424/267; 424/274; 424/285
[58] Field of Search ........... 260/347.3, 347.7, 326.5 C, 260/330.9; 542/421, 422; 544/148, 377; 546/197, 270; 424/230, 232, 248.57, 250, 266, 267, 274, 285; 549/464

[56] References Cited

U.S. PATENT DOCUMENTS 3,886,186  5/1975  Dvonch et al. ................. 260/347.8

Primary Examiner—Richard Raymond
Attorney, Agent, or Firm—Toren, McGeady & Stanger

[57] ABSTRACT

Aminodesoxy-1.4;3.6-dianhydrohexitol nitrates of the general formula I,

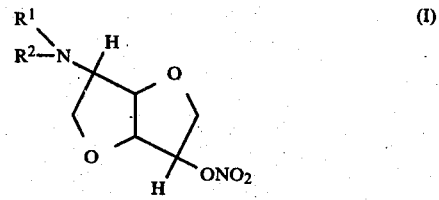

wherein $R^1$ and $R^2$ possess the meanings given in claim 1, as well as their pharmacologically acceptable acid-addition salts; processes for the preparation of said compounds, and pharmaceutical compositions containing at least one of said compounds.

85 Claims, No Drawings

AMINODESOXY-1.4;3.6-DIANHYDROHEXITOL NITRATES AND PHARMACEUTICAL COMPOSITION

BACKGROUND OF THE INVENTION

1. Field of the Invention

The invention concerns aminodesoxy-1.4;3.6-dianhydrohexitol nitrates of the general formula I,

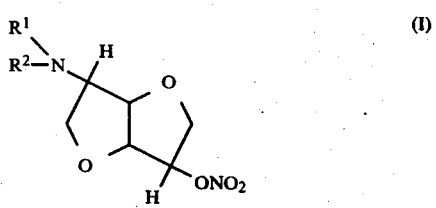

wherein $R^1$ and $R^2$, each independently of one another, signify a hydrogen atom or a lower alkyl group with 1 to 4 C-atoms or wherein $R^1$ signifies a hydrogen atom or a lower alkyl group with 1 to 4 C-atoms and $R^2$ an acyl radical of an aliphatic or singly unsaturated, possibly methyl-substituted monocarboxylic acid with 2 to 8 C-atoms, a nicotinoyl, 2-O-acetylsalicoyl radical or a 1-adamantyl radical, or wherein $R^1$ signifies a hydrogen atom and $R^2$ a 2-hydroxy-3-(subst.)-phenoxyprop-1-yl radical of the general formula Ia

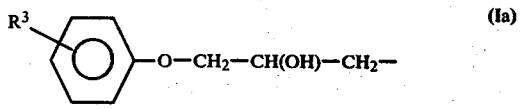

wherein $R^3$ signifies a hydrogen atom, a lower alkyl or lower alkenyl group with 1 to 4 C-atoms, the trifluoromethyl radical, a hydroxyl group, a lower alkoxy or lower alkenyloxy group with 1 to 4 C-atoms, a cyano group or a carbamoylmethyl radical, or wherein $R^1$ signifies a hydrogen atom and $R^2$ a 2-hydroxy-3-(α-naphthyloxy)-prop-1-yl radical, whereby the ring of the naphthalene structure not etherified with the hydroxypropyl group can be wholly or partially hydrogenated or substituted by an oxo group, or wherein $R^1$ signifies a hydrogen atom or a lower alkyl group with 1 to 4 C-atoms and $R^2$ an ω-(subst.)-phenylalkyl group of the general formula Ib

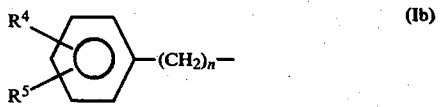

wherein n can be = a whole number from 1-6 and $R^4$ and $R^5$, each independently of one another, signify a hydrogen atom, a lower alkyl or alkenyl group with 1 to 4 C-atoms, the trifluoromethyl radical, a hydroxyl group, a lower alkoxy or lower alkenyloxy group with 1 to 4 C-atoms or a fluorine or chlorine atom, or wherein $R^1$ signifies a hydrogen atom or a lower alkyl group with 1 to 4C-atoms and $R^2$ the diphenylmethyl radical or cinnamyl radical, or wherein $R^1$ signifies a hydrogen atom or a lower alkyl group with 1 to 4 C-atoms and $R^2$ an ω-(subst.)-phenoxyalkyl group of the general formula Ic

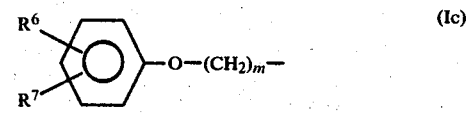

wherein m can be = a whole number of 2-8 and $R^6$ and $R^7$, independently of one another, a hydrogen atom, a lower alkyl or lower alkenyl group with 1 to 4 C-atoms, the trifluoromethyl radical, a hydroxyl group, a lower alkoxy or lower alkenyloxy group with 1 to 4 C-atoms, a fluorine or chlorine atom, the amino or acetylamino group, a mono- or di-lower alkylamino group with 1 to 4 C-atoms or $R^6$ and $R^7$, together with the phenyl radical, form the α-naphthyl radical, or wherein $R^1$ and $R^2$, together with the nitrogen atom to which they are attached, represent the radical of a cyclic, non-aromatic, secondary amine with 5 to 7 ring atoms, possibly containing a further hetero atom, or wherein $R^1$ and $R^2$ together signify the pyridoxylidene radical, as well as their pharmacologically acceptable acid-addition salts.

The basic structure of these compounds consists of one of the stereoisomeric 1.4;3.6-dianhydrohexitols, convertible into one another by epimerisation, namely, either 1.4:3.6-dianhydro-L-iditol (="isoidide") (II),

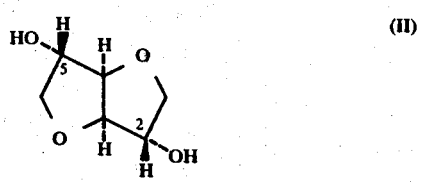

in which the OH groups in the 2- and 5-position each have the exo-configuration, or 1.4;3.6-dianhydro-D-glucitol (="isosorbide") (III)

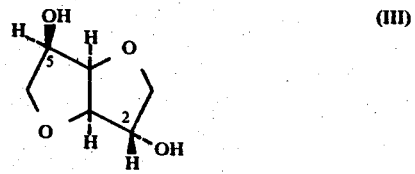

which has a 2-exo-standing and a 5-endo-standing OH group and thus—in the case of different substituents in the 2- and 5-position—occurs in two isomeric forms.

Finally, the basic structure of some compounds consists of 1.4;3.6-dianhydro-D-mannitol (="isomannide") (IV),

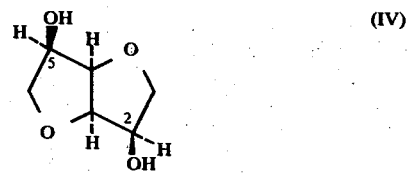

which has two endo-standing OH groups.

Since, in contradistinction to the glucitol derivatives, in the case of the iditol and mannitol derivatives a difference between the 2- and 5-substituents is not possible because the $C^2$-atom, in the case of rotation of the molecule through 180°, becomes the $C^5$-atom, references to the 5-position or 2-position of substituents are superfluous in the case of these compounds. However, for a better comparison of the structures of the individual compounds with the general formulae, the isoidide derivatives are here always referred to as 5-aminoisoidide derivatives since they result from the isosorbide derivatives acyl-substituted in the 5-position. Correspondingly, the isomannide acyl derivatives employed as starting compounds are referred to as 2-acylisomannide derivatives since they are prepared from isosorbide derivatives substituted in the 2-position.

2. Description of the Prior Art

A brief summary regarding the stereoisomerism of the 1.4;3.6-dianhydrohexitols is given by J. A. Mills in Advances in Carbohydrate Chem., 10, 1-53 (1955).

The invention also concerns processes for the preparation of the initially-mentioned aminodesoxy-1.4;3.6-dianhydrohexitol nitrates, as well as pharmaceutical compositions which contain the compounds according to the invention.

The nitrates of 1.4;3.6-dianhydro-D-glucitol (also called 1.4;3.6-dianhydro-D-sorbitol) are known e.g. from U.S. patent specification No. 3,886,186, namely, not only the 2- and 5-mononitrates but also the 2,5-dinitrates of isosorbide. These nitrates, especially the dinitrate, which are already commercially available as medicaments, are pharmacologically active substances with haemodynamic, vasodilatory and antianginous effectiveness which are especially employed in the case of coronary insufficiency and for the treatment of angina pectoris.

The pharmacokinetics of the dinitrate and of the mononitrates of isosorbide, isomannide and isoidide have been described by Bogaert and Rosseel in Naunyn-Schmiedeberg's Arch. Pharmacol., 275, 339 (1972).

However, it has been shown that the nitrates cause unpleasant side effects, especially headaches. Furthermore, the mononitrates are more poorly resorbed than, for example, isosorbide dinitrate (ISDN). It is also to be added that the dinitrates of isosorbide, isomannide and isoidide can only be prepared and handled with special precautionary measures because they are explosive.

SUMMARY OF THE INVENTION

Thus, a need existed for the making available of new pharmaceutical agents with the same activity spectrum but which do not display the mentioned disadvantages and for the provision of new 1.4;3.6-dianhydrohexitol mononitrates which can be used as effective components of such pharmaceutical agents.

The task forming the basis of the invention consists in satisfying the stated need, the solution of this problem in the making available of the materials according to the invention.

Consequently, the subject of the invention are

1. N-substituted 5-amino-5-desoxy-1.4;3.6-dianhydro-L-iditol 2-nitrates, as well as the N-unsubstituted 5-amino-5-desoxy-1.4;3.6-dianhydro-L-iditol 2-nitrate of the general formula V,

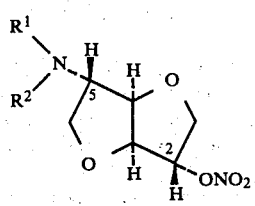

(V)

wherein $R^1$ and $R^2$ possess the meanings mentioned in claim 1, as well as their physiologically acceptable acid-addition salts;

2. the correspondingly N-substituted 5-amino-5-desoxy-1.4;3.6-dianhydro-D-glucitol 2-nitrates, as well as the N-unsubstituted 5-amino-5-desoxy-1.4;3.6-dianhydro-D-glucitol 2-nitrate of the general formula VI,

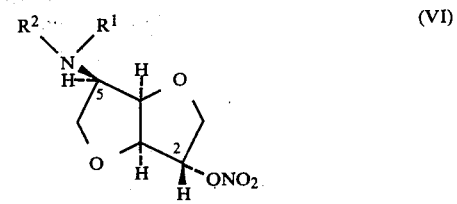

(VI)

as well as their physiologically acceptable acid-addition salts;

3. the correspondingly N-substituted 2-amino-2-desoxy-1.4;3.6-dianhydro-D-glucitol 5-nitrates and the N-unsubstituted 2-amino-2-desoxy-1.4;3.6-dianhydro-D-glucitol 5-nitrate of the general formula VII,

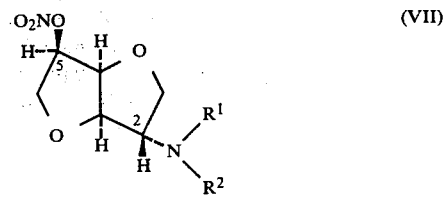

(VII)

as well as their physiologically acceptable acid-addition salts;

4. the correspondingly N-substituted 5-amino-5-desoxy-1.4;3.6-dianhydro-D-mannitol 2-nitrates and the N-unsubstituted 5-amino-5-desoxy-1.4;3.6-dianhydro-D-mannitol 2-nitrate of the general formula VIII,

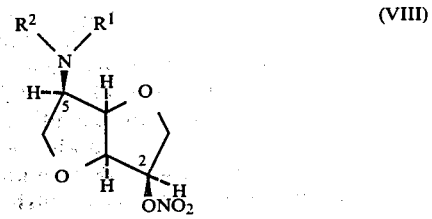

(VIII)

as well as their physiologically acceptable acid-addition salts.

The compounds according to the invention possess coronary flowthrough-increasing, spasmolytic, blood pressure-lowering, negatively inotropic and heart frequency-lowering effectiveness. They are suitable for the treatment of coronary diseases, for the treatment and prophylaxis of angina pectoris attacks, for the post-treatment of heart infarcts and for the treatment of heart insufficiencies. The new compounds possess a good therapeutic range. The oral absorption is especially good and the period of action long. Furthermore, they bring about an improvement of the peripheral blood flow and of the brain blood flow.

The handling and preparation of the compounds according to the invention is much less dangerous than, for example, in the case of the known ISDN, because they are not explosive.

The compounds according to the invention possess four asymmetric C-atoms in the 1.4;3.6-dianhydrohexitol basic structure and are present in optically-active form since optically pure 1.4;3.6-dianhydrohexitols are used as starting compounds, which are easily obtainable from naturally-occurring sugar alcohols.

The compounds according to the invention can be prepared starting from the epimeric unsubstituted 1.4;3.6-dianhydrohexitols, thus starting from L-isoidide, D-isosorbide and D-isomannide, whereby, in the case of D-isosorbide as starting compound, several different synthesis routes are possible.

According to the invention, one of these routes consists in that the corresponding 1.4;3.6-dianhydrohexitol is converted with a sulphonic acid chloride, especially with methanesulphonic acid chloride or toluenesulphonic acid chloride, in a suitable anhydrous solvent and in the presence of an adjuvant base, preferably in pyridine or in chloroform/triethylamine, at a reduced temperature, preferably between −20° and +10° C., into the corresponding mono-O-acyl-1.4;3.6-dianhydrohexitol which is then, by the addition of an aqueous, for example 25%, ammonia solution or by the addition of a primary or secondary alkylamine with 1 to 4 C-atoms or of a primary amine, such as, for example, 1-aminoadamantane, or of a cyclic, non-aromatic secondary amine, subjected to an ammonolysis or aminolysis namely, advantageously under elevated pressure, preferably at a pressure of 2–20 ats., and elevated temperature, preferably at 90° to 180° C. The ammonolysis or aminolysis is expediently carried out in a closed steel autoclave, possibly with the addition of a suitable solvent, such as e.g. ethanol, butanol or dioxan, up to quantitative reaction.

DESCRIPTION OF THE PREFERRED EMBODIMENT

In the case of the ammonlysis or aminolysis to the corresponding possibly N-substituted aminodesoxy-1.4;3.6-dianhydrohexitol, the mesylate or tosylate group is exchanged for the amino or the correspondingly substituted amino group according to the reaction mechanism of a typical bimolecular nucleophilic substitution ($S_N 2$ reaction), which always involves a reversal of configuration on the central carbon atom. This reversal of configuration, which is also known to the expert by the terms "inversion" or "Walden inversion", is the reason why, from the 1.4;3.6-dianhydro-D-glucitol 5-acyl derivative, in which the acyl radical is present endo-standing in the 5-position, there is always formed the 1.4;3.6-dianhydro-L-iditol derivative substituted in the 5-position by the amino group or the corresponding substituted amino group, in which the substituent entering into the molecule in place of the acyl radical no longer stands in the endo- but rather in the exo-position. The Walden inversion involved in the $S_N 2$ reaction is, in a completely corresponding manner, responsible for the fact that from the corresponding iditol acylate there is always formed the glucitol derivative endo-substituted in the 5-position, from the mannitol acylate the corresponding glucitol derivative exo-substituted in the 2-position and from the glucitol 2-exo-acylate, the corresponding mannitol derivative endo-substituted in the 2-position.

The possibly N-substituted aminodesoxy-1.4;3.6-dianhydrohexitols resulting in the course of the hitherto described first synthesis route have a free hydroxyl group in the 2- or 5-position of the 1.4;3.6-dianhydrohexitols. This free hydroxyl group is esterified with nitric acid, nitrating acid or with a mixture of nitric acid and glacial acetic acid/acetic anhydride in the presence of urea at a reduced temperature, preferably at −20° to 0° C., to give the corresponding aminodesoxy-1.4;3.6-dianhydrohexitol mononitrate, whereby, instead of the aminodesoxy-1.4;3.6-dianhydrohexitol in the form of the free base, a suitable acid-addition salt, for example the corresponding salt of methanesulphonic acid, nitric acid or sulphuric acid, can also be used for the esterification.

The so formed mononitrate can, in the case of the N-unsubstituted or N-monoalkyl-substituted aminodesoxy-1.4;3.6-dianhydrohexitol nitrate, subsequently be condensed in per se known manner with an acid chloride, with pyridoxal, with benzyl chloride or a suitable possibly phenyl-substituted phenylalkyl halide or phenylalkylmethanesulphonate, with a possibly phenyl-substituted 1,2-epoxy-ω-phenoxyalkane or with a possibly phenyl-substituted 1-halo- or 1-methanesulphonyloxy-ω-phenoxyalkane to give the desired compound according to the invention, preferably with the addition of a suitable solvent and possibly of an adjuvant base or in the presence of an excess of the corresponding aminodesoxy-1.4;3.6-dianhydrohexitol nitrate.

For the preparation of those compounds according to the invention of general formula I, wherein $R^1$ signifies hydrogen and $R^2$ a lower alkyl group with 1 to 4 C-atoms or the 1-adamantyl radical, the corresponding 1.4;3.6-dianhydrohexitol acylate, e.g. 1.4;3.6-dianhydro-D-glucitol 2- or 5-methanesulphonate, 1.4;3.6-dianhydro-D-mannitol 2-methanesulphonate or 1.4;3.6-dianhydro-L-iditol 5-methanesulphonate, is subjected to the aminolysis with primary or secondary alkylamines with 1 to 4 C-atoms or with 1-aminoadamantane, namely, preferably under elevated pressure, preferably at a pressure of 2–20 ats., and elevated temperature, preferably at 90° to 180° C., and possibly in the presence of a solvent, preferably of ethanol, butanol, dioxan or glycol diethers. The aminolysis is expediently carried out in a closed steel autoclave up to quantitative reaction.

The aminolysis takes place with reversal of configuration of the substituted carbon atom so that, for example, from the 1.4;3.6-dianhydro-D-glucitol 2-methanesulphonate there results the N-mono- or -dialkyl- substituted 2-amino-2-desoxy-1.4;3.6-dianhydro-D-mannitol, from the 1.4;3.6-dianhydro-D-glucitol 5-methanesulphonate the corresponding N-substituted 5-amino-5-desoxy-1.4;3.6-dianhydro-L-iditol, from the 1.4;3.6-dianhydro-D-mannitol 2-methanesulphonate the 2-amino-2-desoxy-1.4;3.6-dianhydro-D-glucitol derivative and from the 1.4;3.6-dianhydro-L-iditol 5-methanesulphonate the 5-amino-5-desoxy-1.4;3.6-dianhydro-D-glucitol derivative.

As primary or secondary amines, there can be used e.g. methylamine, ethylamine, propylamine, isopropylamine, butylamine, isobutylamine, tert.-butylamine, dimethylamine, diethylamine, dipropylamine, dibutylamine, methylethylamine, methylpropylamine etc.

Subsequent to the aminolysis, the free hydroxyl group of the corresponding N-mono- or N-disubstituted aminodesoxy-1.4;3.6-dianhydrohexitol is esterified in the previously described per se known manner with nitric acid.

For the preparation of those compounds according to the invention of general formula I, wherein $R^1$ and $R^2$, together with the nitrogen atom to which they are attached, represent the radical of a cyclic, non-aromatic secondary amine with 5 to 7 ring atoms and possibly containing a further hetero atom, the corresponding 1.4;3.6-dianhydrohexitol acylate—also with reversal of configuration—is subjected to the aminolysis with secondary cyclic non-aromatic amines, for example, with pyrrolidine, piperidine, hexamethyleneimine, morpholine, 4-methylpiperazine etc., whereby the reaction is advantageously carried out, as described above, under elevated pressure and elevated temperature in a steel autoclave. The so prepared cyclic aminodesoxy-1.4;3.6-dianhydrohexitol derivatives are subsequently esterified on their free hydroxyl group with nitric acid completely analogously to the previously described manner.

For the preparation of those compounds according to the invention of general formula I, wherein $R^1$ signifies a hydrogen atom or a lower alkyl group and $R^2$ an acyl radical of an aliphatic or singly unsaturated, possibly methyl-substituted monocarboxylic acid, a nicotinoyl or 2-O-acetylsalicoyl radical, one reacts the corresponding, possibly N-alkyl-substituted amino-isohexide nitrate with, for example, acetyl chloride, propionyl chloride, butyryl chloride, n-valeroyl chloride, isovaleroyl chloride, caproyl chloride, pivaloyl chloride, nicotinic acid chloride hydrochloride or O-acetylsalicyclic acid chloride.

For the preparation of those compounds according to the invention of general formula I, wherein $R^1$ signifies a hydrogen atom or a lower alkyl group and $R^2$ the diphenylmethyl radical, the cinnamyl radical or an ω-(subst.)-phenylalkyl radical of the general formula Ib, the corresponding possibly N-alkyl-substituted aminoisohexide nitrate is reacted with compounds such as e.g. bromodiphenylmethane, cinnamyl bromide, benzyl chloride, phenylethyl bromide, phenylpropyl bromide, phenylbutyl bromide, phenylpentyl bromide, 3-(3,4-dimethoxyphenyl)-propyl 1-methanesulphonate, 4-(4-methoxyphenyl)-butyl-1-methanesulphonate, 4-(4-chlorophenyl)-butyl 1-methanesulphonate or 3-(4-chlorophenyl)-propyl 1-methanesulphonate etc.

For the preparation of those compounds according to the invention of general formula I, wherein $R^1$ signifies a hydrogen atom or a lower alkyl group and $R^2$ an ω-phenoxyalkyl group, the corresponding possibly N-alkyl-substituted aminoisohexide nitrate is reacted with compounds such as e.g. 2-phenoxy-1-bromoethane, 3-phenoxy-1-bromopropane, 4-phenoxy-1-bromobutane, 5-phenoxy-1-bromopentane, 6-phenoxy-1-bromohexane, 7-phenoxy-1-bromoheptane, 8-phenoxy-1-bromooctane.

For the preparation of those compounds according to the invention of general formula I, wherein $R^1$ signifies a hydrogen atom and $R^2$ a 2-hydroxy-3-(subst.)-phenoxyprop-1-yl radical of general formula Ia or a 2-hydroxy-3-(subst.)-naphthyloxyprop-1-yl radical, the corresponding aminoisohexide nitrate is reacted in per se known manner with compounds such as 1,2-epoxy-3-(4-methoxyphenoxy)-propane, 1,2-epoxy-3-(3-methoxyphenoxy)-propane, 1,2-epoxy-3-(2-methoxyphenoxy)-propane, 1,2-epoxy-3-(2-ethoxyphenoxy)-propane, 1,2-epoxy-3-(2-allyloxyphenoxy)-propane, 1,2-epoxy-3-(2-allylphenoxy)-propane, 1,2-epoxy-3-(2-cyanophenoxy)-propane, 1,2-epoxy-3-(3-tolyloxy)-propane, 1,2-epoxy-3-(3-trifluoromethylphenoxy)-propane, 4-(2,3-epoxypropoxy)-phenylacetic acid amide, 1,2-epoxy-3-(1-naphthyloxy)-propane, 5-(2,3-epoxypropoxy)-1-tetralone, 5-(2,3-epoxypropoxy)-tetralin.

For the preparation of those compounds according to the invention of general formula I, wherein $R^1$ signifies a hydrogen atom or a lower alkyl group and $R^2$ an ω-phenoxy-alkyl group of general formula Ic with substituted phenyl radical or an ω-naphthyloxyalkyl group, the corresponding possibly N-lower-alkyl-substituted aminoisohexide nitrate is reacted with compounds such as 3-(3-trifluoromethylphenoxy)-1-bromopropane, 3-(4-tolyloxy)-1-bromopropane, 3-(4-fluorophenoxy)-1-bromopropane, 3-(1-naphthyloxy)-1-bromopropane, 3-(4-methoxyphenoxy)-1-bromopropane, 3-(3-methoxyphenoxy)-1-bromopropane, 3-(2-methoxyphenoxy)-1-bromopropane, 3-(2,6-dimethoxyphenoxy)-1-bromopropane, 3-(3,5-dimethoxyphenoxy)-1-bromopropane, 3-(2,3-dimethoxyphenoxy)-1-bromopropane, 3-(4-chlorophenoxy)-1-bromopropane, 3-(2-chlorophenoxy)-1-bromopropane, 3-(3-chlorophenoxy)-propyl 1-methanesulphonate, 3-(3,4-dichlorophenoxy)-propyl 1-methanesulphonate, 3-(2,4-dichlorophenoxy)-propyl 1-methanesulphonate, 3-(4-acetamidophenoxy)-1-bromopropane, 3-(3-dimethylaminophenoxy)-propyl 1-methanesulphonate.

For the preparation of those compounds according to the invention of general formula I, wherein $R^1$ and $R^2$ together signify the pyridoxylidene radical, one condenses the corresponding aminodesoxy-1.4;3.6-dianhydrohexitol nitrate with pyridoxal, namely, advantageously in a suitable solvent or solvent mixture, e.g. ethanol, benzene, toluene or a mixture of these solvents, so that the resultant water of reaction can easily be removed by azeotropic distillation and an almost quantitative reaction can be achieved.

As follows from the above description of the process according to the invention for the preparation of the compounds according to the invention of general formula I, for the preparation of 5-amino-5-desoxy-1.4;3.6-dianhydro-L-iditol 2-nitrate, as well as of its N-mono- and N-disubstituted derivatives of the general formula V, as substrate of the ammonlysis or aminolysis, one must always employ the corresponding 1.4;3.6-dianhydro-D-glucitol 5-acylate, for example the 5-methanesulphonate or 5-toluenesulphonate, whereas for the preparation of 5-amino-5-desoxy-1.4;3.6-dianhydro-D-glucitol 2-nitrate as well as of its N-mono- and N-disubstituted derivatives of the general formula VI, one must always employ, as substrate for the ammonolysis or aminolysis, the corresponding 1.4;3.6-dianhydro-L-iditol 5-acylate, for example the 5-methanesulphonate or 5-toluenesulphonate.

Completely analogously, for the preparation of 2-amino-2-desoxy-1.4;3.6-dianhydro-D-glucitol 5-nitrate, as well as of its N-mono- and N-disubstituted derivatives of general formula VII, as substrate for the ammonolysis or aminolysis, one must always employ the corresponding 1.4;3.6-dianhydro-D-mannitol 2-acylate, for example the 2-methanesulphonate or 2-toluenesulphonate, whereas for the preparation of 5-amino-5-desoxy-1.4;3.6-dianhydro-D-mannitol 2-nitrate, as well as of its N-mono- and N-disubstituted derivatives of the general formula VIII, as substrate for the ammonolysis or aminolysis, one must use the corresponding 1.4;3.6-dianhydro-D-glucitol 2-acylate, for example the 2-methanesulphonate or 2-toluenesulphonate, whereafter, in the previously described manner, there follows the esterification with nitric acid and thereafter possibly the desired further substitution of the amino nitrogen by acylation with the corresponding acid chlorides or the further condensation with the corresponding reactive arylalkyl, aryloxyalkyl or aryloxy-epoxypropyl derivatives or with pyridoxal.

The previously described first route according to the invention for the preparation of the compounds according to the invention, in which the corresponding isohexide is converted with a sulphonic acid chloride, preferably with methanesulphonic acid chloride or toluenesulphonic acid chloride, into the corresponding monoacyl-1.4;3.6-dianhydrohexitol, has the disadvantage that, in the case of the acylation, not only does the corresponding 5-O-acyl derivative or 2-O-acyl derivative arise but simultaneously also the 2,5-diacyl derivative so that, in the case of the isoidide and isomannide derivatives, in each case the monoacyl compound must be separated from the diacylate, whereas in the case of the isosorbide, in which two stereoisometric monoacyl derivatives are formed besides the diacylate, the desired acylate must be isolated from the mixture of the three acyl derivatives. The separation of the acylate mixture takes place either by fractional crystallisation, fractional extraction or with the help of other per se known methods.

The laborious and time-consuming separation of the acylate mixture disappears, however, in the case of the use of the second synthesis route according to the invention to give the 5-aminoisoidide derivatives in that 1.4;3.6-dianhydro-D-glucitol is reacted quantitatively with an excess of sulphonic acid chloride, preferably methanesulphonyl chloride or toluenesulphonyl chloride, in pyridine or chloroform/triethylamine, to give the corresponding 1.4;3.6-dianhydro-D-glucitol 2,5-diacylate.

The diacylate is then subjected, under appropriate conditions, as described in the case of the first synthesis route, to the ammonolysis or aminolysis, whereby, as a result of the preferred substitution of the 5-endo-acyl group, with reversal of configuration, and as a result of partial hydrolysis of the 2-exo-acyl group, with maintenance of the configuration, besides a small amount of 2,5-diamino-2,5-didesoxy-1.4;3.6-dianhydro-D-glucitol remaining in the aqueous phase, there results a mixture of 5-amino-5-desoxy-1.4;3.6-dianhydro-L-iditol and 5-amino-5-desoxy-1.4;3.6-dianhydro-L-iditol 2-methanesulphonate in a ratio of about 1:4.

For the completion of the hydrolysis of the 2-exo-acyl group, this 1:4 mixture is then subjected to an alkaline or acidic hydrolysis and the resultant 5-amino-5-desoxy-1.4;3.6-dianhydro-L-iditol is subsequently, as described in the case of the first synthesis route, esterified to the corresponding mononitrate and possibly—completely analogously—by condensation with the corresponding acyl chlorides, ω-(subst.)-arylalkyl halides or methanesulphonates, ω-(subst.)-aryloxyalkyl halides or methanesulphonates, 1,2-epoxy-3-(subst.)-aryloxypropanes or with pyridoxal, converted into the compounds of general formula V, wherein $R^1$ signifies a hydrogen atom and $R^2$ possesses one of the given meanings or in which $R^1$ and $R^2$ together represent a pyridoxylidene radical.

As follows from the fact that the ammonolysis of isosorbide 2,5-diacylate preponderantly leads to the 5-aminoisoidide 2-acylate, the nucleophilic substitution of the 2-exo-acylate group in the isosorbide diacylate is sterically hindered. The degree of steric hindrance is temperature dependent. In order to obtain the 5-amino-2-acylate as quantitatively as possible from the corresponding diacylate, one works, therefore, preferably at a temperature of 80° to 120° C. since at temperatures above 120° C. the 2-exo-group, even if only to a small extent, is also attacked by ammonia or by mono- or dialkylamine used instead of ammonia. As solubiliser, an alcohol, preferably ethanol, can be added to the aqueous ammonia solution or to the mono- or dialkylamine.

For the preparation of those compounds according to the invention of general formula V, wherein $R^1$ and/or $R^2$ signify a lower alkyl group with 1 to 4 C-atoms, the 1.4;3.6-dianhydro-D-gluctiol 2,5-diacylate is subjected to the aminolysis with primary or secondary alkylamines with 1 to 4 C-atoms, namely, advantageously under elevated pressure, preferably at a pressure of 2 to 20 ats., and elevated temperature, preferably at 90° to 180° C. The aminolysis is, completely analogously to the above-described ammonolysis, expediently carried out in a closed steel autoclave up to quantitative reaction. Subsequently, the hydrolysis is carried out in the previously described manner, followed by the esterification of the 2-hydroxy group with nitric acid.

The aminolysis can be carried out not only with methylamine, ethylamine, propylamine, butylamine, dimethylamine, diethylamine, dipropylamine, dibutylamine etc. but also, for example, with 1-aminoadamantane, as well as cyclic, non-aromatic secondary amines, such as pyrrolidine, piperidine, morpholine, 4-methylpiperazine and the like heterocyclic nitrogen bases and then leads to the compounds according to the invention of general formula V, wherein $R^1$ and $R^2$, together with the nitrogen atom to which they are attached, signify the residue of a cyclic, non-aromatic secondary amine possibly containing a further hetero atom.

For the preparation of those compounds of general formula V, wherein $R^1$ signifies a lower alkyl group with 1 to 4 C-atoms and $R^2$ an acyl radical, an ω-(subst.)-arylalkyl or -alkenyl radical, an ω-(subst.)-aryloxyalkyl radical or a 2-hydroxy-3-(subst.)-aryloxyprop-1-yl radical, the 5-lower alkylamino-5-desoxy-1.4;3.6-dianhydro-L-iditol 2-nitrates formed in the case of the aminolysis of isosorbide 2,5-diacylate with primary amines and subsequent alkaline hydrolysis and esterification with nitric acid are condensed completely analogously to the previously described manner, namely, with the corresponding acyl halides, ω-(subst.)-arylalkyl or -alkenyl halides or methanesulphonates, ω-(subst.)-aryloxyalkyl halides or methanesulphonates or with the 1,2-epoxy-3-(subst.)-arylpropanes.

In the case of a further route according to the invention for the preparation of the compounds according to the invention of general formula VI, one makes use of the surprisingly found fact that 1.4;3.6-dianhydro-D-glucitol 2,5-diacylates (dimesylate or ditosylate) are selectively attacked on the $C^5$-atom by sodium benzoate in a suitable solvent, preferably in a dipolar aprotic solvent, for example in anhydrous dimethylformamide, dimethyl sulphoxide or diethers of ethylene glycol, at temperatures of 100° to 180° C., preferably 120° to 150° C., so that, with reversal of configuration, 1.4;3.6-dianhydro-L-iditol 2-methanesulphonate 5-benzoate or 1.4;3.6-dianhydro-L-iditol 2-toluenesulphonate 5-benzoate result in high yield. This product is now again subjected to the ammonolysis with 25% ammonia solution or to aminolysis under elevated pressure and elevated temperature, whereby the benzoic acid ester is not split off with substitution but rather hydrolytically, namely, with maintenance of the configuration on the $C^5$-atom, whereas the acylate radical on the $C^2$-atom is substituted, with reversal of configuration, by the amino or alkylamino group to give the corresponding 5-amino-5-desoxy-1.4;3.6-dianhydro-D-glucitol or 5-alkylamino-5-desoxy-1.4;3.6-dianhydro-D-glucitol.

Since the last-mentioned elegant process involves a double selective reversal of configuration, the configuration of the end product is, with regard to its substituents, identical with the configuration of the starting compound; from the isosorbide disulphonate there again results an isosorbide derivative, namely, 5-amino- or 5-alkylamino-5-desoxy-1.4;3.6-dianhydro-D-glucitol, which then, as previously described, can be further worked up to give the desired compounds of general formula VI.

In order to convert the compounds according to the invention into their physiologically acceptable salts, there can be used inorganic acids and mineral acids, such as hydrohalic acids and phosphoric acids, as well as organic acids, such as carboxylic and sulphonic acids, for example malonic, succinic, lactic, tartaric, malic, benzoic, salicylic, citric, ascorbic, nicotinic or p-toluenesulphonic acid. The free bases can again be liberated from the acid-addition salts by treatment with strong bases, for example, sodium or potassium hydroxide.

Furthermore, the subject of the invention are pharmaceutical compositions which, besides the usual carrier and additive materials, contain at least one of the compounds according to the invention or of their physiologically acceptable salts. These compositions can be used as medicaments in human and veterinary medicine. Conventional carrier materials are, for example, water, vegetable oils, polyethylene glycols, glycerol esters, gelatine, carbohydrates, such as lactose or starch, magnesium stearate, talc or Vaseline. Conventional additive materials are, for example, preserving, stabilising, lubricating, wetting agents, emulsifiers, physiologically acceptable salts, buffer substances, colouring, flavouring and aroma materials. The selection of the carrier and additive materials depends upon whether the compounds according to the invention are to be administered enterally, parenterally or topically.

The compounds according to the invention can also be administered in admixture with other active materials, for example vitamins or known, commercially available heart-circulation agents, especially also with β-receptor blockers.

Example of a pharmaceutical composition

For the preparation of tablets, each of 100 mg. individual weight and each containing 5 mg. of active materials, one needs:

I. 5 g. 5-(4-phenylbutylamino)-5-desoxy-1.4;3.6-dianhydro-L-iditol 2-nitrate hydrochloride
II. 54 g. microcrystalline cellulose
III. 20 g. lactose
IV. 20 g. maize starch
V. 0.5 g. colloidal silicic acid
VI. 0.5 g. magnesium stearate.

The substances I to IV are dry mixed for 10 minutes, subsequently the mixture of the substances V and VI is added thereto, one mixes for a further 10 minutes and presses the so obtained powder on a tabletting machine to give tablets of 100 mg. individual weight.

Each of the compounds and intermediate products according to the invention mentioned in the following Examples represents an especially useful agent for the preparation of pharmaceutical compositions.

The abbreviations contained in the Examples have the following meanings:
m.p. = melting point (uncorrected)
(decomp.) = decomposition
d = density
$[\alpha]_D^{25}$ = optical rotation at 25° C., sodium D line.

After the optical rotation values are given the concentration of the measured solutions, whereby "c 2", for example, signifies a concentration of 2 g./100 ml. of solution; the solvent is, in each case, mentioned separately. All temperatures are given in degrees Celsius.

Example No.1

5-Amino-5-desoxy-1.4;3.6-dianhydro-L-iditol 2-nitrate:
(a) 1.4;3.6-Dianhydro-D-glucitol 2-methanesulphonate, 5-methanesulphonate and 2,5-dimethanesulphonate:

To a solution of 4.82 kg. (33 mol) 1.4;3.6-dianhydro-D-glucitol in 24 liters of pyridine, one adds dropwise, with the exclusion of moisture, stirring and cooling to −15° to −20°, within the course of several hours, 3.1 liters (40 mol) methanesulphonic acid chloride. Subsequently, one further stirs for 15 hours, without cooling. One distils off the pyridine in vacuo, adds 15 liters of water to the oily residue, boils up and allows to cool. Suction filtration, washing with 4 liters of water and drying the crystalline precipitate gives 2.22 kg. (7.34 mol) 1.4;3.6-dianhydro-D-glucitol 2,5-dimethanesulphonate. The filtrate is neutralised, with stirring and water cooling, with about 1.5 kg. sodium hydroxide and evaporated to dryness in a vacuum at about 70°. The dry residue is continuously hot extracted with a total of 30 liters of chloroform and the extract filtered hot. One allows the extract to stand for 15 hours at 20°, filters off the crystalline precipitate with suction, washes it twice with 2 liter amounts of chloroform, dries and obtains 2.3 kg. (10.26 mol) 1.4;3.6-dianhydro-D-glucitol 5-methanesulphonate. The combined filtrates are evaporated in a vacuum and the residue dissolved hot in 22 liters of ethanol. One leaves to stand for 15 hours at 20°, filters off the crystalline precipitate with suction, washes it twice with 3 liter amounts of ethanol, dries and obtains 0.65 kg. (2.90 mol) 1.4;3.6-dianhydro-D-glucitol 2-methanesulphonate. Evaporation of the filtrate gives 2.21 kg. (9.85 mol) of a mixture of the two isomeric monomethanesulphonates which, according to need, can be further separated by repetition of the alternating crystallisations from chloroform and ethanol or, by esterification with methanesulphonic acid chloride in pyridine, is completely converted into 1.4;3.6-dianhydro-D-glucitol, 2,5-dimethanesulphonate.

Analytical amounts of the methanesulphonates give, after recrystallisation, correct elementary analyses and the melting points and optical rotations stated in Table 1:

TABLE 1

| 1.4;3.6-dianhydro-D-glucitol | recrystallised from | m.p. [°C.] | $[\alpha]_D^{25}$ |
|---|---|---|---|
| 2-methanesulphonate | chloroform | 135–138.5 | 62.5 (c 2; acetone) |
| 5-methanesulphonate | chloroform | 123–124 | 75.9 (c 2; methanol) |
| 2,4-dimethane sulphonate | ethanol/acetone | 127–128 | 74 (c 2; acetone) |

Remark:
If one reacts 1.4;3.6-dianhydro-D-glucitol with the 2 to 2.5 fold molar amount of methanesulphonic acid chloride under the same reaction conditions, one obtains 1.4;3.6-dianhydro-D-glucitol 2,5-dimethanesulphonate in almost quantitative yield.

(b) 5-Amino-5-desoxy-1.4;3.6-dianhydro-L-iditol:
This intermediate product can be obtained in 2 ways:

Process 1

Preparation by ammonolysis of 1.4;3.6-dianhydro-D-glucitol 5-methanesulphonate. The mixture of 448 g. (2 mol) 1.4;3.6-dianhydro-D-glucitol 5-methanesulphonate and 1.5 liters of 25% aqueous ammonia (20 mol) is stirred in a closed steel autoclave for 24 hours at 130°. Thereafter, the reaction is quantitative. One evaporates under reduced pressure and dries azeotropically by the successive addition and renewed evaporation of 1 liter amounts of ethanol and chloroform. The oily residue is dissolved, with warming, in 500 ml. ethanol and diluted to 2 liters with isopropanol. Upon cooling, 311 g. (1.3 mol) 5-amino-5-desoxy-1.4;3.6-dianhydro-L-iditol crystallise out as methanesulphonic acid salt. A further 100 g. (0.4 mol) of crystalline pure product precipitate out after treatment of the mother liquor with 30 g. active charcoal and concentration of the filtrate. For analysis, one recrystallises from ethanol/chloroform.

M.p. 151°–4°; $[\alpha]_D^{25}$ 27.6 (c 1; water)

Elementary analysis: $C_6H_{11}NO_3 \times CH_3SO_3H$ (241.27); calc.: C (34.83), H (6.27), N (5.81); found: C (34.71), H (6.45), N (5.36).

A small portion of the product is converted into the free base and recrystallized from chloroform/ether.

M.p. 103°–104°; $[\alpha]_D^{25}$ 31.6 (c 2; water)

Process 2

Ammonolysis of 1.4;3.6-dianhydro-D-glucitol 2,5-dimethanesulphonate, followed by alkaline hydrolysis of the 5-amino-5-desoxy-1.4;3.6-dianhydro-L-iditol 2-methanesulphonate obtained:

A mixture of 302 g. (1 mol) 1.4;3.6-dianhydro-D-glucitol 2,5-dimethanesulphonate, 750 ml. 25% aqueous ammonia (10 mol) and 750 ml. ethanol is stirred in a closed steel autoclave for 4 days at 100°. After cooling, one mixes with 1 liter of water and filters off with suction from unreacted dimethanesulphonate which has crystallised out (106 g.=0.35 mol). For the removal of ammonia, the filtrate is mixed with 104 g. (1.3 mol) sodium hydrogen carbonate and evaporated under reduced pressure. One dissolves in 5 liters of water and extracts elimination products therefrom with 500 ml. chloroform. The aqueous phase is continuously extracted with chloroform in a rotary perforator (Normag). 2,5-Diamino-2,5-didesoxy-1.4;3.6-dianhydro-D-glucitol formed as by-product remains in the aqueous phase.

The chloroform extract gives, after drying over anhydrous sodium sulphate, filtering and evaporating, 105 g. (about 0.55 mol) of a 1:4 mixture of 5-amino-5-desoxy-1.4;3.6-dianhydro-L-iditol and 5-amino-5-desoxy-1.4;3.6-dianhydro-L-iditol 2-methanesulphonate.

For the characterisation of the latter product, a small portion of the mixture is dissolved in chloroform, washed 2 times with water, the chloroform phase is evaporated, converted into the methanesulphonic acid salt and recrystallised 2 times from ethanol.

M.p. 213°–5°; $[\alpha]_D^{25}$ 39.0 (c 0.50; water)

Elementary analysis: $C_7H_{13}NO_5S \times CH_3SO_3H$ (319.37); calc.: C (30.09), H (5.37), N (4.39), S (20.08); found: C (30.13), H (5.49), N (4.25), S (20.6).

The above-obtained mixture is added to a solution of 60 g. (1.5 mol) sodium hydroxide in 1.5 liters of water and boiled under reflux for 24 hours. After cooling, one adjusts to pH=10 by the addition of conc. hydrochloric acid, filters and evaporates under reduced pressure, then dries azeotropically with n-butanol and filters off from inorganic salts. The butanolic solution is evaporated, the residue is dissolved in 200 ml. isopropanol and mixed with 34 g. (0.35 mol) methanesulphonic acid. 80 g. (0.33 mol) 5-Amino-5-desoxy-1.4;3.6-dianhydro-L-iditol crystallise out in the form of the methanesulphonic acid salt. M.p. 150°–2°. Yield, referred to reacted 1.4;3.6-dianhydro-D-glucitol 2,5-dimethanesulphonate: 50%.

(c) 5-Amino-5-desoxy-1.4;3.6-dianhydro-L-iditol 2-nitrate:

241 g. (1 mol) 5-Amino-5-desoxy-1.4;3.6-dianhydro-L-iditol hydrogen methanesulphonate (or 145 g. of the free base) are dissolved in 50 ml. of water and mixed dropwise, with cooling, with 30 ml. conc. sulphuric acid (d=1.84; 0.54 mol) (Solution A).

To 200 ml. 96% nitric acid (d=1.5; 4.5 mol) one adds dropwise, with stirring and cooling to −15°, a solution of 14 g. (0.23 mol) urea in 300 ml. conc. sulphuric acid (d=1.84; 5.4 mol). Subsequently, one adds dropwise at −15° the Solution A within 3–4 hours and further stirs for 2 hours at this temperature. The reaction mixture is slowly stirred into 1.5 liters of water. With cooling, one neutralises by the slow addition of a solution of 630 g. (15.75 mol) sodium hydroxide (or 590 g. NaOH, if the free base has previously been used) in 2 liters of water and filters. The filtrate is continuously extracted with chloroform for 16 hrs. in a 5 liter rotary perforator. From the chloroform extract one obtains, after drying over anhydrous sodium sulphate, filtering and evaporation under reduced pressure, 158 g. (0.83 mol) 5-amino-5-desoxy-1.4;3.6-dianhydro-L-iditol 2-nitrate as slowly crystallising oil, which is dissolved in isopropanol and mixed with the equivalent amount of hydrogen chloride. One heats until dissolving is complete, allows to cool, filters off with suction the product which has crystallised out, then washes with a little isopropanol, concentrates the mother liquor to a small volume and again filters with suction. One obtains 170 g. (0.75 mol) of crystalline 5-amino-5-desoxy-1.4;3.6-dianhydro-L-iditol 2-nitrate hydrochloride, which melts, with decomposition at 201°–208°. $[\alpha]_D^{25}$ 54.1 (c 2; water)

Elementary analysis: $C_6H_{10}N_2O_5 \times HCl$ (226.62); calc: C (31.80), H (4.89), N (12.36), Cl (15.64); found: C (31.78), H (4.92), N (12.20), Cl (15.6).

Example No. 2

5-Amino-5-desoxy-1.4;3.6-dianhydro-D-glucitol 2-nitrate (a) 5-Amino-5-desoxy-1.4;3.6-dianhydro-D-glucitol:
This starting product can be obtained in two ways.

Process 1

Preparation and ammonolysis of 1.4;3.6-dianhydro-L-iditol 2-methanesulphonate.

A solution of 73 g. (480 mmol) 96% 1.4;3.6-dianhydro-L-iditol in 500 ml. anhydrous pyridine is mixed dropwise, with the exclusion of moisture, stirring and cooling to −20°, with 52 ml. (660 mmol) 98% methanesulphonyl chloride and then stirred for 15 hrs. at −20°. The pyridine is distilled off as far as possible under reduced pressure and the residue is warmed, after the addition of 500 ml. hot water, until a solution is obtained. Upon cooling, 47.6 g. (157 mmol) 1.4;3.6-dianhydro-L-iditol 2,5-dimethanesulphonate crystallise out, which are filtered off with suction and then washed twice with 100 ml. amounts of water. The combined filtrates are neutralised (pH=7) by the addition of sodium hydrogen carbonate, evaporated under reduced pressure and dried. The powdered dry residue is boiled up twice with 400 ml. amounts of chloroform and filtered while still hot. After cooling of the filtrate, 1.4;3.6-dianhydro-L-iditol 2-methanesulphonate crystallises out. The mother liquor, after concentration, gives further monomethanesulphonate. In all, one obtains 51.5 g. (213 mmol) 1.4;3.6-dianhydro-L-iditol 2-methanesulphonate. For analysis, a small amount is recrystallised from methanol. M.p. 124°–5°; $[\alpha]_D^{25}$ 33.7 (c 1.0; acetone).

Elementary analysis: $C_7H_{12}O_6S$ (224.24); calc.: C (37.50), N (5.40), S (14.30); found: C (37.58), N (5.53), S (14.0).

33.6 g. (150 mmol) of the so obtained 1.4;3.6-dianhydro-L-iditol 2-methanesulphonate are, together with a solution of 17 g. (1 mol) ammonnia in 250 ml. n-butanol, heated in a closed steel autoclave for 3 days at 170°. After cooling, one filters off with suction the ammonium methanesulphonate which has crystallised out and then washes it with 100 ml. n-butanol. The filtrate is extracted twice with 200 ml. amounts of water. The combined aqueous extracts are washed with 200 ml. chloroform, evaporated to dryness and then dried azeotropically with butanol. The dry residue is boiled with 50 ml. n-butanol, with the addition of 10 g. anhydrous sodium sulphate, filtered hot and the filtrate evaporated. The so obtained oily crude product is taken up in 50 ml. chloroform, filtered and evaporated. One obtains 14 g. (96 mmol) of slowly solidifying 5-amino-5-desoxy-1.4;3.6-dianhydro-D-glucitol. For characterisation, one converts a small portion of the product into the hydrochloride and recrystallises it from isopropanol. Decomposition point: 240°; $[\alpha]_D^{25}$ 39.1 (c 1.0; water)

Elementary analysis: $C_6H_{11}NO_3 \cdot xHCl$ (181.63); calc.: C (39.68), H (6.66), N (7.71), Cl (19.52); found: C (39.85), H (6.89), N (7.66), Cl (19.3).

Process 2

Preparation and selective ammonolysis of 1.4;3.6-dianhydro-L-iditol 2-methanesulphonate 5-benzoate.

A mixture of 604 g. (2 mol) 1.4;3.6-dianhydro-D-glucitol 2,5-dimethanesulphonate, 317 g. (2.2 mol) sodium benzoate and 8 liters anhydrous dimethylformamide is stirred for 2 days at 145° in a steel autoclave under a protective atmosphere of nitrogen. The dimethylformamide is distilled off under reduced pressure, the residue is taken up in 5 liters chloroform, successively extracted with 2 liter amounts of 1 molar aqueous sodium hydroxide solution and water, the chloroform phase is dried with anhydrous sodium sulphate, filtered and concentrated to a volume of 1500 ml. The crude product which crystallises out upon standing is filtered off with suction, dissolved in 500 ml. acetone with warming and the hot solution poured into 1000 ml. ethanol. Upon cooling, 273 g. (0.83 mol) 1.4;3.6-dianhydro-L-iditol 2-methanesulphonate 5-benzoate crystallise out. The mother liquor gives, after evaporation and recrystallisation, a further 120 g. (0.37 mol) of product slightly contaminated by starting substance. The analytical sample has, after recrystallisation from ethanol, the m.p. 117° and $[\alpha]_D^{25}$ 76.6 (c 2; chloroform).

Elementary analysis: $C_{14}H_{16}O_7S$ (328.35); calc.: C (51.21), H (4.91), S (9.76); found: C (51.60), H (5.05), S (9.6).

328 g. (1 mol) of the so obtained 1.4;3.6-dianhydro-L-iditol 2-methanesulphonate 5-benzoate are, together with 1 liter ethanol and 1.5 liter 25% aqueous ammonia, stirred for 1 day at 130° in a closed steel autoclave. One evaporates under reduced pressure, dissolves the residue in 1 liter water, adjusts to pH=1 by the addition of conc. hydrochloric acid and filters off with suction the precipitate-consisting of benzoic acid and benzamide. The filtrate is, after washing twice with 500 ml. amounts of chloroform, brought to pH=8 by the addition of sodium hydrogen carbonate, again evaporated and the residue extracted with 2 liters ethanol. The ethanol extract is, after evaporation, extracted with 2 liters chloroform, the chloroform extract boiled with 60 g. active charcoal, filtered and evaporated. The so obtained 105 g. of crude product give, after fractional distillation at 0.2 mm.Hg and 136°–142° distilling over temperature, 86.3 g. (0.59 mol) 5-amino-5-desoxy-1.4;3.6-dianhydro-D-glucitol.

(b) 5-Amino-5-desoxy-1.4;3.6-dianhydro-D-glucitol 2-nitrate:

55 g. (0.38 mol) of the 5-amino-5-desoxy-1.4;3.6-dianhydro-D-glucitol obtained according to Process 1 or 2 are liquified by mixing with 3.5 ml. chloroform and this solution added dropwise, with stirring, to a solution, cooled to −15°, of 14 g. (0.23 mol) urea and 202 ml. (4.6 mol) 96% nitric acid (d=1.5). One further stirs for 15 hrs. at −15°, dilutes with 750 ml. water and neutralises, with cooling, with a solution of 168 g. (4.2 mol) sodium hydroxide in 1.5 liters of water. One adjusts to pH=8 with sodium hydrogen carbonate, filters and continuously extracts the aqueous solution for 16 hrs. with chloroform in a 5 l. rotary perforator (Normag). The chloroform extract, after drying with anhydrous sodium sulphate and filtering, is evaporated under reduced pressure. The residue is dissolved in 200 ml. dichloromethane, freed from inorganic impurities by filtration and again evaporated under reduced pressure. One obtains 53 g. (0.28 mol) 5-amino-5-desoxy-1.4;3.6-dianhydro-D-glucitol 2-nitrate as a pale yellowish oil. For characterisation, one converts a part into the hydrochloride and recrystallises from ethanol/-chloroform/petroleum ether. M.p. 170°–1° (decomp.); $[\alpha]_D^{25}$ 50.7 (c 0.53; water)

Elementary analysis: $C_6H_{10}N_2O_5 \cdot xHCl$ (226.62); calc.: C (31.80), H (4.89), N (12.36), Cl (15.64); found: C (32.00), H (5.10), N (12.14), Cl (15.6).

Example No. 3

2-Amino-2-desoxy-1.4;3.6-dianhydro-D-glucitol 5-nitrate (a) 1.4;3.6-Dianhydro-D-mannitol 2-methanesulphonate:

To a solution of 877 g. (6 mol) 1.4;3.6-dianhydro-D-mannitol in 6 liters of pyridine, one adds dropwise, with stirring and the exclusion of moisture, as well as cooling to −15°, within 6 hrs., 525 ml. (6.6 mol) methanesulphonyl chloride, stirs for a further 3 days at −15° and then distils off the pyridine under reduced pressure. Upon mixing the oily residue with 2.7 liters water, pure 1.4;3.6-dianhydro-D-mannitol 2,5-dimethanesulphonate crystallises out, which is separated off and washed 2 times with 700 ml. amounts of water. The combined filtrates are mixed with a solution of 264 g. (6.6 mol) sodium hydroxide in 2.5 liters water, adjusted to pH=7 by the addition of sodium hydrogen carbonate, evaporated under reduced pressure and dried azeotropically with chloroform. The residue is hot extracted twice with 2.5 liter amounts of chloroform and filtered. The combined chloroform extracts are extracted 5 times with 1 liter amounts of water. Upon concentration of the aqueous phase, 1.4;3.6-dianhydro-D-mannitol 2-methanesulphonate crystallises out. The mother liquor remaining after the suction filtration gives further product after evaporating and recrystallising from ethanol. Residual product is obtained by evaporation of the ethanolic mother liquor, dissolving the residue in water and continuous extraction of the aqueous solution with chloroform in a rotary perforator. Unreacted 1.4;3.6-dianhydro-D-mannitol remains in the aqueous phase. In all, one obtains 396 g. (1.77 mol) 1.4;3.6-dianhydro-D-mannitol 2-methanesulphonate (besides 465 g.=1.54 mol of the dimethanesulphonate). The analytical sample has, after recrystallisation from chloroform, the m.p. 111°-112° and $[\alpha]_D^{25}$ 118 (c 1.0; acetone).

Elementary analysis: $C_7H_{12}O_6S$ (224.24); calc.: C (37.50), H (5.40), S (14.30); found: C (37.41), H (5.59), S (13.7).

(b) 2-Amino-2-desoxy-1.4;3.6-dianhydro-D-glucitol:

A mixture of 224 g. (1 mol) of the previously obtained 1.4;3.6-dianhydro-D-mannitol 2-methanesulphonate and 1 liter 25% aqueous ammonia is stirred for 24 hrs. at 120° in a closed steel autoclave. After cooling, one adds 84 g. (1 mol) sodium hydrogen carbonate thereto, evaporates under reduced pressure and boils up the residue with 2 liters n-butanol. The evaporated butanol extract is taken up in 1 liter chloroform, residual sodium methanesulphonate is filtered off and the filtrate evaporated. One obtains 130 g. (0.9 mol) 2-amino-2-desoxy-1.4;3.6-dianhydro-D-glucitol as a pale yellowish oil. For characterisation, one converts a small portion into the hydrochloride and recrystallises from isopropanol/methanol/chloroform.

M.p. 230° (decomp.); $[\alpha]_D^{25}$ 52.1 (c 1.0; water)

Elementary analysis: $C_6H_{11}NO_3xHCl$ (181.62); calc.: C (39.68), H (6.66), N (7.71), Cl (19.52); found: C (39.59), H (6.89), N (7.52), Cl (19.3).

(c) 2-Amino-2-desoxy-1.4;3.6-dianhydro-D-glucitol 5-nitrate:

With stirring and cooling to −15°, to 200 ml. (4.5 mol) 96% nitric acid (d=1.5), one first adds dropwise a solution of 14 g. (0.23 mol) urea in 300 ml. (5.4 mol) sulphuric acid (d=1.84) and subsequently, within 4 hrs., a solution of 145 g. (1 mol) 2-amino-2-desoxy-1.4;3.6-dianhydro-D-glucitol in 50 ml. water and then stirs for 2 hrs. at −15°. One then stirs into 1.5 liters of water, adjusts to pH=8 to 9 by the gradual addition of 570 g. (14.3 mol) sodium hydroxide-dissolved in 2 liters water, filters off sodium sulphate which has crystallised out, washes lipophilic by-products therefrom with 500 ml. chloroform and continuously extracts with chloroform for 16 hrs. in a rotary perforator. The chloroform extract gives, after drying over anhydrous sodium sulphate, filtering and evaporating under reduced pressure, 152 g. (0.8 mol) 2-amino-2-desoxy-1.4;3.6-dianhydro-D-glucitol 5-nitrate as a slowly solidifying oil. For characterisation, a part is converted into the hydrochloride and recrystallised from isopropanol/ethanol.

M.p. 181°-2° (decomp.); $[\alpha]_D^{25}$ 130 (c 0.52; water)

Elementary analysis: $C_6H_{10}N_2O_5xHCl$ (226.62); calc.: C (31.80), H (4.89), N (12.36), Cl (15.6); found: C (31.95), H (4.90), N (12.18), Cl (15.9).

Example No. 4

5-Amino-5-desoxy-1.4;3.6-dianhydro-D-mannitol 2-nitrate (a) 2-Amino-2-desoxy-1.4;3.6-dianhydro-D-mannitol:

A mixture of 448 g. (2 mol) 1.4;3.6-dianhydro-D-glucitol 2-methanesulphonate (preparation see Example 1a) and 1500 ml. 25% aqueous ammonia is stirred for 1 day at 130° in a closed steel autoclave. After cooling, one adds 30 g. active charcoal thereto, filters and extracts with 1 liter chloroform the 1.4;2.5;3.6-trianhydro-D-mannitol formed as by-product [after evaporation of the chloroform phase and recrystallisation from ether/petroleum ether, a total of 104 g. (0.81 mol)]. The aqueous phase is, after evaporating under reduced pressure and azeotropic drying with ethanol and chloroform, extracted at boiling temperature with 2 liters isopropanol. Upon concentrating the isopropanol extract to 0.5 liter, ammonium methanesulphonate which has crystallised out is filtered off, the filtrate is neutralised with dilute aqueous sodium hydroxide solution, evaporated and extracted hot with 1 liter n-butanol. The butanol extract is evaporated and the residue extracted with 1 liter chloroform. Evaporation of the filtered chloroform extract gives 60 g. (0.41 mol) of oily crude base which is dissolved in 100 ml. acetic acid and mixed dropwise with a solution of 15 ml. 96% nitric acid (d=1.5) in 75 ml. acetic acid. The hydrogen nitrate which crystallises out is filtered off with suction and recrystallised from isopropanol/ethanol. One obtains 32 g. (154 mmol) 2-amino-2-desoxy-1.4;3.6-dianhydro-D-mannitol hydrogen nitrate.

M.p. 192°-3° (decomp.); $[\alpha]_D^{25}$ 63.4 (c 0.51; water)

Elementary analysis: $C_6H_{11}NO_3xHNO_3$ (208.18); calc.: C (34.62), H (5.81), N (13.45); found: C (34.52), H (5.97), N (13.53).

A small portion is converted into the hydrochloride and recrystallised from ethanol.

M.p. 263°-8° (decomp.); $[\alpha]_D^{25}$ 77.8 (c 1; water)

Elementary analysis: $C_6H_{11}NO_3xHCl$ (181.63); calc.: C (39.68), H (6.66), N (7.71), Cl (19.52); found: C (39.82), H (6.68), N (7.59), Cl (19.4).

(b) 5-Amino-5-desoxy-1.4;3.6-dianhydro-D-mannitol 2-nitrate:

To 60 ml. (1.35 mol) 96% nitric acid (d=1.5) one adds dropwise, with stirring and cooling to −15°, a solution of 4.2 g. (70 mmol) urea in 90 ml. (1.6 mol) sulphuric acid (d=1.84). At the same temperature, one slowly adds dropwise thereto a solution of 21.8 g. (150 mmol) 2-amino-2-desoxy-1.4;3.6-dianhydro-D-mannitol (prepared from the previously obtained hydrogen nitrate) in 15 ml. water, then stirs for 2 hrs. at −15°, pours the reaction mixture into 1 liter of water, with stirring, and adjusts to pH=9 by the slow addition of 175 g. (4.38 mol) sodium hydroxide-dissolved in 1 l. water. Subsequently one extracts continuously with chloroform for 8 hrs. in a rotary perforator. The chloroform extract, after drying with anhydrous sodium sulphate, filtering and evaporating under reduced pressure, gives 18.8 g. (99 mmol) 5-amino-5-desoxy-1.4;3.6-dianhydro-D-mannitol 2-nitrate as a slowly crystallising oil. For characterisation, one converts a portion into the hydrochloride and recrystallises from ethanol.

M.p. 172° (decomp.); $[\alpha]_D^{25}$ 170.9 (c 0.5; water)

Elementary analysis: $C_6H_{10}N_2O_5$ x HCl (226.62); calc.: C (31.80), H (4.89), N (12.36), Cl (15.64); found: C (31.76), H (4.93), N (12.67), Cl (16.0).

Example No. 5

5-Pivaloylamino-5-desoxy-1.4;3.6-dianhydro-L-iditol 2-nitrate:

To a solution of 3.8 g. (20 mmol) 5-amino-5-desoxy-1.4;3.6-dianhydro-L-iditol 2-nitrate (preparation according to Example 1 c) in 30 ml. water, one adds 30 ml. 1 molar aqueous sodium hydroxide solution and 30 ml.

ether. With vigorous stirring, one adds dropwise a solution of 3.6 g. (30 mmol) pivaloyl chloride in 30 ml. ether thereto and subsequently heats under reflux for 2 hrs. After cooling, one separates off the ether phase, extracts the aqueous phase with 50 ml. ether, dries the combined ether phases over anhydrous sodium sulphate, filters and precipitates out the product with petroleum ether. The precipitate gives, after recrystallisation from ether/petroleum ether, 4.95 g. (18 mmol) 5-pivaloylamino-5-desoxy-1.4;3.6-dianhydro-L-iditol 2-nitrate.

M.p. 96°–97°; $[\alpha]_D^{25}$ 35.7 (c 0.53; chloroform).

Elementary analysis: $C_{11}H_{18}N_2O_6$ (274.27); calc.: C (48.17), H (6.61), N (10.21); found: C (47.97), H (6.74), N (10.29).

Example No. 6

5-Acetylamino-5-desoxy-1.4;3.6-dianhydro-L-iditol 2-nitrate:

With vigorous stirring, one adds a solution of 2.2 ml. (30 mmol) acetyl chloride in 20 ml. ether dropwise to a mixture of 3.8 g. (20 mmol) 5-amino-5-desoxy-1.4;3.6-dianhydro-L-iditol 2-nitrate, 30 ml. ether and 20 ml. water. By the simultaneous dropwise addition of 1 molar aqueous sodium hydroxide solution, one keeps the reaction mixture at pH=7–8. One then stirs for 2 hrs. at pH=7, separates off the ether phase, extracts the aqueous phase 2 times with 30 ml. chloroform, evaporates the ether and chloroform phases under reduced pressure and recrystallises the residue from chloroform/ether. One obtains 3.2 g. (14 mmol) 5-acetylamino-5-desoxy-1.4;3.6-dianhydro-L-iditol 2-nitrate.

M.p. 104°–6°; $[\alpha]_D^{25}$ 33.7 (c 0.67; methanol)

Elementary analysis: $C_8H_{12}N_2O_6$ (232.20); calc.: C (41.38), H (5.21), N (12.06); found: C (41.44), H (5.34), N (11.32).

Example No. 7

5-Nicotinoylamino-5-desoxy-1.4;3.6-dianhydro-L-iditol 2-nitrate:

To a suspension of 5.4 g. (30 mmol) nicotinic acid chloride hydrochloride in 100 ml. chloroform, one adds dropwise, with stirring, a solution of 19 g. (100 mmol) 5-amino-5-desoxy-1.4;3.6-dianhydro-L-iditol 2-nitrate in 50 ml. chloroform and stirs for a further 15 hrs. Excess starting amine precipitates out as hydrochloride and is filtered off with suction. Residual starting amine is recovered by extraction of the filtrate with a total of 100 ml. 0.2 molar acetic acid. The chloroform solution gives, after washing with 50 ml. 1 molar aqueous sodium hydroxide solution, drying over anhydrous sodium sulphate and evaporation under reduced pressure, 5.3 g. (18 mmol) of crude product, which is dissolved in ethanol and converted into the hydrochloride by the addition of the equimolar amount of hydrochloric acid. Evaporation under reduced pressure and recrystallisation of the residue from isopropanol/ethanol gives 4.3 g. (13 mmol) 5-nicotinoylamino-5-desoxy-1.4;3.6-dianhydro-L-iditol 2-nitrate hydrochloride.

M.p. 173°–5° (decomp.); $[\alpha]_D^{25}$ 41.8 (c 1; water)

Elementary analysis: $C_{12}H_{13}N_3O_6 \cdot xHCl$ (331.71); calc.: C (43.45), H (4.25), N (12.67), Cl (10.69); found: C (43.58), H (4.29), N (12.21), Cl (10.8).

Example No. 8

5-(2-Acetoxybenzoylamino)-5-desoxy-1.4;3.6-dianhydro-L-iditol 2-nitrate.

To a mixture of 3.8 g. (20 mmol) 5-amino-5-desoxy-1.4;3.6-dianhydro-L-iditol 2-nitrate, 20 ml. water and 30 ml. ether, one adds dropwise, with vigorous stirring, a solution of 4.0 g. (20 mmol) O-acetylsalicylic acid chloride in 50 ml. ether. By the simultaneous dropwise addition of 1 molar aqueous sodium hydroxide solution, one keeps the reaction mixture at pH=7. One further stirs for 2 hrs. at pH=7, filters off with suction product which has precipitated out (4 g.) and then washes the precipitate with water. One obtains a further 1.3 g. of product from the ether phase of the filtrate which is successively washed with 50 ml. 0.1 molar hydro chloric acid and with 50 ml. aqueous sodium hydrogen carbonate solution, dried over anhydrous sodium sulphate and evaporated. The so obtained 5.3 g. of crude product gives, after recrystallisation from ethanol (with the addition of active charcoal), pure 5-(2-acetoxybenzoylamino)-5-desoxy-1.4;3.6-dianhydro-L-iditol 2-nitrate.

M.p. 123°–5°; $[\alpha]_D^{25}$ 64.2 (c 0.52; chloroform)

Elementary analysis: $C_{15}H_{16}N_2O_8$ (352.31); calc.: C (51.14), H (4.58), N (7.95); found: C (51.59), H (4.69), N (7.93).

Example No. 9

5-Methylamino-5-desoxy-1.4;3.6-dianhydro-L-iditol 2-nitrate (a) 5-Methylamino-5-desoxy-1.4;3.6-dianhydro-L-iditol:

A mixture of 22.4 g. (0.1 mol) 1.4;3.6-dianhydro-D-glucitol 5-methanesulphonate (preparation see Example 1a), 31 g. (1 mol) methylamine and 150 ml. n-butanol is stirred in a closed steel autoclave for 15 hrs. at 150° under an atmosphere of nitrogen. After cooling, one adds thereto a solution of 4 g. (0.1 mol) sodium hydroxide in 200 ml. n-butanol, stirs up, precipitates out the sodium methanesulphonate formed with 600 ml. chloroform, filters and evaporates the filtrate under reduced pressure. The so obtained oily crude base is dissolved in 100 ml. isopropanol and converted into the hydrogen nitrate with 6.5 ml. 65% nitric acid. After evaporation under reduced pressure, one recrystallises from isopropanol and obtains 15.3 g. (68.9 mmol) 5-methylamino-5-desoxy-1.4;3.6-dianhydro-L-iditol hydrogen nitrate.

M.p. 108°–9°; $[\alpha]_D^{25}$ 41.8 (c 1.0; water)

Elementary analysis: $C_7H_{13}NO_3 \cdot xHNO_3$ (222.20); calc.: C (37.84), H (6.35), N (12.61); found: C (38.00), H (6.60), N (12.23).

(b) 5-Methylamino-5-desoxy-1.4;3.6-dianhydro-L-iditol 2-nitrate:

With stirring and cooling to 10°, one adds a solution of 5.9 ml. (138 mmol) 95% nitric acid in 46 ml. acetic acid dropwise to a mixture of 90 ml. acetic acid, 2.3 g. (38 mmol) urea and 10.2 g. (46 mmol) 5-methylamino-5-desoxy-1.4;3.6-dianhydro-L-iditol hydrogen nitrate and subsequently 46 ml. acetic anhydride. After stirring for a further 4 hrs. at 10°, one precipitates out the crystalline reaction product with ether/petroleum ether and filters off with suction. The precipitate, dissolved in 200 ml. water, is neutralised by the addition of sodium hydrogen carbonate and the solution extracted 4 times with 150 ml. amounts of chloroform. The chloroform extracts, after washing with 100 ml. water, drying over anhydrous sodium sulphate/sodium carbonate and filtering, is evaporated under reduced pressure. The so obtained crude base is dissolved in 100 ml. ethanol, converted with 46 ml. 1 molar hydrochloric acid into the hydrochloride, again evaporated under reduced pressure and recrystallised twice from ethanol/isopropanol. One obtains 5.58 g. (23.2 mmol) 5-methylamino-5-desoxy-1.4;3.6-dianhydro-L-iditol 2-nitrate hydrochloride.

M.p. 163°–6° (decomp.); $[\alpha]_D^{25}$ 49 (c 1.0; water)

Elementary analysis: $C_7H_{12}N_2O_5xHCl$ (240.64); calc.: C (34.94), H (5.44), N (11.64), Cl (14.73); found: C (35.00), H (5.57), N (11.92), Cl (14.8).

Example No. 10

5-Ethylamino-5-desoxy-1.4;3.6-dianhydro-L-iditol 2-nitrate (a) 5-Ethylamino-5-desoxy-1.4;3.6-dianhydro-L-iditol:

A mixture of 11.2 g. (50 mmol) 1.4;3.6-dianhydro-D-glucitol 5-methanesulphonate, 40.5 g. (500 mmol) ethylamine hydrochloride, 20 g. (500 mmol) sodium hydroxide and 200 ml. water is stirred in a closed steel autoclave for 15 hrs. at 150° under an atmosphere of nitrogen. After cooling and decompressing, one adds 2 g. (50 mmol) sodium hydroxide thereto, evaporates to dryness under reduced pressure, extracts the residue not with chloroform and evaporates the extract to dryness. One obtains 9 g. (about 50 mmol) oily 5-ethylamino-5-desoxy-1.4;3.6-dianhydro-L-iditol, which is used for the subsequent esterification with nitric acid. For characterisation, a small portion is converted into the hydrochloride and recrystallised 2 times from isopropanol.

M.p. 181°–3° (decomp.); $[\alpha]_D^{25}$ 51.3 (c 1; water)

Elementary analysis: $C_8H_{15}NO_3xHCl$ (209.68); calc.: C (45.83), H (7.69), N (6.68), C. (16.91); found: C (46.26), H (8.06), N (6.69), Cl (16.9).

(b) 5-Ethylamino-5-desoxy-1.4;3.6-dianhydro-L-iditol 2-nitrate:

To a mixture of 6 g. (35 mmol) 5-ethylamino-5-desoxy-1.4;3.6-dianhydro-L-iditol, 70 ml. acetic acid and 2.1 g. (35 mmol) urea, one adds dropwise, with stirring and cooling to 10°, first a solution of 6.2 ml. (140 mmol) 96% nitric acid (d=1.5) in 35 ml. acetic acid and subsequently 35 ml. acetic anhydride. One stirs the resulting suspension for 3 hrs. at 10°, whereby a clear solution is obtained. The crude product is precipitated out as hydrogen nitrate with 800 ml. ether, the precipitate is separated off, dissolved in 100 ml. water and neutralised with sodium hydrogen carbonate. Threefold extraction with 200 ml. amounts of chloroform, drying over anhydrous sodium sulphate and evaporating under reduced pressure gives an oily crude product in the form of the free base. One converts into the hydrochloride in ethanolic solution with the equimolar amount of hydrochloric acid, again evaporates under reduced pressure, recrystallises from dichloromethane and obtains 4.2 g. (16.5 mmol) 5-ethylamino-5-desoxy-1.4;3.6-dianhydro-L-iditol 2-nitrate hydrochloride.

M.p. 146°–7° (decomp.); $[\alpha]_D^{25}$ 59.5 (c 0.7; water)

Elementary analysis: $C_8H_{14}N_2O_5xHCl$ (254.67); calc.: C (37.73), H (5.94), N (11.00), Cl (13.92); found: C (38.07), H (6.30), N (10.84), Cl (14.2).

Example No. 11

5-Adamant-1-ylamino-5-desoxy-1.4;3.6-dianhydro-L-iditol 2-nitrate (a) 5-Adamant-1-ylamino-5-desoxy-1.4;3.6-dianhydro-L-iditol:

A mixture of 11.2 g. (50 mmol) 1.4;3.6-dianhydro-D-glucitol 5-methanesulphonate, 39 g. (250 mmol) 1-aminoadamantane and 100 ml. n-butanol is heated for 3 days in a closed steel autoclave at 150°. Subsequently, one evaporates to dryness under reduced pressure, dissolves the residue in 250 ml. chloroform, first recovers excess adamantylamine by extraction with 1 molar hydrochloric acid and, by further extraction, the reaction product. The hydrochloric acid solution of the reaction product is adjusted to pH=8 with dilute aqueous sodium hydroxide solution and re-extracted with chloroform. Evaporation of the chloroform phase, dried over anhydrous sodium sulphate, gives 3.85 g. (13.8 mmol) 5-adamant-1-ylamino-5-desoxy-1.4;3.6-dianhydro-L-iditol. For analysis, one recrystallises from cyclohexane.

M.p. 126°–7°; $[\alpha]_D^{25}$ 26.0 (c 1; ethanol)

Elementary analysis: $C_{16}H_{25}NO_3$ (279.39); calc.: C (68.79), H (9.02), N (5.01); found: C (68.80), H (9.25), N (5.07).

(b) 5-Adamant-1-ylamino-5-desoxy-1.4;3.6-dianhydro-L-iditol 2-nitrate:

To a mixture of 2.08 g. (7.44 mmol) 5-adamant-1-ylamino-1.4;3.6-dianhydro-L-iditol, 0.5 g. (8.3 mmol) urea and 40 ml. acetic acid, one adds dropwise, with stirring and cooling to 10°–15°, a solution of 1.3 ml. (30 mmol) 96% nitric acid in 10 ml. acetic acid and subsequently 10 ml. acetic anhydride. One stirs for 3 hrs. at 15° and precipitates out the product with ether/petroleum ether. The so obtained oily crude product is dissolved in 200 ml. chloroform and washed acid-free with aqueous sodium hydrogen carbonate solution. One dries over anhydrous sodium sulphate, adds 8 mmol ethanolic hydrochloric acid thereto, evaporates under reduced pressure, recrystallises from ethanol/isopropanol and obtains 2.11 g. (5.85 mmol) 5-adamant-1-ylamino-5-desoxy-1.4;3.6-dianhydro-L-iditol 2-nitrate hydrochloride.

M.p. 207°–10° (decomp.); $[\alpha]_D^{25}$ 30.1 (c 1; ethanol)

Elementary analysis: $C_{16}H_{24}N_2O_5xHCl$ (360.84); calc.: C (53.26), H (6.98), N (7.76), Cl (9.82); found: C (53.22), H (7.25), N (7.60), Cl (10.2).

Example No.12

5-Dimethylamino-5-desoxy-1.4;3.6-dianhydro-L-iditol 2-nitrate (a) 5-Dimethylamino-5-desoxy-1.4;3.6-dianhydro-L-iditol:

22.5 g. (0.5 mol) Dimethylamine are dissolved, with cooling, in 100 ml. n-butanol, mixed with 11.2 g. (50 mmol) 1.4;3.6-dianhydro-D-glucitol 5-methanesulphonate and heated for 15 hrs. in a closed steel autoclave to 150°. After cooling and decompressing, one adds thereto 100 ml. 0.5 molar butanolic sodium hydroxide solution, filters and evaporates under reduced pressure. The residue is extracted with chloroform and the chloroform extract evaporated under reduced pressure. One obtains 8.5 g. (49 mmol) oily 5-dimethylamino-5-desoxy-1.4;3.6-dianhydro-L-iditol. For characterisation, one converts a small portion into the hydrochloride and recrystallises from isopropanol.

M.p. 227°–9°; $[\alpha]_D^{25}$ 46.8 (c 0.58; water)

Elementary analysis: $C_8H_{15}NO_3xHCl$ (209.68); calc.: C (45.82); H (7.69), N (6.68), Cl (16.91); found: C (46.02), H (7.96), N (6.79), Cl (16.6).

(b) 5-Dimethylamino-5-desoxy-1.4;3.6-dianhydro-L-iditol 2-nitrate:

The previously obtained 5-dimethylamino-5-desoxy-1.4;3.6-dianhydro-L-iditol is dissolved in isopropanol and precipitates out as hydrogen nitrate by the addition of the equimolar amount of 65% nitric acid. 4.7 g. (20 mmol) of the hydrogen nitrate are esterified with nitric acid analogously to Example 9 b, subsequently converted into the hydrochloride and recrystallised from ethanol/isopropanol. One obtains 3.67 g. (14.4 mmol) 5-dimethylamino-5-desoxy-1.4;3.6-dianhydro-L-iditol 2-nitrate hydrochloride.

M.p. 184°–9° (decomp.); $[\alpha]_D^{25}$ 50.9 (c 1; water)

Elementary analysis: $C_8H_{14}N_2O_5xHCl$ (254.67); calc.: C (37.73), H (5.94), N (11.00), Cl (13.92); found: C (37.70), H (6.07), N (10.93), Cl (14.3).

Example No.13

5-Diethylamino-5-desoxy-1.4;3.6-dianhydro-L-iditol 2-nitrate.

(a) 5-Diethylamino-5-desoxy-1.4;3.6-dianhydro-L-iditol:

Preparation analogously to Example 12 (a) by the reaction of excess diethylamine with 1.4;3.6-dianhydro-D-glucitol 5-methanesulphonate in butanol at 150°. Isolation as hydrogen nitrate.

M.p. 129° (from isopropanol); $[\alpha]_D^{25}$ 39.8 (c 1; water)

Elementary analysis: $C_{10}H_{19}NO_3xHNO_3$ (264.38); calc.: C (45.45), H (7.63), N (10.60); found: C (44.97), H (7.86), N (10.65).

(b) 5-Diethylamino-5-desoxy-1.4;3.6-dianhydro-L-iditol 2-nitrate:

2.1 g. (8 mmol) of the previously obtained hydrogen nitrate are esterified with nitric acid analogously to Example 9 (b) and give, after conversion into the hydrochloride and recrystallisation from ethanol/isopropanol, 1.6 g. (5.7 mmol) of pure product.

M.p. 182°–6° (decomp.); $[\alpha]_D^{25}$ 45.3 (c 1; water)

Elementary analysis: $C_{10}H_{18}N_2O_5xHCl$ (282.72); calc.: C (42.48), H (6.77), N (9.91), Cl (12.54); found: C (42.62), H (7.24), N (9.64), Cl (12.8).

Example No.14

5-Pyrrolidino-5-desoxy-1.4;3.6-dianhydro-L-iditol 2-nitrate (a) 5-Pyrrolidino-5-desoxy-1.4;3.6-dianhydro-L-inditol:

A mixture of 11.2 g. (50 mmol) 1.4;3.6-dianhydro-D-glucitol 5-methanesulphonate, 36 g. (0.5 mol) pyrrolidine and 100 ml. n-butanol is heated in a closed steel autoclave under a protective atmosphere of nitrogen for 24 hrs. at 150°. After cooling, one adds 10 ml. 5 molar aqueous sodium hydroxide solution thereto, evaporates off excess pyrrolidine under reduced pressure—towards the end, with the addition of water—and extracts the product from the residue with chloroform. The evaporated chloroform extract is freed from insoluble by-products by dissolving in ether. The ether filtrate gives, after drying over anhydrous sodium sulphate and evaporation, 8.7 g. (43.7 mmol) 5-pyrrolidino-5-desoxy-1.4;3.6-dianhydro-L-iditol. For characterisation, a small portion is converted into the hydrogen nitrate and recrystallised from isopropanol.

M.p. 123°–4°; $[\alpha]_D^{25}$ 45.9 (c 1; ethanol)

Elementary analysis: $C_{10}H_{17}NO_3xHNO_3$ (262.26); calc.: C (45.80), H (6.92), N (10.68); found: C (45.74), H (7.16), N (10.79).

(b) 5-Pyrrolidino-5-desoxy-1.4;3.6-dianhydro-L-iditol 2-nitrate:

To a mixture of 6 g. (30 mmol) 5-pyrrolidino-5-desoxy-1.4;3.6-dianhydro-L-iditol, 1.5 g. (25 mmol) urea and 60 ml. acetic acid, one adds dropwise, with stirring and cooling to 10°, a solution of 4 ml. (90 mmol) 95% nitric acid in 30 ml. acetic acid and subsequently 30 ml. acetic anhydride. One stirs for 4 hrs. at 10°, dilutes with 400 ml. water, stirs for ½ hour and adds 7.5 g. sodium hydrogen carbonate thereto. After ending of the hydrolysis of the acetic anhydride, one adjusts to pH=6–7 with further sodium hydrogen carbonate and extracts 3 times with 180 ml. amounts of chloroform. The combined chloroform extracts are evaporated under reduced pressure, converted into the hydrochloride with 1 molar hydrochloric acid, again evaporated and recrystallised from isopropanol. One obtains 3.4 g. (12.1 mmol) of pyrrolidino-5-desoxy-1.4;3.6-dianhydro-L-iditol 2-nitrate hydrochloride.

M.p. 172°–3° (decomp.); $[\alpha]_D^{25}$ 52.7 (c 0.52; water)

Elementary analysis: $C_{10}H_{16}N_2O_5xHCl$ (280.71); calc.: C (42.79), H (6.11), N (9.98), Cl (12.63); found: C (43.05), H (6.20), N (10.01), Cl (12.4).

Example No.15

5-Piperidino-5-desoxy-1.4;3.6-dianhydro-L-iditol 2-nitrate (a) 5-Piperidino-5-desoxy-1.4;3.6-dianhydro-L-iditol:

A mixture of 11.2 g. (50 mmol) 1.4;3.6-dianhydro-D-glucitol 5-methanesulphonate, 42.5 g. (0.5 mol) piperidine and 100 ml. n-butanol is heated for 24 hrs. in a closed steel autoclave under an atmosphere of nitrogen to 150°. After evaporation under reduced pressure, one extracts the residue with ether, whereby piperidine hydrogen methanesulphonate remains undissolved. The ether extract, dried over anhydrous sodium sulphate, gives, after evaporation, 10 g. (47 mmol) of product which is dissolved in 50 ml. acetic acid and converted into the hydrogen nitrate with the equimolar amount of 30% nitric acid. This is precipitated out with ether and gives, after recrystallisation from isopropanol, 11.6 g. (42 mmol) 5-piperidino-5-desoxy-1.4;3.6-dianhydro-L-iditol hydrogen nitrate.

M.p. 182°–4° (decomp.); $[\alpha]_D^{25}$ 46.0 (c 1; ethanol)

Elementary analysis: $C_{11}H_{19}NO_3xHNO_3$ (276.29); calc.: C (47.82), H (7.30), N (10.14); found: C (47.80), H (7.44), N (10.21).

(b) 5-Piperidino-5-desoxy-1.4;3.6-dianhydro-L-iditol 2-nitrate:

8.3 g (30 mmol) of the previously obtained hydrogen nitrate are esterified with nitric acid analogously to Example 9 (b), converted into the hydrochloride and recrystallised from isopropanol. Yield: 7.2 g. (24.4 mmol).

M.p. 186°–8° (decomp.); $[\alpha]_D^{25}$ 47.0 (c 0.5; water)

Elementary analysis: $C_{11}H_{18}N_2O_5xHCl$ (294.73); calc.: C (44.83), H (6.50), N (9.50), Cl (12.03); found: C (44.73), H (6.58), N (9.53), Cl (11.8).

Example No.16

5-Morpholino-5-desoxy-1.4;3.6-dianhydro-L-iditol 2-nitrate (a) 5-Morpholino-5-desoxy-1.4;3.6-dianhydro-L-iditol:

Preparation analogous to Example 12 (a) by the reaction of 50 mmol 1.4;3.6-dianhydro-D-glucitol 5-methanesulphonate with 0.5 mol morpholine. Yield 8.6 g. (40 mmol) of oily product. Characterisation as hydrochloride.

M.p. 159°–161° (from isopropanol/ethanol); $[\alpha]_D^{25}$ 48.5 (C 1; ethanol)

Elementary analysis: $C_{10}H_{17}NO_4xHCl$ (251.71); calc.: C (47.72), H (7.21), N (5.57); found: C (47.42); H (7.20), N (5.61).

(b) 5-Morpholino-5-desoxy-1.4;3.6-dianhydro-L-iditol 2-nitrate:

3.7 g. (17 mmol) of the previously obtained 5-morpholino-5-desoxy-1.4;3.6-dianhydro-L-iditol are esterified with nitric acid analogously to Example 14 (b), after working up converted into the hydrochloride and recrystallised from isopropanol. One obtains 2.5 g. (8.4 mmol) 5-morpholino-5-desoxy-1.4;3.6-dianhydro-L-iditol 2-nitrate hydrochloride.

M.p. 195°–6° (decomp.); $[\alpha]_D^{25}$ 46.5 (c 0.51; water)

Elementary analysis: $C_{10}H_{16}N_2O_6 \times HCL$ (296.71); calc.: C (40.48), H (5.78), N (9.44), Cl (11.95); found: C (40.51), H (5.75), N (9.44), Cl (12.1)

Example No. 17

5-(4-Methylpiperazino)-5-desoxy-1.4;3.6-dianhydro-L-iditol 2-nitrate:

(a) 5-(4-Methylpiperazino)-5-desoxy-1.4;3.6-dianhydro-L-iditol:

A mixture of 11.2 g (50 mmol) 1.4;3.6-dianhydro-D-glucitol 5-methanesulphonate and 15 g. (150 mmol) N-methylpiperazine is stirred under an atmosphere of nitrogen at 150° for 24 hrs. in a steel autoclave. After cooling, one adds thereto a solution of 2.0 g. (50 mmol) sodium hydroxide in 100 ml. n-butanol and evaporates to dryness under reduced pressure. The oily residue is treated with 500 ml. chloroform and filtered off from insolubles (sodium methanesulphonate). The chloroform phase is extracted 2 times with 200 ml. amounts of water; the combined aqueous phases give the crude base after evaporation in vacuo and azeotropic drying with ethanol and chloroform. This is dissolved in 50 ml. glacial acetic acid and converted into the dihydrogen nitrate by the addition of double the molar amount of dilute nitric acid, the greater part of which crystallises out directly. Residual product is precipitated out with ether. Recrystallisation from isopropanol/ethanol gives 8.9 g. (25 mmol) 5-(4-methylpiperazino)-5-desoxy-1.4;3.6-dianhydro-L-iditol dihydrogen nitrate.

M.p. 124°–5° (decomp.); $[\alpha]_D^{25}$ 27.9 (c 0.5; water)

Elementary analysis: $C_{11}H_{20}N_2O_3 \times 2HNO_3$ (354.32); calc.: C (37.29), H (6.26), N (15.81); found: C (37.10), H (6.36), N (15.54).

(b) 5-(4-Methylpiperazino)-5-desoxy-1.4;3.6-dianhydro-L-iditol 2-nitrate:

To a mixture of 5.82 g. (16 mmol) of the previously obtained dihydrogen nitrate, 1.0 g. (16.6 mmol) urea and 40 ml. glacial acetic acid, one allows to drop in, with stirring and cooling to 10°, first a solution of 2.6 ml. (59 mmol) 96% nitric acid (d=1.5) in 20 ml. glacial acetic acid and subsequently 20 ml. acetic anhydride and further stirs overnight at 10°. For the complete precipitating out of the product, one adds ether/petroleum ether to the suspension, decants, and dissolves the precipitate in about 200 ml. water. One adds thereto sodium hydrogen carbonate up to pH=about 6. After stirring for ½ hr., one extracts 3 times with 150 ml. amounts of chloroform, washes the combined chloroform phases with 100 ml. water, dries over anhydrous sodium sulphate/sodium carbonate, concentrates under reduced pressure and converts into the dihydrochloride by the addition of 33 ml. 1 molar HCl. After evaporation under reduced pressure and recrystallisation from isopropanol, one obtains 3.2 g. (9.2 mmol) 5-(4-methylpiperazino)-5-desoxy-1.4;3.6-dianhydro-L-iditol 2-nitrate dihydrochloride.

M.p. 201°–9° (decomp.); $[\alpha]_D^{25}$ 32.7 (c 0.53; water)

Elementary analysis: $C_{11}H_{19}N_3O_5 \times 2$ HCl (346.22); calc.: C (38.16), H (6.11), N (12.14), Cl (20.48); found: C (38.08), H (6.30), N (12.02), Cl (19.9).

Example No. 18

5-Pyridoxylideneamino-5-desoxy-1.4;3.6-dianhydro-L-iditol 2-nitrate:

A solution of 1.2 g. (30 mmol) sodium hydroxide in 80 ml. ethanol is successively mixed with 6.1 g. (30 mmol) pyridoxal hydrochloride, 5.7 g. (30 mmol) 5-amino-5-desoxy-1.4;3.6-dianhydro-L-iditol 2-nitrate (dissolved in 20 ml. ethanol) and 100 ml. benzene and heated to the boil. One distils off the azeotrope of benzene/ethanol/water (b.p.=64.9°), whereby the reaction volume is kept constant. As soon as the boiling temperature has increased to 68° (azeotrope of ethanol/benzene), one cools, filters off with suction from sodium chloride, evaporates the filtrate under reduced pressure and obtains 10 g. (29.5 mmol) of oily crude product. For further purification, one extracts the crude product with ether, dissolves the evaporated ether extract in a little benzene, dilutes with about the 20 fold amount of ether and carefully precipitates with petroleum ether. One obtains 7.1 g. (21 mmol) of crystalline 5-pyridoxylideneamino-5-desoxy-1.4;3.6-dianhydro-L-iditol 2-nitrate.

M.p. 123°–6°; $[\alpha]_D^{25}$ 140.5 (c 0.2; chloroform)

Elementary analysis: $C_{14}H_{17}N_3O_7$ (339.32); calc.: C (49.56), H (5.05), N (12.38); found: C (49.28), H (4.95), N (12.16).

Example No. 19

5-(N-Benzyl-N-methylamino)-5-desoxy-1.4;3.6-dianhydro-L-iditol 2-nitrate:

A solution of 4.1 g. (20 mmol) 5-methylamino-5-desoxy-1.4;3.6-dianhydro-L-iditol 2-nitrate (preparation see Example 9 b) in 50 ml. ethanol is mixed with 2.5 ml. (21 mmol) benzyl chloride and heated under reflux for 2 hrs. One allows to cool, adds thereto 800 mg. (20 mmol) sodium hydroxide and again heats under reflux for 2 hrs. Evaporation under reduced pressure, extraction of the residue with dichloromethane, addition of 20 mmol ethanolic hydrogen chloride solution, renewed evaporation and recrystallisation from isopropanol gives 4.1 g. (12.4 mmol) 5-(n-benzyl-N-methylamino)-5-desoxy-1,4;3.6-dianhydro-L-iditol 2-nitrate hydrochloride.

M.p. 170°–3°; $[\alpha]_D^{25}$ 39.2 (c 1; water)

Elementary analysis: $C_{14}H_{18}N_2O_5 \times HCl$ (330.77); calc.: C (50.84), H (5.79), N (8.47), Cl (10.72); found: C (50.03), H (5.77), N (8.25), Cl (11.2).

Example No. 20

5-[N-(2-Phenylethyl)-N-methylamino]-5-desoxy-1.4;3.6-dianhydro-L-iditol 2-nitrate:

A mixture of 10 g. (49 mmol) 5-methylamino-5-desoxy-1.4;3.6-dianhydro-L-iditol 2-nitrate, 50 ml. ethanol and 3.0 ml. (20 mmol) 2-phenylethyl bromide is heated under reflux for 14 hrs. and evaporated under reduced pressure. The residue is partitioned between 50 ml. chloroform and 30 ml. water. The separated chloroform phase is freed from excess starting amine by two extractions with 25 ml. amounts of 0.2 molar hydrochloric acid, after drying over anhydrous sodium sulphate, evaporated under reduced pressure, converted into the hydrochloride in ethanolic solution with 20 mmol hydrochloric acid and recrystallised from ethanol. One obtains 4.1 g. (12 mmol) 5-[N-(2-phenylethyl)-N-methylamino]-5-desoxy-1.4;3.6-dianhydro-L-iditol 2-nitrate hydrochloride.

M.p. 165°–9°; $[\alpha]_D^{25}$ 35.2 (c 0.4; water)

Elementary analysis: $C_{15}H_{20}N_2O_5$ (344.80); calc. C (52.25), H (6.14), N (8.12), Cl (10.28); found C (52.18), H (6.28), N (7.58), Cl (10.7).

Example No. 21

5-[N-Methyl-N-(3-phenylpropyl)-amino]-5-desoxy-1.4;3.6-dianhydro-L-iditol 2-nitrate:

Preparation analogously to Example 20 by the reaction of 49 mmol 5-methylamino-5-desoxy-1.4;3.6-dianhydro-L-iditol 2-nitrate with 20 mmol 3-phenyl-1-bromopropane in ethanol. Isolation as hydrochloride. Yield, after recrystallisation from isopropanol/ethanol: 5.2 g. (14.5 mmol).

M.p. 142°-5°; $[\alpha]_D^{25}$ 32.2 (c 0.4; water)

Elementary analysis: $C_{16}H_{22}N_2O_5 \times HCl$ (358.82); calc.: C (53.56), H (6.46), N (7.81), Cl (9.88); found: C (53.33), H (6.62), N (7.65), Cl (10.3).

Example No. 22

5-[N-(4-Phenylbutyl)-N-methylamino]-5-desoxy-1.4;3.6-dianhydro-L-iditol 2-nitrate:

Preparation analogously to Example 20. Isolation as hydrochloride. Yield, after recrystallisation from isopropanol: 60%.

M.p. 143°-6°; $[\alpha]_D^{25}$ 35.1 (c 1; water)

Elementary analysis: $C_{17}H_{24}N_2O_5 \times HCl$ (372.85); calc.: C (54.76), H (6.76), N (7.51), Cl (9.51); found: C (54.78), H (7.02), N (7.47), Cl (9.4).

Example No. 23

5-[N-Methyl-N-(5-phenylpentyl)-amino]-5-desoxy-1.4;3.6-dianhydro-L-iditol 2-nitrate:

Preparation analogously to Example 20. Isolation as hydrochloride. Yield, after recrystallisation from isopropanol/ether: 51%.

M.p. 114°-7°; $[\alpha]_D^{25}$ 36.2 (c 1.0; water)

Elementary analysis: $C_{18}H_{26}N_2O_5 \times HCl$ (386.88); calc.: C (55.88), H (7.04), N (7.24), Cl (9.16); found: C (55.89), H (7.20), N (7.19), Cl (9.4).

Example No. 24

5-(N-Cinnamyl-N-methylamino)-5-desoxy-1.4;3.6-dianhydro-L-iditol 2-nitrate:

Preparation analogously to Example 20 by the reaction of 5-methylamino-5-desoxy-1.4;3.6-dianhydro-L-iditol 2-nitrate with 3-phenyl-1-bromo-2-propene. Isolation as hydrochloride.

M.p. 155°-7° (recryst. from isopropanol) $[\alpha]_D^{25}$ 23.2 (c 0.44; water)

Elementary analysis: $C_{16}H_{20}N_2O_5 \times HCl$ (356.81); calc.: C (53.86), H (5.93), N (7.85), Cl (9.94); found: C (53.91), H (6.05), N (7.64), Cl (9.9).

Example No. 25

5-Benzylamino-5-desoxy-1.4;3.6-dianhydro-L-iditol 2-nitrate:

A mixture of 15.2 g. (80 mmol) 5-amino-5-desoxy-1.4;3.6-dianhydro-L-iditol 2-nitrate (preparation see Example 1 c), 70 ml. ethanol and 3.6 ml. (30 mmol) benzyl bromide is boiled under reflux for 5 hrs. After cooling, one filters off with suction from excess starting amine hydrobromide which has crystallised out, evaporates the filtrate under reduced pressure, dissolves the residue in 60 ml. chloroform and extracts the product with 0.5 molar hydrochloric acid. The hydrochloric acid phases are brought to pH=8 to 9 with dilute aqueous sodium hydroxide solution and the product re-extracted with chloroform. The chloroform extract is, after evaporation, converted into the hydrochloride with 30 mmol hydrochloric acid and recrystallised from methanol/isopropanol. One obtains 6.0 g. (18.9 mmol) 5-benzylamino-5-desoxy-1.4;3.5-dianhydro-L-iditol 2-nitrate hydrochloride.

M.p. 171°-5° (decomp.); $[\alpha]_D^{25}$ 51.2 Z(c 0.4; water)

Elementary analysis: $C_{13}H_{16}N_2O_5 \times HCl$ (316.74); calc.: C (49.30), H (5.41), N (8.84), Cl (11.19); found: C (49.28), H (5.42), N (8.87), Cl (11.3).

Example No. 26

5-Diphenylmethylamino-5-desoxy-1.4;3.6-dianhydro-L-iditol 2-nitrate:

A mixture of 5.7 g. (30 mmol) 5-amino-5-desoxy-1.4;3.6-dianhydro-L-iditol 2-nitrate, 40 ml. dimethylformamide and 3.9 g. (15 mmol) bromodiphenylmethane is stirred for 2 days at 80° C. After cooling, one adjusts to pH=8-9 by the addition of 640 mg. (16 mmol) sodium hydroxide and evaporates under reduced pressure. The residue is extracted hot with dichloromethane, the extract is saturated with hydrogen chloride, again evaporated under reduced pressure and extracted hot with toluene. The toluene extract is washed several times with water and evaporated under reduced pressure. One obtains 2.5 g. (6.4 mmol) 5-diphenylmethylamino-5-desoxy-1.4;3.6-dianhydro-L-iditol 2-nitrate hydrochloride. One reprecipitates the analytical sample from dichloromethane with ether/petroleum ether.

M.p. 189°-195° (decomp.); $[\alpha]_D^{25}$ 78.3 (c 1; chloroform)

Elementary analysis: $C_{19}H_{20}N_2O_5 \times HCl$ (392.84); calc.: C (58.09), H (5.39), N (7.13), Cl (9.02); found: C (57.91), H (5.44), N (7.08), Cl (8.8).

Example No. 27

5-(2-Phenylethylamino)-5-desoxy-1.4;3.6-dianhydro-L-iditol 2-nitrate:

Preparation analogously to Example 25. Isolation as hydrochloride. Yield: 53%. M.p. 185° (decomp.) (after recrystallisation from water). $[\alpha]_D^{25}$ 48.6 (c 0.21; water)

Elementary analysis: $C_{14}H_{18}N_2O_5 \times HCl$ (330.77); calc.: C (50.84), H (5.79), N (8.47), Cl (10.72); found: C (50.54), H (5.76), N (8.46), Cl (10.3).

Example No. 28

5-(3-Phenylpropylamino)-5-desoxy-1.4;3.6-dianhydro-L-iditol 2-nitrate:

Preparation analogously to Example 25. Isolation as hydrochloride. Yield, after recrystallisation from methanol/water: 49%. M.p. 174° (decomp.); $[\alpha]_D^{25}$ 48.8 (c 0.5; methanol).

Elementary analysis: $C_{15}H_{20}N_2O_5 \times HCl$ (344.80); calc.: C (52.25), H (6.14), N (8.12), Cl (10.28); found: C (52.42), H (6.50), N (7.90), cl (10.7).

Example No. 29

5-(4-Phenylbutylamino)-5-desoxy-1.4;3.6-dianhydro-L-iditol 2-nitrate:

A mixture of 6 g. (75 mmol) 4-phenyl-1-bromobutane, 250 ml. ethanol and 35 g. (184 mmol) 5-amino-5-desoxy-1.4;3.6-dianhydro-L-iditol 2-nitrate is boiled under reflux for 24 hrs. After cooling, one filters off excess starting amine hydrobromide with suction, then washes the precipitate with dichloromethane, concentrates the filtrate under reduced pressure, mixes the residue with 200 ml. dichloromethane and extracts starting amine still contained therein 2 times with 50 ml. amounts of 5% acetic acid. After washing with 50 ml. 1 molar aqueous sodium hydroxide solution, drying over anhydrous sodium sulphate and evaporation under reduced pressure, one obtains from the dichloromethane phase 21.5 g. (67 mmol) of crude product which is dissolved in 100 ml. ethanol, mixed with 68 mmol hydrochloric acid and again evaporated under reduced pressure. Two recrystallisations from ethanol with the addition of active charcoal gives 10.3 g. (29 mmol) 5-(4-phenyl-butylamino)-5-desoxy-1.4;3.6-dianhydro-L-iditol 2-nitrate hydrochloride.

M.p. 166°–8°; $[\alpha]_D^{25}$ 41.6 (c 0.39; water)

Elementary analysis: $C_{16}H_{22}N_2O_5 \text{xHCl}$ (358.82);calc.: C (53.56), H (6.46), N (7.81), Cl (9.88); found: C (53.48), H (6.51), N (7.89), Cl (10.1).

Example No. 30

5-(5-Phenylpentylamino)-5-desoxy-1.4;3.6-dianhydro-L-iditol 2-nitrate:

Preparation analogously to Example 29. Isolation as hydrochloride. Yield, after recrystallisation from water (with the addition of active charcoal): 37%.

M.p. 146°–8°; $[\alpha]_D^{25}$ 41.1 (c 0.3; water)

Elementary analysis: $C_{17}H_{24}N_2O_5 \text{xHCl}$ (372.85); calc.: C (54.76), H (6.76), N (7.51), Cl (9.51); found: C (54.88), H (6.91), N (7.40), Cl (9.6).

Example No. 31

5-[3-(3,4-Dimethoxyphenyl)-propylamino]-5-desoxy-1.4;3.6-dianhydro-L-iditol 2-nitrate:

(a) 3-(3,4-Dimethoxyphenyl)-propyl-1-methanesulphonate:

To a mixture of 10 g. (50 mmol) 3-(3,4-dimethoxyphenyl)-1-propanol, 50 ml. chloroform and 14 ml. (100 mmol) triethylamine there is added dropwise, with stirring, exclusion of moisture and cooling to −15°, a solution of 5.5 ml. (70 mmol) methanesulphonic acid chloride in 20 ml. chloroform. Subsequently, one stirs for 2 hrs. in a cold bath, allows it to come to room temperature and pours the batch on to a mixture of 100 ml. ice water and 3 ml. 37% hydrochloric acid. One stirs up well, separates off the chloroform phase, washes it with 20 ml. water and 20 ml. aqueous sodium hydrogen carbonate solution, dries over anhydrous sodium sulphate and evaporates under reduced pressure. One obtains the 3-(3,4-dimethoxyphenyl)-propyl-1-methane sulphonate in quantitative yield (14 g.) in the form of a yellowish oil.

(b) 5-[3-(3,4-Dimethoxyphenyl)-propylamino]-5-desoxy-1.4;3.6-dianhydro-L-iditol 2-nitrate:

11 g. (40 mmol) of the previously obtained oil are, together with 80 ml. ethanol and 19 g. (100 mmol) 5-amino-5-desoxy-1.4;3.6-dianhydro-L-iditol 2-nitrate, heated under reflux for 12 hrs. and then evaporated under reduced pressure. The residue is taken up in 80 ml. chloroform, whereby excess starting amine remains undissolved as hydrogen methanesulphonate. After suction-filtration and washing with chloroform, one frees the filtrate from further starting amine by successive extraction 2 times with 40 ml. amounts of water and 5 times with 20 ml. amounts of 0.2 molar acetic acid. One washes with dilute aqueous sodium hydroxide solution, dries the chloroform phase over anhydrous sodium sulphate, evaporates under reduced pressure, dissolves the so obtained crude base in ethanol, adds 40 mmol hydrochloric acid thereto and again evaporates. One obtains 10.8 g. (26.7 mmol) 5-[3-(3,4-dimethoxyphenyl)-propylamino]-5-desoxy-1.4;3.6-dianhydro-L-iditol 2-nitrate hydrochloride. Recrystallisation from ethanol with the addition of active charcoal gives 5.7 g. (14.1 mmol) of pure product.

M.p. 160°–163°; $[\alpha]_D^{25}$ 41.3 (c 0.33; methanol)

Elementary analysis: $C_{17}H_{24}N_2O_7 \text{xHCl}$ (404.85); calc.: C (50.44), H (6.22), N (6.92), Cl (8.76); found: C (50.51), H (6.37), N (6.89), Cl (9.1).

Example No. 32

5-[4-(4-Methoxyphenyl)-butylamino]-5-desoxy-1.4;3.6-dianhydro-L-iditol 2-nitrate:

Preparation analogously to Example 31 a, b. 5 g. (28 mmol) 4-(4-Methoxyphenyl)-1-butanol give, after reaction with methanesulphonic acid chloride, 7.2 g. (28 mmol) oily 4-(4-methoxyphenyl)-butyl 1-methanesulphonate. This, reacted with 14.3 g. (75 mmol) 5-amino-5-desoxy-1.4;3.6-dianhydro-L-iditol 2-nitrate, gives 6.7 g. (19 mmol) of crude base. After conversion into the hydrochloride and recrystallisation from ethanol, one obtains 2.8 g. (7.2 mmol) 5-[4-(4-methoxyphenyl)-butylamino]-1.4;3.6-dianhydro-L-iditol 2-nitrate hydrochloride.

M.p. 182°–4°; $[\alpha]_D^{25}$ 38 (c 0.2; water)

Elementary analysis: $C_{17}H_{24}N_2O_6 \text{xHCl}$ (388.85); calc.: C (52.51), H (6.48), N (7.20), Cl (9.12); found: C (52.24), H (6.44), N (7.02), Cl (9.3).

Example No. 33

5-[N-(2-Phenoxyethyl)-N-methylamino]-5-desoxy-1.4;3.6-dianhydro-L-iditol 2-nitrate:

Preparation analogously to Example 20 by the reaction of excess 5-methylamino-5-desoxy-1.4;3.6-dianhydro-L-iditol 2-nitrate with 2-phenoxy-1-bromoethane. Isolation as hydrochloride. Recrystallisation from ethanol/isopropanol.

M.p. 153°–6°; $[\alpha]_D^{25}$ 43.4; (c 0.5; water)

Elementary analysis: $C_{15}H_{20}N_2O_6 \text{xHCl}$ (360.80); calc.: C (49.94), H (5.97), N (7.76), Cl (9.83); found: C (50.27), H (6.06), N (7.51), Cl (10.1).

Example No. 34

5-[N-Methyl-N-(3-phenoxypropyl)-amino]-5-desoxy-1.4;3.6-dianhydro-L-iditol 2-nitrate:

Preparation analogously to Example 20 by the reaction of excess 5-methylamino-1.4;3.6-dianhydro-L-iditol 2-nitrate with 3-phenoxy-L-bromopropane. Isolation as hydrochloride. Recrystallisation from isopropanol/ethanol.

M.p. 132°–4°; $[\alpha]_D^{25}$ 35.5 (c 0.95; water)

Elementary analysis: $C_{16}H_{22}N_2O_6 \text{xHCl}$ (374.82); calc.: C (51.27), H (6.18), N (7.47), Cl (9.46); found: C (51.03), H (6.30), N (7.24), Cl (9.3).

Example No. 35

5-(2-Phenoxyethylamino)-5-desoxy-1.4;3.6-dianhydro-L-iditol 2-nitrate;

A mixture of 14.1 g. (70 mmol) 2-phenoxy-1-bromoethane, 250 ml. ethanol and 32 g. (168 mmol) 5-amino-5-desoxy-1.4;3.6-dianhydro-L-iditol 2-nitrate is boiled under reflux for 24 hrs. After cooling, one filters off with suction excess starting amine hydrobromide, then washes with chloroform, evaporates the filtrate under reduced pressure, takes up the residue in 80 ml. chloroform and recovers further starting amine by 4 fold extraction with 50 ml. amounts of water and 3 times with 35 ml. amounts of 0.2 molar acetic acid. The monosubstitution product is extracted from the chloroform phase by repeated extraction with 0.5 molar hydrochloric acid (in all 120 ml.), whereby it partly crystallises out in the form of the hydrochloride. Evaporation of the hydrochloric acid extracts gives further hydrochloride. After recrystallisation from methanol, one obtains 11.9 g. (34.3 mmol) 5-(2-phenoxyethylamino)-5-desoxy-1.4;3.6-dianhydro-L-iditol 2-nitrate hydrochloride.

M.p. 182°–6° (decomp.); $[\alpha]_D^{25}$ 50.7 (c 0.41; water)

Elementary analysis: $C_{14}H_{18}N_2O_6 \cdot xHCl$ (346.77); calc.: C (48.49), H (5.52), N (8.08), Cl (10.22); found: C (48.57), H (5.63), N (8.04), Cl (10.8).

Example No. 36

5-(3-Phenoxypropylamino)-5-desoxy-1.4;3.6-dianhydro-L-iditol 2-nitrate:

Preparation analogously to Example 35. Isolation as hydrochloride. Yield, after recrystallisation from methanol/water: 60.7%.

M.p. 205°–7° (decomp.); $[\alpha]_D^{25}$ 42.8 (c 0.5; water)

Elementary analysis: $C_{15}H_{20}N_2O_6 \cdot xHCl$ (360.80); calc.: C (49.94), H (5.87), N (7.76), Cl (9.83); found: C (49.88), H (5.90), N (7.62), Cl (10.0).

Example No. 37

5-(4-Phenoxybutylamino)-5-desoxy-1.4;3.6-dianhydro-L-iditol 2-nitrate:

Preparation analogously to Example 35. Isolation as hydrochloride. Yield, after recrystallisation from water: 48.4%.

M.p. 162°–5° (decomp.); $[\alpha]_D^{25}$ 41.7 (c 0.42; water)

Elementary analysis: $C_{16}H_{22}N_2O_6 \cdot xHCl$ (374.82); calc.: C (51.27), H (6.18), N (7.47), Cl (9.46); found: C (51.74), H (6.35), N (7.56), Cl (9.6).

Example No. 38

5-(5-Phenoxypentylamino)-5-desoxy-1.4;3.6-dianhydro-L-iditol 2-nitrate:

(a) 5-Phenoxy-1-bromopentane:

To a solution of 3.5 g. (0.15 mol) sodium in 100 ml. anhydrous ethanol, one adds 14.1 g. (0.15 mol) phenol, boils for 5 min. under reflux and, after cooling to 40°–50°, rapidly adds 100 ml. (0.73 mol) 1,5-dibromopentane thereto. Subsequently, one boils under reflux for 5 hrs., after cooling filters off with suction from sodium bromide, strips off the solvent under reduced pressure, adds 50 ml. chloroform thereto and extracts the solution 4 times with 30 ml. amounts of 1 molar aqueous sodium hydroxide solution. One washes once with 50 ml. water, distils off the chloroform and fractionates over a Vigreux column under water pump vacuum. At 94° (11 mm.Hg), 99 g. (0.43 mol) 1,5-dibromopentane distil over. The intermediate runnings at 94°–160° are discarded. Between 160° and 170° (10–12 mm.Hg), 22.3 g. (0.092 mol) 5-phenoxy-1-bromopentane distil over.

(b) 5-(5-Phenoxypentylamino)-5-desoxy-1.4;3.6-dianhydro-L-iditol 2-nitrate:

A mixture of 14.6 g. (60 mmol) of the previously obtained 5-phenoxy-1-bromopentane, 200 ml. ethanol and 28.5 g. (150 mmol) 5-amino-5-desoxy-1.4;3.6-dianhydro-L-iditol 2-nitrate is boiled under reflux for 24 hrs. After cooling, one filters off with suction from precipitate, boils it out with chloroform, combines the chloroform extract and filtrate and evaporates under reduced pressure. The solution of the residue in 200 ml. chloroform is, for the recovery of excess starting amine, extracted 2 times with 100 ml. amounts of water and 4 times with 30 ml. amounts of 0.3 molar acetic acid. The chloroform phase gives, after washing with 30 ml. 1 molar aqueous sodium hydroxide solution and evaporation under reduced pressure, 18.3 g. (52 mmol) of crude product, which is dissolved in ethanol, mixed with 52 ml. 1 molar hydrochloric acid, again evaporated and recrystallised from isopropanol. One obtains 13.3 g. (34.2 mmol) 5-(5-phenoxypentylamino)-5-desoxy-1.4;3.6-dianhydro-L-iditol 2-nitrate hydrochloride.

M.p. 129°–131°; $[\alpha]_D^{25}$ 40.2 (c 0.41; water)

Elementary analysis: $C_{17}H_{24}N_2O_6 \cdot xHCl$ (388.85); calc.: C (52.51), H (6.48), N (7.20), Cl (9.12); found: C (52.44), H (6.69), N (7.08), Cl (9.6).

Example No. 39

5-(6-Phenoxyhexylamino)-5-desoxy-1.4;3.6-dianhydro-L-iditol 2-nitrate:

Preparation analogously to Example 38 by the reaction of sodium phenolate with 1,6-dibromohexane to give 6-phenoxy-1-bromohexane (b.p.$_{11}$ = 172°–5°; yield 77%), which is reacted with excess 5-amino-5-desoxy-1.4;3.6-dianhydro-L-iditol 2-nitrate. Isolation as hydrochloride. Yield, after recrystallisation from isopropanol: 53%.

M.p. 114°–6°; $[\alpha]_D^{25}$ 38.5 (c 0.39; water)

Elementary analysis: $C_{18}H_{26}N_2O_6 \cdot xHCl$ (402.88); calc.: C (53.66), H (6.76), N (6.95), Cl (8.80); found: C (53.48), H (6.96), N (6.82), Cl (9.3).

Example No. 40

5-(7-Phenoxyheptylamino)-5-desoxy-1.4;3.6-dianhydro-L-iditol 2-nitrate:

Preparation analogously to Example 38 by the reaction of sodium phenolate with 1,7-dibromohexane to give 7-phenoxybromoheptane (b.p.$_{11}$ = 184°–190°; yield 71%) which is reacted with excess 5-amino-5-desoxy-1.4;3.6-dianhydro-L-iditol 2-nitrate. Isolation as hydrochloride. Yield, after recrystallisation from ethanol/isopropanol: 59%.

M.p. 136°–8°; $[\alpha]_D^{25}$ 43.9 (c 0.3; methanol)

Elementary analysis: $C_{19}H_{28}N_2O_6 \cdot xHCl$ (416.90); calc.: C (54.74), H (7.01), N (6.72), Cl (8.50); found: C (54.78), H (7.15), N (6.66), Cl (9.5).

Example No. 41

5-(8-Phenoxyoctylamino)-5-desoxy-1.4;3.6-dianhydro-L-iditol 2-nitrate:

Preparation analogously to Example 38 by the reaction of sodium phenolate with 1,8-dibromooctane to give 8-phenoxy-1-bromooctane (b.p.$_{11}$ = 196°–202°; yield 75%) which is reacted with excess 5-amino-5-desoxy-1.4;3.6-dianhydro-L-iditol 2-nitrate. Isolation is hydrochloride. Yield, after recrystallisation from ethanol/isopropanol: 62%.

M.p. 117°–9°; $[\alpha]_D^{25}$ 35.3 (c 0.3; methanol)

Elementary analysis: $C_{20}H_{30}N_2O_6 \cdot xHCl$ (430.93); calc.: C (55.74), H (7.25), N (6.50), Cl (8.23); found: C (55.89), H (7.42), N (6.40), Cl (8.6).

Example No. 42

2-(3-Phenoxypropylamino)-2-desoxy-1.4;3.6-dianhydro-D-glucitol 5-nitrate:

A mixture of 8.8 g. (40 mmol) 98% 3-phenoxy-1-bromopropane, 130 ml. ethanol and 19 g. (100 mmol) 2-amino-2-desoxy-1.4;3.6-dianhydro-D-glucitol 5-nitrate (preparation see Example 3 c) is boiled under reflux for 24 hours and then evaporated under reduced pressure. The residue is taken up in 50 ml. chloroform and successively extracted 2 times with 50 ml. amounts of water, 3 times with 30 ml. amounts of 0.3 molar acetic acid and 5 times with 30 ml. amounts of 0.1 molar hydrochloric acid; in the case of shakings out with hydrochloric acid, a part of the product precipitates out as hydrochloride and is filtered off with suction.

The acetic acid extracts 2 and 3 are combined with the hydrochloric acid extracts, rendered alkaline with dilute aqueous sodium hydroxide solution and extracted with chloroform. The chloroform extract gives, after drying with anhydrous sodium sulphate and evaporation, 7 g. (21.7 mmol) of crude product which is converted into the hydrochoride with 22 ml. 1 molar hydrochloric acid and again evaporated. One combines with the previously obtained hydrochloride, recrystallises 2 times from ethanol and obtains 7.3 g. (20.2 mmol) 2-(3-phenoxypropylamino)-2-desoxy-1.4;3.6-dianhydro-D-glucitol 5-nitrate hydrochloride.

M.p. 165°-8° (decomp.); $[\alpha]_D^{25}$ 94.6 (c 0.43; water)

Elementary analysis: $C_{15}H_{20}N_2O_6xHCl$ (360.80); calc.: C (49.94), H (5.87), N (7.76), Cl (9.83); found: C (50.08), H (5.92), N (7.68), Cl (10.3).

Example No. 43

2-(4-Phenoxybutylamino)-2-desoxy-1.4;3.6-dianhydro-D-glucitol 5-nitrate:

A mixture of 6.5 g. (30.5 mmol) 4-phenyl-1-bromobutane, 100 ml. ethanol and 14.4 g. (76 mmol) 2-amino-2-desoxy-1.4;3.6-dianhydro-D-glucitol 5-nitrate (preparation see Example 3c) is boiled under reflux for 17 hrs. and then evaporated under reduced pressure. The residue is taken up in 50 ml. chloroform and successively extracted 2 times with 50 ml. amounts of water and 2 times with 30 ml. 0.1 molar hydrochloric acid. The aqueous and hydrochloric acid extracts are employed for the recovery of excess starting amine. The chloroform phase is washed with 50 ml. dilute aqueous sodium hydroxide solution, evaporated under reduced pressure and the residue converted into the hydrochloride by dissolving in ethanol and adding the equivalent molar amount of hydrochloric acid. Once again evaporates, recrystallises 2 times from ethanol/isopropanol and obtains 5.33 g. (14.9 mmol) 2-(4-phenylbutylamino)-2-desoxy-1.4;3.6-dianhydro-D-glucitol 5-nitrate hydrochloride.

M.p. 154°-8° (decomp.); $[\alpha]_D^{25}$ 91.4 (c 0.4; water)

Elementary analysis: $C_{16}H_{22}N_2O_5xHCl$ (358.82); calc.: C (53.56), H (6.46), N (7.81), Cl (9.88); found: C (53.64), H (6.50), N (7.87), Cl (10.2).

Example No. 44

5-[2-Hydroxy-3-(4-methoxyphenoxy)-propylamino]-5-desoxy-1.4;3.6-dianhydro-L-iditol 2-nitrate:

To a solution, boiling under reflux, of 7.6 g. (40 mmol) 5-amino-5-desoxy-1.4;3.6-dianhydro-L-iditol 2-nitrate in 50 ml. ethanol, one adds dropwise, within 2-3 hrs., a solution of 5.4 g. (30 mmol) 1,2-epoxy-3-(4-methoxyphenoxy)-propane in 50 ml. ethanol, boils under reflux for a further 24 hrs. and evaporates under reduced pressure. The solution of the residue in 50 ml. chloroform is, for the separating off of excess starting amine, extracted 3 times with 20 ml. amounts of 0.2 molar acetic acid and washed with dilute aqueous sodium hydroxide solution. Subsequently, one extracts several times with 20 ml. portions of 1 molar hydrochloric acid until all monosubstitution product has passed over into the hydrochloric acid phase. These are evaporated under reduced pressure and recrystallised from ethanol/isopropanol. One obtains 5.62 g. (13.8 mmol) 5-[2-hydroxy-3-(4-methoxyphenoxy)-propylamino]-5-desoxy-1.4;3.6-dianhydro-L-iditol 2-nitrate hydrochloride.

M.p. 174°-6° (decomp.); $[\alpha]_D^{25}$ 46.8 (c 0.98; water)

Elementary analysis: $C_{16}H_{22}N_2O_8xHCl$ (406.82); calc.: C (47.24), H (5.70), N (6.89), Cl (8.71); found: C (47.66), H (5.84), N (6.76), Cl (9.1).

The epoxide derivative used as starting product can be prepared, e.g. in the following manner:

To a mixture of 82 g. (0.66 mol) 4-methoxyphenol and 62 g. (0.67 mol) epichlorohydrin are added dropwise, with stirring at 50° C. internal temperature, within 2-3 hrs., 89 g. (0.67 mol) 30% aqueous sodium hydroxide solution. One further stirs at 50° until the reaction is completed, allows to cool, adds 200 ml. chloroform thereto, separates off the organic phase, further extracts the aqueous phase twice with 50 ml. amounts of chloroform and washes the combined chloroform phases 3 times with dilute aqueous sodium hydroxide solution. The chloroform phase is, after drying over anhydrous sodium sulphate, evaporated and the oily residue fractionally distilled in a vacuum through a Vigreux column. 63 g. (0.35 mol) 1,2-epoxy-3-(4-methoxyphenoxy)-propane distil over at 8 mm.Hg between 154° and 158°.

Example No.45

5-[2-Hydroxy-3-(3-methoxyphenoxy)-propylamino]-5-desoxy-1.4;3.6-dianhydro-L-iditol 2-nitrate:

Preparation analogously to Example 44 from 1,2-epoxy-3-(3-methoxyphenoxy)-propane (b.p.$_9$=158°-161°) and excess 5-amino-5-desoxy-1.4;3.6-dianhydro-L-iditol 2-nitrate. Isolation as hydrochloride. Yield, after recrystallisation from ethanol/isopropanol: 43%.

M.p. 172°-4° (decomp.); $[\alpha]_D^{25}$ 41.9 (c 0.4; ethanol)

Elementary analysis: $C_{16}H_{22}N_2O_8xHCl$ (406.82); calc.: C (47.24), H (5.70), N (6.89), Cl (8.71); found: C (47.46), H (5.87), N (6.70), Cl (9.2).

Example No.46

5-[2-Hydroxy-3-(2-methoxyphenoxy)-propylamino]-5-desoxy-1.4;3.6-dianhydro-L-iditol 2-nitrate:

Preparation analogously to Example 44 from 1,2-epoxy-3-(2-methoxyphenoxy)-propane (b.p.$_8$=146°-148°) and excess 5-amino-5-desoxy-1.4;3.6-dianhydro-L-iditol 2-nitrate. Isolation as hydrochloride. Yield, after reprecipitation with ether from methylene chloride: 45%.

Melting range: 80°-104°; $[\alpha]_D^{25}$ 34 (c 1; water)

Elementary analysis after drying at 60° C./0.1 mm.Hg: $C_{16}H_{22}N_2O_8xHCl$ (406.82); calc.: C (47.24), H (5.70), N (6.89), Cl (8.71); found: C (46.72), H (5.69), N (6.60), Cl (9.6).

(The analysis substance still contains about 1.5% dichloromethane).

Example No.47

5-[2-Hydroxy-3-(2-ethoxyphenoxy)-propylamino]-5-desoxy-1.4;3.6-dianhydro-L-iditol 2-nitrate:

Preparation analogously to Example 44 from 1,2-epoxy-3-(2-ethoxyphenoxy)-propane (b.p.$_{0.8}$=120°-121°) and excess 5-amino-5-desoxy-1.4;3.6-dianhydro-L-iditol 2-nitrate. Purification by column chromatography on silica gel with chloroform/methanol 95/5 as eluent. The fractions with Rf=0.62 (silica gel finished plates F 254; chloroform/methanol 9/1) are combined, evaporated under reduced pressure, converted into the hydrochloride and reprecipitated from dichloromethane with ether.

Yield 10%.

M.p. 55°; $[\alpha]_D^{25}$ 31.5 (c 1; water)

Elementary analysis after drying at 40°/1 mm.Hg C$_{17}$H$_{24}$N$_2$O$_8$xHCl (420.85); calc.: C (48.52), H (5.99), N (6.66), Cl (8.42); found: C (47.07), H (5.89), N (6.21), Cl (10.7).

(The analysis substance still contains about 3% dichloromethane).

Example No.48

5-[2-Hydroxy-5-(2-allyloxyphenoxy)-propylamino]-5-desoxy-1.4;3.6-dianhydro-L-iditol 2-nitrate:

Preparation analogously to Example 44 by the reaction of 1,2-epoxy-3-(2-allyloxyphenoxy)-propane with excess 5-amino-5-desoxy-1.4;3.6-dianhydro-L-iditol 2-nitrate. Purification by column chromatography on silica gel with chloroform/methanol 9/1 as eluent. The fractions with Rf=0.64 (silica gel finished plates F 254; chloroform/methanol 9/1) are combined and give, after evaporation, the pure product in the form of the free base. Yield: 20%.

M.p. 106°–109° (from dichloromethane/n-pentane) $[\alpha]_D^{25}$ 20 (c 0.5; ethanol)

Elementary analysis: C$_{18}$H$_{24}$N$_2$O$_8$ (396.40); calc.: C (54.54), H (6.10), N (7.07); found: C (54.96), H (6.15), N (7.04).

Example No.49

5-[2-Hydroxy-3-(2-allylphenoxy)-propylamino]-5-desoxy-1.4;3.6-dianhydro-L-iditol 2-nitrate:

Preparation analogously to Example 44 by the reaction of 1,2-epoxy-3-(2-allylphenoxy)-propane (b.p.$_{0.6}$=99°–100°) with excess 5-amino-5-desoxy-1.4;3.6-dianhydro-L-iditol 2-nitrate. Purification by column chromatography on silica gel with chloroform/methanol 9/1 as eluent. The fractions with Rf=0.62 (silica gel finished plates F 254; chloroform/methanol 9/1) give the pure product in 36% yield after evaporation under reduced pressure, conversion into the hydrochloride and two reprecipitations from chloroform with ether.

Melting range 74°–102°; $[\alpha]_D^{25}$ 24.6 (c 1; water)

Elementary analysis after drying at 60°/1 mm.Hg C$_{18}$H$_{24}$N$_2$O$_7$xHCl (416.86); calc.: C (51.86), H (6.05), N (6.72), Cl (8.50); found: C (51.23), H (6.12), N (6.28), Cl (9.1). (The analysis substance still contains about 1% chloroform).

Example No.50

5-[2-Hydroxy-3-(2-cyanophenoxy)-propylamino]-5-desoxy-1.4;3.6-dianhydro-L-iditol 2-nitrate:

Preparation analogously to Example 44 by the reaction of 1,2-epoxy-3-(2-cyanophenoxy)-propane with excess 5-amino-5-desoxy-1.4;3.6-dianhydro-L-iditol 2-nitrate. Purification by column chromatography on silica gel with chloroform/methanol 9/1 as eluent. The fractions with Rf=0.56 (silica gel finished plates F 254; chloroform/methanol 9/1) give the pure product in 33% yield after evaporation under reduced pressure, conversion into the hydrochloride and reprecipitation from chloroform with ether/petroleum ether.

Melting range 75°–107°; $[\alpha]_D^{25}$ 29.8 (c 1; water)

Elementary analysis after drying at 60°/1 mm.Hg: C$_{16}$H$_{19}$N$_3$O$_7$xHCl (401.81); calc.: C (47.83), H (5.02), N (10.46), Cl (8.82); found: C (47.04), H (5.05), N (9.79), Cl (10.5). (The analysis substance still contains about 2.2% chloroform).

Example No.51

5-[2-Hydroxy-3-(3-tolyloxy)-propylamino]-5-desoxy-1.4;3.6-dianhydro-L-iditol 2-nitrate:

Preparation analogously to Example 44 by the reaction of 1,2-epoxy-3-(3-tolyloxy)-propane (b.p.$_{10}$=129°–130°) with excess 5-amino-5-desoxy-1.4;3.6-dianhydro-L-iditol 2-nitrate. Isolation as hydrochloride. Yield, after recrystallisation from water: 36%.

M.p. 171°–5°; $[\alpha]_D^{25}$ 48.3 (c 0.52; methanol)

Elementary analysis: C$_{16}$H$_{22}$N$_2$O$_7$xHCl (390.82); calc.: C (49.17), H (5.93), N (7.17), Cl (9.07); found: C (49.59), H (6.06), N (7.62), Cl (9.5).

Example No.52

5-[2-Hydroxy-3-(3-trifluoromethylphenoxy)-propylamino]-5-desoxy-1.4;3.6-dianhydro-L-iditol 2-nitrate:

Preparation analogously to Example 44 by the reaction of 1,2-epoxy-3-(3-trifluoromethylphenoxy)-propane (b.p.$_{17}$=127°–131°) with excess 5-amino-5-desoxy-1.4;3.6-dianhydro-L-iditol 2-nitrate. Isolation as hydrochloride. Yield, after recrystallisation from methanol/chloroform: 29%.

M.p. 135°–8°; $[\alpha]_D^{25}$ 36 (c 1; methanol)

Elementary analysis: C$_{16}$H$_{19}$F$_3$N$_2$O$_7$xHCl (440.80); calc.: C (43.21), H (4.53), N (6.30), Cl (7.97), F (12.81); found: C (43.18), H (4.60), N (6.23), Cl (8.5).

Example No.53

5-[2-Hydroxy-3-(4-carbamoylmethylphenoxy)-propylamino]-5-desoxy-1.4;3.6-dianhydro-L-iditol 2-nitrate:

Preparation analogously to Example 44 by the reaction of 4-(2,3-epoxypropoxy)-phenylacetic acid amide (m.p.=169.5°–171°; from acetone) with excess 5-amino-5-desoxy-1.4;3.6-dianhydro-L-iditol 2-nitrate. Isolation as hydrochloride. Yield, after recrystallisation from ethanol/chloroform/ether: 10%.

M.p. 177°–8° (decomp.); $[\alpha]_D^{25}$ 31.3 (c 1; water)

Elementary analysis: C$_{17}$H$_{23}$N$_3$O$_8$xHCl (433.85); calc.: C (47.06), H (5.58), N (9.96), Cl (8.17); found: C (47.06), H (5.68), N (9.39), Cl (8.3).

Example No.54

5-[2-Hydroxy-3-(1-naphthyloxy)-propylamino]-5-desoxy-1.4;3.6-dianhydro-L-iditol 2-nitrate:

Preparation analogously to Example 44 by the reaction of 1,2-epoxy-3-(1-naphthyloxy)-propane (b.p.$_{11}$=190°–195°) with excess 5-amino-5-desoxy-1.4;3.6-dianhydro-L-iditol 2-nitrate. Isolation as hydrochloride. Yield, after recrystallisation from ethanol/chloroform: 49%.

M.p. 186°–190° (decomp.); $[\alpha]_D^{25}$ 41 (c 0.5; methanol)

Elementary analysis: C$_{19}$H$_{22}$N$_2$O$_7$xHCl (426.85); calc.: C (53.46), H (5.43), N (6.56), Cl (8.31); found: C (53.65), H (5.43), N (6.99), Cl (8.9).

Example No.55

5-[2-Hydroxy-3-(1-naphthyloxy)-propylamino]-5-desoxy-1.4;3.6-dianhydro-D-glucitol 2-nitrate:

Preparation analogously to Example 44 by the reaction of 1,2-epoxy-3-(1-naphthyloxy)-propane with excess 5-amino-5-desoxy-1.4;3.6-dianhydro-D-glucitol 2-nitrate (prepared according to Example 2b) in boiling n-butanol. Isolation as hydrochloride. Yield, after recrystallising twice from ethanol/chloroform: 9%.

M.p. 183°–187° (decomp.); $[\alpha]_D^{25}$ 43.7 (c 0.5; dimethylformamide).

Elementary analysis: $C_{19}H_{22}N_2O_7 \cdot xHCl$ (426.85); calc.: C (53.46), H (5.43), N (6.56), Cl (8.31); found: C (53.20), H (5.53), N (6.49), Cl (8.5).

Example No.56

5-[2-Hydroxy-3-(1-oxo-1,2,3,4-tetrahydro-5-naphthyloxy)-propylamino]-5-desoxy-1.4;3.6-dianhydro-L-iditol 2-nitrate:

Preparation analogously to Example 44 by the reaction of 5-(2,3-epoxypropoxy)-1-tetralone (m.p. 55°; from hexane) with excess 5-amino-5-desoxy-1.4;3.6-dianhydro-L-iditol 2-nitrate. Isolation as hydrochloride. Yield, after reprecipitation fro ethanol with ether: 51%.

M.p. 175°–6° (decomp.); $[\alpha]_D^{25}$ 14.8 (c 1; ethanol)

Elementary analysis: $C_{19}H_{24}N_2O_8 \cdot xHCl$ (444.87); calc.: C (51.30), H (5.66), N (6.30), Cl (7.97); found: C (50.88), H (5.79), N (6.20), Cl (8.0).

Example No.57

5-[2-Hydroxy-3-(5,6,7,8-tetrahydro-1-naphthyloxy)-propylamino]-5-desoxy-1.4;3.6-dianhydro-L-iditol 2-nitrate:

Preparation analogously to Example 44 by the reaction of 5-(2,3-epoxypropoxy)-tetralin with excess 5-amino-5-desoxy-1.4;3.6-dianhydro-L-iditol 2-nitrate. Isolation as hydrochloride. Yield, after recrystallisation from water: 46%.

M.p. 161°–4° (decomp.); $[\alpha]_D^{25}$ 22 (c 1; ethanol)

Elementary analysis: $C_{19}H_{26}N_2O_7 \cdot xHCl$ (430.89); calc.: C (52.96), H (6.32), N (6.50), Cl (8.23); found: C (52.72), H (6.55), N (6.52), Cl (8.3).

Example No.58

5-[3-(3-Trifluoromethylphenoxy)-propylamino]-5-desoxy-1.4;3.6-dianhydro-L-iditol 2-nitrate:

A mixture of 8.5 g. (30 mmol) 3-(3-trifluoromethylphenoxy)-1-bromopropane, 100 ml. ethanol and 17.1 g. (90 mmol) 5-amino-5-desoxy-1.4;3.6-dianhydro-L-iditol 2-nitrate is boiled under reflux for 20 hrs. After cooling, excess starting amine (present as hydrobromide) which has crystallised out is filtered off with suction, the filtrate is evaporated under reduced pressure, the residue is taken up in 100 ml. chloroform, washed, for the removal of residual starting amine, 2 times with 70 ml. amounts of water, once with 30 ml. 0.3 molar acetic acid, and once with 30 ml. 1 molar aqueous sodium hydroxide solution, dried over anhydrous sodium sulphate and the chloroform solution evaporated under reduced pressure. One obtains 11 g. (28 mmol) of crude base which is converted into the hydrochloride and recrystallised twice from ethanol. Yield of pure hydrochloride: 8.77 g. (20.5 mmol).

M.p. 172°–4° (decomp.); $[\alpha]_D^{25}$ 36.5 (c 0.43; water)

Elementary analysis: $C_{16}H_{19}F_3N_2O_6 \cdot xHCl$ (428.80); calc.: C (44.82), H (4.70), N (6.53), Cl (8.27); found: C (44.91), H (4.73), N (6.41), Cl (8.4).

The 3-(3-trifluoromethylphenoxy)-1-bromopropane used as starting product can be obtained in the following manner:

In 150 ml. anhydrous ethanol one dissolves 3.6 g. (157 mmol) sodium, adds thereto 24.5 g. (151 mmol) 98% 3-hydroxybenzotrifluoride, boils briefly for the complete formation of the phenolate, allows to cool to about 50°, adds 50 ml. (493 mmol) 1,3-dibromopropane thereto and boils under reflux until the reaction is complete (about 10 hrs.). After cooling and filtering off the sodium bromide, one evaporates off the ethanol under reduced pressure, adds 100 ml. dichloromethane thereto, washes out unreacted 3-hydroxybenzotrifluoride with dilute aqueous sodium hydroxide solution, dries the chloroform solution over anhydrous sodium sulphate, distils off the chloroform and fractionates the residue in a vacuum over a Vigreux column. At 10–11 mm.Hg, there distils over, between 124° and 132°, a total of 25.2 g. (89 mmol) 3-(3-trifluoromethylphenoxy)-1-bromopropane.

Example No.59

5-[3-(4-Tolyloxy)-propylamino]-5-desoxy-1.4;3.6-dianhydro-L-iditol 2-nitrate:

Preparation analogously to Example 58 by the reaction of 3-(4-tolyloxy)-1-bromopropane (b.p.$_{0.2}$=92°–4°) with excess 5-amino-5-desoxy-1.4;3.6-dianhydro-L-iditol 2-nitrate. Isolation as hydrochloride. Yield, after recrystallisation from methanol: 25%.

M.p. 202°–3° (decomp.); $[\alpha]_D^{25}$ 43.8 (c 0.4; water)

Elementary analysis: $C_{16}H_{22}N_2O_6 \cdot xHCl$ (374.82); calc.: C (51.27), H (6.18), N (7.47), Cl (9.46); found: C (51.22), H (6.19), N (7.44), Cl (9.7).

Example No.60

5-[3-(4-Fluorophenoxy)-propylamino]-5-desoxy-1.4;3.6-dianhydro-L-iditol 2-nitrate:

Preparation analogously to Example 58 by the reaction of 3-(4-fluorophenoxy)-1-bromopropane (b.p.$_{0.2}$=82°–88°) with excess 5-amino-5-desoxy-1.4;3.6-dianhydro-L-iditol 2-nitrate. Isolation as hydrochloride. Yield, after recrystallisation from methanol: 55%.

M.p. 198°–201° (decomp.); $[\alpha]_D^{25}$ 41.1 (c 0.4; water)

Elementary analysis: $C_{15}H_{19}FN_2O_6 \cdot xHCl$ (378.79); calc.: C (47.56), H (5.32), N (7.39), Cl (9.36); found: C (47.90), H (5.50), N (7.44), Cl (9.3).

Example No.61

5-[3-(1-Naphthyloxy)-propylamino]-5-desoxy-1.4;3.6-dianhydro-L-iditol 2-nitrate:

Preparation analogously to Example 58 by the reaction of 3-(1-naphthyloxy)-1-bromopropane (b.p.$_{15}$=157°) with excess 5-amino-5-desoxy-1.4;3.6-dianhydro-L-iditol 2-nitrate. Isolation as hydrochloride. Yield, after recrystallisation from methanol: 32.3%.

M.p. 192°–5° (decomp.); $[\alpha]_D^{25}$ 34.3 (c 0.18; water)

Elementary analysis: $C_{19}H_{22}N_2O_6 \cdot xHCl$ (410.85); calc.: C (55.55), H (5.64), N (6.82), Cl (8.63); found: C (55.68), H (5.72), N (6.73), Cl (9.0).

Example No. 62

5-[3-(4-Methoxyphenoxy)-propylamino]-5-desoxy-1.4;3.6-dianhydro-L-iditol 2-nitrate:

Preparation analogously to Example 58 by the reaction of 3-(4-methoxyphenoxy)-1-bromopropane with excess 5-amino-5-desoxy-1.4;3.6-dianhydro-L-iditol 2-nitrate. Isolation as hydrochloride. Yield, after recrystallisation from methanol/water: 24%.

M.p. 185°–8° (decomp.); $[\alpha]_D^{25}$ 39.2 (c 0.4; water)

Elementary analysis: $C_{16}H_{22}N_2O_7 \cdot xHCl$ (390.82); calc.: C (49.17), H (5.93), N (7.17), Cl (9.07); found: C (49.02), H (6.10), N (7.06), Cl (9.4).

Example No. 63

5-[3-(3-Methoxyphenoxy)-propylamino]-5-desoxy-1.4;3.6-dianhydro-L-iditol 2-nitrate:

Preparation analogously to Example 58 by the reaction of 3-(3-methoxyphenoxy)-1-bromopropane with excess 5-amino-5-desoxy-1.4;3.6-dianhydro-L-iditol 2-nitrate. Isolation as hydrochloride. Yield, after recrystallisation from ethanol/isopropanol: 25.7%.

M.p. 187°–191° (decomp.); $[\alpha]_D^{25}$ 39.5 (c 0.4; water)

Elementary analysis: $C_{16}H_{22}N_2O_7 \times HCl$ (390.82); calc.: C (49.17), H (5.93), N (7.17), Cl (9.07); found: C (49.15), H (6.06), N (7.05), Cl (8.9).

Example No. 64

5-[3-(2-Methoxyphenoxy)-propylamino]-5-desoxy-1.4;3.6-dianhydro-L-iditol 2-nitrate:

Preparation analogously to Example 58 by the reaction of 3-(2-methoxyphenoxy)-1-bromopropane with excess 5-amino-5-desoxy-1.4;3.6-dianhydro-L-iditol 2-nitrate. Isolation as hydrochloride. Recrystallisation from chloroform/benzene.

M.p. 130°–3°; $[\alpha]_D^{25}$ 38.5 (c 0.47; water)

Elementary analysis: $C_{16}H_{22}N_2O_7 \times HCl$ (390.82); calc.: C (49.17), H (5.93), N (7.17), Cl (9.07); found: C (49.09), H (6.00), N (7.15), Cl (9.3).

Example No. 65

5-[3-(2,6-Dimethoxyphenoxy)-propylamino]-5-desoxy-1.4;3.6-dianhydro-L-iditol 2-nitrate:

Preparation analogously to Example 58 by the reaction of 3-(2,6-dimethoxyphenoxy)-1-bromopropane (b.p.$_{0.06}$=127°–132°) with excess 5-amino-5-desoxy-1.3;4.6-dianhydro-L-iditol 2-nitrate. Isolation as hydrochloride semihydrate. Yield: 44%.

M.p. 110°–111° (from ethyl acetate/n-pentane); $[\alpha]_D^{25}$ 32.5 (c 0.2; water)

Elementary analysis: $C_{17}H_{24}N_2O_8 \times HCl \times 0.5\ H_2O$ (429.86); calc.: C (47.50), H (6.10), N (6.52), Cl (8.25); found: C (47.50), H (5.96), N (6.45), Cl (9.1).

Example No. 66

5-[3-(3,5-Dimethoxyphenoxy)-propylamino]-5-desoxy-1.4;3.6-dianhydro-L-iditol 2-nitrate:

Preparation analogously to Example 58 by the reaction of 3-(3,5-dimethoxyphenoxy)-1-bromopropane (b.p.$_{0.15}$=140°–152°) with excess 5-amino-5-desoxy-1.4;3.6-dianhydro-L-iditol 2-nitrate. Isolation as hydrochloride. Yield, after three recrystallisations from ethanol: 45%.

M.p. 186°–7° (decomp.); $[\alpha]_D^{25}$ 36.1 (c 0.4; water)

Elementary analysis: $C_{17}H_{24}N_2O_8 \times HCl$ (420.85); calc.: C (48.52), H (5.99), N (6.66), Cl (8.42); found: C (48.39), H (6.10), N (6.42), Cl (8.8).

Example No. 67

5-[3-(2,3-Dimethoxyphenoxy)-propylamino]-5-desoxy-1.4;3.6-dianhydro-L-iditol 2-nitrate:

Preparation analogously to Example 58 by the reaction of 3-(2,3-dimethoxyphenoxy)-1-bromopropane (b.p.$_{0.06}$=135°–138°) with excess 5-amino-5-desoxy-1.4;3.6-dianhydro-L-iditol 2-nitrate. Isolation as hydrochloride. Yield, after recrystallisation from ethanol/ether: 42.6%.

M.p. 144°–5° (decomp.); $[\alpha]_D^{25}$ 36.6 (c 0.4; water)

Elementary analysis: $C_{17}H_{24}N_2O_8 \times HCl$ (420.85); calc.: C (48.52), H (5.99), N (6.66), Cl (8.42); found: C (48.62), H (6.16), N (6.57), Cl (8.8).

Example No. 68

5-[3-(4-Chlorophenoxy)-propylamino]-5-desoxy-1.4;3.6-dianhydro-L-iditol 2-nitrate:

Preparation analogously to Example 58 by the reaction of 3-(4-chlorophenoxy)-1-bromopropane (b.p.$_{11}$=152°–5°) with excess 5-amino-5-desoxy-1.4;3.6-dianhydro-L-iditol 2-nitrate. Isolation as hydrochloride. Yield, after recrystallisation from ethanol/isopropanol: 63.3%.

M.p. 179°–181° (decomp.); $[\alpha]_D^{25}$ 40.1 (c 0.42; water)

Elementary analysis: $C_{15}H_{19}ClN_2O_6 \times HCl$ (395.25); calc.: C (45.58), H (5.10), N (7.09), Cl (17.94); found: C (45.57), H (5.18), N (6.91), Cl (18.3).

Example No. 69

5-[3-(2-Chlorophenoxy)-propylamino]-5-desoxy-1.4;3.6-dianhydro-L-iditol 2-nitrate:

Preparation analogously to Example 58 by the reaction of 3-(2-chlorophenoxy)-1-bromopropane (b.p.$_{0.8}$=115°–116°) with excess 5-amino-5-desoxy-1.4;3.6-dianhydro-L-iditol 2-nitrate. Isolation as hydrochloride. Yield, after recrystallisation from ethanol: 28.5%.

M.p. 154°–6°; $[\alpha]_D^{25}$ 34.8 (c 0.39; water)

Elementary analysis: $C_{15}H_{19}ClN_2O_6 \times HCl$ (395.25); calc.: C (45.58), H (5.10), N (7.09), Cl (17.94); found: C (45.61), H (5.09), N (7.00), Cl (17.5).

Example No. 70

5-[3-(3-Chlorophenoxy)-propylamino]-5-desoxy-1.4;3.6-dianhydro-L-iditol 2-nitrate:

A mixture of 8.8 g. (30 mmol) about 90% 3-(3-chlorophenoxy)-propyl 1-methanesulphonate, 17.1 g. (90 mmol) 5-amino-5-desoxy-1.4;3.6-dianhydro-L-iditol 2-nitrate and 100 ml. ethanol is boiled under reflux for 6 hrs. After cooling and evaporating under reduced pressure, one takes up in 80 ml. chloroform, filters off from insoluble starting amine hydrogen methanesulphonate (12 g.) and removes further starting amine by successive extraction of the filtrate with 50 ml. water and 3 times with 50 ml. amounts of 0.2 molar acetic acid. The remaining chloroform phase is washed with 30 ml. 1 molar aqueous sodium hydroxide solution, dried over anhydrous sodium sulphate and evaporated under reduced pressure. One obtains 9.8 g. (27 mmol) of the product, which is dissolved in ethanol and converted into the hydrochloride with 14 ml. 2 molar hydrochloric acid. After evaporation and recrystallisation from ethanol+active charcoal, one obtains 7.96 g. (20.1 mmol) pure 5-[3-(3-chlorophenoxy)-propylamino]-5-desoxy-1.4;3.6-dianhydro-L-iditol 2-nitrate hydrochloride.

M.p. 188°–190°; $[\alpha]_D^{25}$ 39.3 (c 0.42; water)

Elementary analysis: $C_{15}H_{19}ClN_2O_6 \times HCl$ (395.25); calc.: C (45.58), H (5.10), N (7.09), Cl (17.94); found: C (45.78), H (5.20), N (7.08), Cl (18.4).

One obtains the 3-(3-chlorophenoxy)-propyl 1-methanesulphonate used as starting product in the following manner:

To a solution of 37.3 g. (0.2 mol) 3-(3-chlorophenoxy)-1-propanol (obtained by the reaction of 3-chlorophenol sodium salt with 3-chloro-1-propanol in boiling ethanol; b.p.$_{0.4}$=112°–116°; yield 84%) and 42 ml. (0.3 mol) triethylamine in 150 ml. chloroform, one adds dropwise, with stirring, exclusion of moisture and cooling to −15°, a solution of 20 ml. (0.26 mol) methanesulphonic acid chloride in 50 ml. chloroform within 2 hrs., stirs for a further 2 hrs. at −10°, leaves to come to room temperature overnight and pours the reaction mixture, with stirring, into a mixture of 300 ml. ice water and 5 ml. 36% hydrochloric acid. After separating off the chloroform phase, one washes it twice with 100 ml. amounts of water and subsequently with aqueous sodium hydrogen carbonate solution to remove acid, dries over anhydrous sodium sulphate and evaporates under reduced pressure. One obtains, in practically quantitative yield (58.7 g.) 3-(3-chlorophenoxy)-propyl 1-methanesulphonate, still containing about 10% chloroform, as a slowly crystallising oil. The crystallisate has, after washing with petroleum ether and drying in a vacuum desiccator, the m.p. 36°–37°.

Example No. 71

5-[3-(3,4-Dichlorophenoxy)-propylamino]-5-desoxy-1.4;3.6-dianhydro-L-iditol 2-nitrate:

Preparation analogously to Example 70 by the reaction of 3,4-dichlorophenol sodium salt with 3-chloro-1-propanol to give 3-(3,4-dichlorophenoxy)-1-propanol (m.p. 40°–43°; yield about 90%), which is converted quantitatively into 3-(3,4-dichlorophenoxy)-propyl 1-methanesulphonate (m.p. 41°–43°) and is reacted with excess 5-amino-5-desoxy-1.4;3.6-dianhydro-L-iditol 2-nitrate in boiling ethanol. Isolation as hydrochloride. Yield, after recrystallisation from ethanol: 56%.

M.p. 175°–8°; $[\alpha]_D^{25}$ 32 (c 0.2; water)

Elementary analysis: $C_{15}H_{18}Cl_2N_2O_6 \times HCl$ (429.69); calc.: C (41.93), H (4.46), N (6.52), Cl (24.75); found: C (41.84), H (4.40), N (6.52), Cl (24.5).

Example No. 72

5-[3-(2,4-Dichlorophenoxy)-propylamino]-5-desoxy-1.4;3.6-dianhydro-L-iditol 2-nitrate:

Preparation analogously to Example 71 by the reaction of 3-(2,4-dichlorophenoxy)-propyl 1-methanesulphonate with excess 5-amino-5-desoxy-1.4;3.6-dianhydro-L-iditol 2-nitrate. Isolation as hydrochloride. Yield, after two recrystallisations from ethanol: 31.6%.

M.p. 162°–4°; $[\alpha]_D^{25}$ 32.7 (c 0.2; water)

Elementary analysis: $C_{15}H_{18}Cl_2N_2O_6 \times HCl$ (429.69); calc.: C (41.93), H (4.46), N (6.52), Cl (24.75); found: C (41.65), H (4.44), N (6.54), Cl (24.4).

Example No. 73

5-[3-(4-Acetamidophenoxy)-propylamino]-5-desoxy-1.4;3.6-dianhydro-L-iditol 2-nitrate:

Preparation analogously to Example 58 by the reaction of 3-(4-acetamidophenoxy)-1-bromopropane (m.p. 136°–7°; from ethanol/chloroform) with excess 5-amino-5-desoxy-1.4;3.6-dianhydro-L-iditol 2-nitrate. Isolation as hydrochloride with ½ mole water of crystallisation. Yield, after two recrystallisations from ethanol/methanol: 68.6%.

M.p. 186°–9° (decomp.); $[\alpha]_D^{25}$ 37.7 (c 0.4; water)

Elementary analysis: $C_{17}H_{23}N_3O_7 \times HCl \times 0.5\ H_2O$ (426.86); calc.: C (47.84), H (5.90), N (9.84), Cl (8.30); found: C (48.08), H (5.95), N (9.65), Cl (8.4).

Example No. 74

5-[3-(3-Dimethylaminophenoxy)-propylamino]-5-desoxy-1.4;3.6-dianhydro-L-iditol 2-nitrate:

Preparation analogously to Example 70 by the reaction of 3-dimethylaminophenol sodium salt with 3-chloro-1-propanol to give 3-(3-dimethylaminophenoxy)-1-propanol (b.p.$_{0.7}$=150°–5°; yield 57%), which is converted quantitatively into 3-(3-dimethylaminophenoxy)-propyl 1-methanesulphonate (oil) and is reacted with excess 5-amino-5-desoxy-1.4;3.6-dianhydro-L-iditol 2-nitrate in boiling ethanol. Isolation as hydrochloride. Yield, after recrystallisation from ethanol+active charcoal: 38.2%.

M.p. 173°–6° (decomp.); $[\alpha]_D^{25}$ 35 (c 0.41; water).

Elementary analysis: $C_{17}H_{25}N_3O_6 \times HCl$ (403.87); calc.: C (50.56), H (6.49), N (10.40), Cl (8.78); found: C (50.00), H (6.59), N (10.16), Cl (9.1).

Example No. 75

5-[3-(4-Chlorophenyl)-propylamino]-5-desoxy-1.4;3.6-dianhydro-L-iditol 2-nitrate:

A mixture of 19 g. (100 mmol) 5-amino-5-desoxy-1.4;3.6-dianhydro-L-iditol 2-nitrate, 10 g. (40 mmol) 3-(4-chlorophenyl)-propyl 1-methanesulphonate (m.p. 43°–45°; prepared by the reaction of 3-(4-chlorophenyl)-1-propanol with methanesulphonyl chloride) and 150 ml. ethanol is boiled under reflux for 20 hrs., evaporated under reduced pressure, taken up in 50 ml. chloroform, washed 3 times with 30 ml. amounts of 0.3 molar acetic acid and once with 30 ml. 1 molar aqueous sodium hydroxide solution, dried over anhydrous sodium sulphate, filtered and again evaporated under reduced pressure. The so obtained 9.4 g. (27.4 mmol) of crude base give, after conversion into the hydrochloride and two recrystallisations from ethanol, 5.08 g. 5-[3-(4-chlorophenyl)-propylamino]-5-desoxy-1.4;3.6-dianhydro-L-iditol 2-nitrate hydrochloride of the m.p. 174.5°–176° (decomp.) and $[\alpha]_D^{25}$ 41.5 (c 0.4; water).

Elementary analysis: $C_{15}H_{19}ClN_2O_5 \times HCl$ (379.25); calc.: C (47.51), H (5.32), N (7.39), Cl (18.70); found: C (47.82), H (5.48), N (7.52), Cl (18.3).

Example No. 76

5-[4-(4-Chlorophenyl)-butylamino]-5-desoxy-1.4;3.6-dianhydro-L-iditol 2-nitrate:

Preparation analogously to Example No. 75 by the reaction of 5-amino-5-desoxy-1.4;3.6-dianhydro-L-iditol 2-nitrate with 4-(4-chlorophenyl)-butyl 1-methanesulphonate. Yield, after conversion into the hydrochloride and recrystallisation from ethanol: 36%.

M.p. 173°–175°; $[\alpha]_D^{25}$ +40.0 (c 0.2; water)

Elementary analysis: $C_{16}H_{21}ClN_2O_5 \times HCl$ (393.28); calc.: C (48.87), H (5.64), N (7.12), Cl (18.03); found: C (49.08), H (5.76), N (7.48), Cl (18.2).

Example No. 77

5-Nicotinoylamino-5-desoxy-1.4;3.6-dianhydro-D-mannitol 2-nitrate:

A mixture of 2.3 g. (10 mmol) 5-amino-5-desoxy-1.4;3.6-dianhydro-D-mannitol 2-nitrate hydrochloride, 3.6 g. (20 mmol) nicotinic acid chloride hydrochloride and 50 ml. anhydrous pyridine is stirred for 16 hrs. at 60° with the exclusion of moisture. After cooling, one pours into 100 ml. ice water, adds 2.8 g. (70 mmol) sodium hydroxide thereto and stirs for 30 min. By repeated extraction with a total of 300 ml. chloroform, one extracts the reaction product, washes the chloroform phases 2 times with 100 ml. amounts of water, dries them over anhydrous sodium sulphate and evaporates in a vacuum. The so obtained 2.5 g. (8.5 mmol) of crude base (crude yield: 85%) gives, after conversion into the hydrochloride and recrystallisation from anhydrous ethanol/acetone, pure 5-nicotinoylamino-5-desoxy-1.4;3.6-dianhydro-D-mannitol 2-nitrate hydrochloride with the m.p. 162°–163° (decomp.) and $[\alpha]_D^{25}$=77.5 (c 0.4; water)

Elementary analysis: $C_{12}H_{13}N_3O_6 \times HCl$ (331.71); calc.: C (43.45), H (4.25), N (12.67), Cl (10.69); found: C (42.99), H (4.30), N (12.57), Cl (10.7).

Example No. 78

5-N-Methyl-N-nicotinoylamino-5-desoxy-1.4;3.6-dianhydro-L-iditol 2-nitrate:

Preparation anlogously to Example 77 by the reaction of 5-methylamino-5-desoxy-1.4;3.6-dianhydro-L-iditol 2-nitrate with nicotinic acid chloride hydrochloride in pyridine. Crude yield: 91%. Conversion into the hydrochloride and recrystallisation from anhydrous ethanol/acetone gives pure 5-N-methyl-N-nicotinoylamino-5-desoxy-1.4;3.6-dianhydro-L-iditol 2-nitrate hydrochloride semihydrate with the mp. 173°–175° (decomp.) and $[\alpha]_D^{20}+33.2$ (c 0.4; water).

Elementary analysis: $C_{13}H_{15}N_3O_6 \times HCl \times 0.5\ H_2O$ (354.75); calc.: C (44.01), H (4.83), N (11.84), Cl (9.99); found: C (44.18), H (4.57), N (11.82), Cl (10.4).

In the case of the investigation of the pharmacological properties of the compounds according to the invention, as comparison compounds there was always used the commercially available compounds isosorbide dinitrate (ISDN) and isosorbide mononitrate (ISMN), whereby ISMN is 1.4;3.6-dianhydro-D-glucitol 2-nitrate.

The coronary flowthrough-increasing effectiveness of the compounds according to the invention was determined on isolated guinea pig hearts (isolated hearts according to Langendorff, method according to Bunger et al., Pflüger's Archiv, 353. 317–325 (1975)). After reaching the stationary state in the 30th minute, the hearts were each perfused with 50 ml. tyrode solution with a content of test substance of, in each case, 25 μg./ml. Each test substance was tested on 3–6 hearts.

In each case, there was measured the inotropism, the flowthrough and the frequency, whereby the values given in Table I are average values of the percentage changes in comparison with the initial values. The comparison of the measured values shows that the coronary flowthrough-increasing effectiveness of the compounds according to the invention is greater than that of ISMN; the coronary flowthrough-increasing effectiveness of some substances even exceeds that of ISDN. Many of the substances according to the invention show favourable, inotropic- and frequency-lowering actions.

TABLE I

Experiments on Langendorff hearts
The values given in this Table show the percentage change with regard to the initial value

| substance | inotropism | flowthrough | frequency | remarks |
|---|---|---|---|---|
| ISDN | −8.11 | +91.54 | +2.00 | comparison compound |
| ISMN | −2.67 | +9.11 | −0.51 | comparison compound |
| 2 b | +3.33 | +25.89 | −0.31 | |
| 5 | −4.18 | +21.21 | +3.84 | |
| 10 b | +3.33 | +25.89 | −0.31 | |
| 11 b | −86.66 | +145.31 | −32.76 | |
| 12 b | −2.81 | +16.23 | +1.91 | |
| 13 b | −6.76 | +9.05 | −3.52 | |
| 14 b | −3.36 | +25.38 | −6.21 | |
| 15 b | ±0 | +33.95 | −3.46 | |
| 16 b | −1.67 | +14.71 | +2.70 | |
| 17 b | +2.26 | +25.07 | −4.16 | |
| 19 | −22.90 | +100.00 | −5.45 | |
| 20 | −49.39 | +66.94 | −23.02 | |
| 21 | −91.00 | +116.87 | −50.60 | |
| 23 | −94.00 | +156.10 | −61.00 | |
| 24 | −85.00 | +200.00 | −18.75 | |
| 25 | −15.87 | +47.76 | ±0 | |
| 27 | −37.67 | +67.24 | −5.64 | |
| 28 | −78.55 | +68.11 | −32.78 | |
| 31 b | −19.00 | +79.40 | −11.54 | |
| 34 | −65.00 | +50.00 | −47.60 | |

TABLE I-continued

Experiments on Langendorff hearts
The values given in this Table show the percentage change with regard to the initial value

| substance | inotropism | flowthrough | frequency | remarks |
|---|---|---|---|---|
| 35 | −18.20 | +34.00 | −6.78 | |
| 49 | −78.16 | +190.51 | −9.04 | |
| 51 | −25.60 | +92.41 | −6.96 | |
| 52 | −66.56 | +213.79 | −19.19 | |
| 54 | −77.85 | +274.32 | −15.42 | |
| 55 | −80.75 | +203.22 | −24.34 | |

The spasmolytic effectiveness of the compounds according to the invention was determined on isolated rat aorta preparations with noradrenaline- and potassium chloride-induced contractions (method according to Wende and Peiper, Pflüger's Archiv, 320, 133–141 (1970); and Towart and Stoepel, Naunyn-Schmiedeberg's Archives of Pharmacology, suppl. Vol., 308, R 18 (1979)).

In Table II, there are given the concentrations of the test substances which are necessary for a 50% inhibition of the spasm ($ED_{50}$ values). The spasmolytic effectivenesses of the compounds according to the invention are quite preponderantly better than those of ISMN and ISDN, especially when one takes into account the pharmacologically important ratio of the effective doses in the case of noradrenaline spasm and potassium chloride spasm.

TABLE II

| substance | Noradrenaline spasm | Potassium chloride spasm |
|---|---|---|
| ISDN | $1.30 \times 10^{-6}$ | $3.10 \times 10^{-6}$ |
| ISMN | $1.60 \times 10^{-5}$ | $2.40 \times 10^{-6}$ |
| 1 c | $5.75 \times 10^{-6}$ | $3.80 \times 10^{-5}$ |
| 2 b | $6.00 \times 10^{-6}$ | $1.10 \times 10^{-5}$ |
| 3 c | $8.00 \times 10^{-6}$ | — |
| 4 b | $9.40 \times 10^{-6}$ | $2.90 \times 10^{-4}$ |
| 5 | $4.20 \times 10^{-6}$ | $6.00 \times 10^{-6}$ |
| 6 | $2.80 \times 10^{-6}$ | $3.40 \times 10^{-5}$ |
| 7 | $3.40 \times 10^{-7}$ | $3.80 \times 10^{-6}$ |
| 8 | $4.40 \times 10^{-7}$ | $4.60 \times 10^{-6}$ |
| 9 b | $6.50 \times 10^{-6}$ | $2.10 \times 10^{-4}$ |
| 10 b | $6.00 \times 10^{-6}$ | $6.25 \times 10^{-6}$ |
| 11 b | $3.64 \times 10^{-7}$ | $7.50 \times 10^{-6}$ |
| 12 b | $5.50 \times 10^{-7}$ | $1.08 \times 10^{-5}$ |
| 13 b | $4.80 \times 10^{-7}$ | $7.00 \times 10^{-6}$ |
| 14 b | $3.80 \times 10^{-6}$ | $2.90 \times 10^{-6}$ |
| 15 b | $4.30 \times 10^{-6}$ | $2.50 \times 10^{-6}$ |
| 16 b | $3.00 \times 10^{-6}$ | $4.20 \times 10^{-6}$ |
| 17 b | $7.80 \times 10^{-7}$ | $4.30 \times 10^{-6}$ |
| 18 | $3.35 \times 10^{-6}$ | $3.00 \times 10^{-5}$ |
| 19 | $2.90 \times 10^{-6}$ | $2.30 \times 10^{-6}$ |
| 20 | $2.50 \times 10^{-6}$ | $3.60 \times 10^{-6}$ |
| 21 | $2.00 \times 10^{-8}$ | $2.90 \times 10^{-6}$ |
| 22 | $4.90 \times 10^{-8}$ | $2.60 \times 10^{-6}$ |
| 23 | $2.44 \times 10^{-8}$ | $2.65 \times 10^{-6}$ |
| 24 | $2.00 \times 10^{-7}$ | $2.50 \times 10^{-6}$ |
| 25 | $5.20 \times 10^{-7}$ | $1.33 \times 10^{-5}$ |
| 26 | $1.50 \times 10^{-5}$ | $3.50 \times 10^{-5}$ |
| 27 | $5.20 \times 10^{-7}$ | $9.50 \times 10^{-6}$ |
| 28 | $8.30 \times 10^{-8}$ | $3.10 \times 10^{-6}$ |
| 29 | $4.10 \times 10^{-8}$ | $3.05 \times 10^{-7}$ |
| 30 | $3.45 \times 10^{-8}$ | $9.50 \times 10^{-7}$ |
| 31 b | $1.88 \times 10^{-8}$ | $5.00 \times 10^{-7}$ |
| 33 | $5.25 \times 10^{-7}$ | $2.95 \times 10^{-6}$ |
| 34 | $2.10 \times 10^{-8}$ | $1.70 \times 10^{-6}$ |
| 35 | — | $4.40 \times 10^{-6}$ |
| 36 | $3.00 \times 10^{-7}$ | $9.50 \times 10^{-7}$ |
| 37 | $4.50 \times 10^{-8}$ | $6.40 \times 10^{-7}$ |
| 38 b | — | $2.60 \times 10^{-6}$ |
| 39 | — | $3.80 \times 10^{-6}$ |
| 40 | — | $9.00 \times 10^{-6}$ |
| 41 | — | $3.90 \times 10^{-6}$ |
| 42 | $3.20 \times 10^{-7}$ | $1.20 \times 10^{-5}$ |
| 43 | $4.40 \times 10^{-8}$ | $4.60 \times 10^{-7}$ |

TABLE II-continued

| substance | Noradrenaline spasm | Potassium chloride spasm |
|---|---|---|
| 44 | $2.90 \times 10^{-7}$ | $3.50 \times 10^{-6}$ |
| 45 | $3.40 \times 10^{-7}$ | $3.70 \times 10^{-6}$ |
| 46 | $2.85 \times 10^{-7}$ | $2.80 \times 10^{-6}$ |
| 47 | $2.05 \times 10^{-7}$ | $8.80 \times 10^{-6}$ |
| 48 | $2.50 \times 10^{-7}$ | $4.40 \times 10^{-6}$ |
| 49 | $1.60 \times 10^{-7}$ | $4.60 \times 10^{-7}$ |
| 50 | $2.70 \times 10^{-7}$ | $1.00 \times 10^{-5}$ |
| 51 | $1.10 \times 10^{-7}$ | $2.00 \times 10^{-6}$ |
| 52 | $1.15 \times 10^{-7}$ | $3.40 \times 10^{-7}$ |
| 53 | $1.90 \times 10^{-6}$ | $4.20 \times 10^{-6}$ |
| 54 | $3.60 \times 10^{-8}$ | $1.10 \times 10^{-6}$ |
| 55 | $3.39 \times 10^{-7}$ | $2.40 \times 10^{-6}$ |
| 56 | $1.30 \times 10^{-7}$ | $2.80 \times 10^{-6}$ |
| 57 | $2.39 \times 10^{-7}$ | $1.50 \times 10^{-6}$ |
| 58 | — | $2.40 \times 10^{-6}$ |
| 59 | — | $1.55 \times 10^{-6}$ |
| 60 | — | $6.25 \times 10^{-6}$ |
| 62 | $3.80 \times 10^{-8}$ | $9.80 \times 10^{-7}$ |
| 63 | — | $2.40 \times 10^{-6}$ |
| 64 | — | $2.90 \times 10^{-5}$ |
| 65 | — | $2.20 \times 10^{-6}$ |
| 66 | — | $2.00 \times 10^{-6}$ |
| 67 | — | $1.89 \times 10^{-6}$ |
| 68 | $2.28 \times 10^{-8}$ | $1.83 \times 10^{-7}$ |
| 70 | — | $2.18 \times 10^{-6}$ |

The blood pressure-lowering effectiveness of the compounds according to the invention was measured in comparison with ISDN and ISMN on narcotised guinea pigs after i.v. administration. The values given in Table III (1/2) show that the compounds according to the invention are all more effective than ISMN, whereby compound No. 5 possesses a stronger action than ISDN.

The inotropic and heart-circulatory effectiveness of the compounds according to the invention was determined on mongrel cats of 1.5 to 3.5 kg. body weight with intravenous administration. The animals were narcotised with a mixture of chloralose-urethane (1.2 g./kg. urethane+40 mg./kg. chloralose administration i.p.). They breathed spontaneously through a tracheal canula. The A. carotis sinistra was used in order to place a catheter tip manometer into the left heart chamber. The V. jugularis served for injection purposes. A catheter was pushed via the A. femoralis dextra into the Aorta descendans and connected to a pressure recorded (Statham P 23Db). The heart frequency was recorded with a pulse frequency measurer (film Hugo Sachs Elektronik) from the left ventricular pressure signal.

As follows from the values given in Table IV (1-6), the effectiveness of the tested compounds according to the invention is better than that of the comparison compound ISDN. In particular, all compounds show, besides the strong blood pressure lowering, favourable frequency-lowering effects and, in some cases, long-lasting lowering of inotropism.

Furthermore, these actions were determined on mongrel cats of 2.5 to 3.5 kg. body weight in the case of intraduodenal administration. The animals were narcotised with a mixture of chloralose-urethane (1.2 g/kg. urethane+40 mg./kg. chloralose administered i.p.). They breathed spontaneously through a tracheal canula. The A. carotis sinistra was used in order to place a catheter tip manometer into the left heart chamber. The V. jugularis served for injection purposes. A catheter was pushed via the A. femoralis dextra into the Aorta descendans and attached to a pressure recorder (Statham P 23 Db). The heart frequency was recorded with a pulse frequency measurer (firm Hugo Sachs Elektronik) from the left ventricular pressure signal. A duodenal loop was exposed by a laparotomy. The substances to be tested were injected directly into the lumen.

As follows from the values given in Table V, the blood pressure-lowering action of the tested compounds according to the invention is better than those of the comparison compound ISDN.

TABLE III

Blood pressure experiments on guinea pigs

| substance | dose mg/kg | blood pressure before mm.Hg | blood pressure after mm.Hg | Δ mm.Hg |
|---|---|---|---|---|
| ISDN | 0.25 | 68.70 ± 2.30 | 57.0 ± 2.10 | −11.70 |
|  | 1.00 | 66.00 ± 3.50 | 46.30 ± 0.90 | −19.70 |
|  | 2.50 | 66.70 ± 1.70 | 37.70 ± 0.90 | −29.00 |
| 2 b | 0.25 | 56.00 ± 7.91 | 50.25 ± 8.19 | −5.75 |
|  | 1.00 | 55.75 ± 6.55 | 41.50 ± 4.66 | −14.25 |
|  | 2.50 | 51.25 ± 5.17 | 31.75 ± 3.09 | −19.50 |
| 5 | 0.25 | 64.50 ± 2.75 | 54.00 ± 2.52 | −10.50 |
|  | 1.00 | 63.25 ± 2.93 | 40.50 ± 3.66 | −22.75 |
|  | 2.50 | 62.50 ± 4.00 | 30.75 ± 8.60 | −31.75 |
| 6 | 0.25 | 70.75 ± 6.36 | 63.75 ± 7.32 | −7.00 |
|  | 1.00 | 70.25 ± 6.42 | 55.75 ± 7.94 | −14.50 |
|  | 2.50 | 65.50 ± 5.32 | 47.75 ± 5.88 | −17.75 |
| 10 b | 0.25 | 43.25 ± 2.21 | 37.25 ± 2.06 | −6.00 |
|  | 1.00 | 43.25 ± 2.06 | 32.00 ± 2.04 | −11.25 |
|  | 2.50 | 42.75 ± 2.93 | 27.25 ± 1.60 | −15.50 |
| 14 b | 0.25 | 71.25 ± 0.63 | 65.75 ± 0.75 | −5.50 |
|  | 1.00 | 70.25 ± 2.46 | 56.25 ± 2.17 | −14.00 |
|  | 2.50 | 67.75 ± 3.47 | 49.25 ± 3.94 | −18.50 |
| 15 b | 0.25 | 72.00 ± 2.12 | 63.00 ± 1.83 | −9.00 |
|  | 1.00 | 71.25 ± 1.89 | 53.50 ± 1.71 | −17.75 |
|  | 2.50 | 71.00 ± 2.04 | 49.00 ± 2.48 | −23.00 |
| 16 b | 0.25 | 68.75 ± 3.07 | 59.50 ± 5.63 | −9.25 |
|  | 1.00 | 68.00 ± 2.86 | 48.25 ± 4.80 | −19.75 |
|  | 2.50 | 66.75 ± 3.20 | 43.25 ± 4.91 | −23.50 |
| 17 b | 0.25 | 63.50 ± 3.77 | 59.00 ± 2.27 | −4.50 |
|  | 1.00 | 64.00 ± 4.42 | 46.25 ± 3.07 | −17.75 |
|  | 2.50 | 61.75 ± 5.07 | 38.25 ± 4.55 | −23.50 |
| 47 | 0.25 | 47.00 ± 3.39 | 41.25 ± 2.78 | −5.75 |
|  | 1.00 | 44.50 ± 2.40 | 33.75 ± 2.02 | −10.75 |
|  | 2.50 | 39.50 ± 1.71 | 25.75 ± 1.31 | −13.75 |
| 49 | 0.25 | 45.75 ± 2.53 | 43.50 ± 3.38 | −2.25 |
|  | 1.00 | 43.00 ± 1.08 | 30.25 ± 1.70 | −12.75 |
|  | 2.50 | 42.75 ± 1.18 | 20.25 ± 1.03 | −22.50 |
| 50 | 0.25 | 55.50 ± 7.35 | 39.25 ± 6.97 | −16.25 |
|  | 1.00 | 52.50 ± 7.10 | 31.00 ± 3.94 | −21.50 |
|  | 2.50 | 50.50 ± 5.55 | 22.75 ± 1.80 | −27.75 |
| 51 | 0.25 | 66.75 ± 2.49 | 63.00 ± 2.35 | −3.75 |
|  | 1.00 | 66.00 ± 1.78 | 55.75 ± 2.36 | −10.25 |
|  | 2.50 | 65.75 ± 1.11 | 42.25 ± 1.32 | −23.50 |
| 52 | 0.25 | 65.50 ± 1.50 | 60.50 ± 1.32 | −5.00 |
|  | 1.00 | 61.00 ± 0.70 | 49.25 ± 4.37 | −11.75 |
|  | 2.50 | 56.75 ± 3.22 | 39.00 ± 4.38 | −17.75 |
| 54 | 0.25 | 67.00 ± 4.51 | 62.25 ± 8.05 | −4.75 |
|  | 1.00 | 67.25 ± 5.36 | 56.50 ± 4.97 | −10.75 |
|  | 2.50 | 68.50 ± 3.69 | 44.75 ± 4.50 | −23.75 |
| ISMN | 0.25 | 57.60 ± 3.10 | 53.90 ± 3.10 | −3.70 |
|  | 1.00 | 54.70 ± 3.80 | 48.40 ± 3.10 | −6.30 |
|  | 2.50 | 52.30 ± 4.80 | 41.40 ± 3.90 | −10.90 |

TABLE IV

| sub-stance | dose mg/kg | heart frequency before | heart frequency after | Δ | blood pressure before | blood pressure after | Δ | WD min | dp/dt before | dp/dt after | Δ | WD min |
|---|---|---|---|---|---|---|---|---|---|---|---|---|
| ISDN | 0.25 | 165.3 ± 8.0 | 171.7 ± 6.6 | +6.4 | 98.8 ± 6.1 | 81.2 ± 8.0 | −17.6 | 13.0 ± 4.5 | 7650 ± 585 | 8050 ± 1000 | +400 | — |

TABLE IV-continued

| sub-stance | dose mg/kg | heart frequency | | | blood pressure | | | WD min | dp/dt | | | WD min |
|---|---|---|---|---|---|---|---|---|---|---|---|---|
| | | before | after | Δ | before | after | Δ | | before | after | Δ | |
| | 0.50 | 167.0 ± 8.2 | 173.3 ± 5.2 | +6.3 | 95.8 ± 4.6 | 73.7 ± 5.0 | −22.2 | 16.5 ± 7.0 | 7333 ± 344 | 7667 ± 1003 | +334 | — |
| | 1.00 | 166.7 ± 9.5 | 174.3 ± 7.2 | +7.6 | 96.5 ± 3.9 | 69.2 ± 3.8 | −27.3 | 16.0 ± 3.4 | 6983 ± 367 | 7583 ± 1231 | +600 | — |
| | 2.5 | 162.0 + 8.2 | 170.7 + 5.8 | +8.7 | 92.5 + 4.4 | 60.7 + 3.5 | −31.8 | >10 | 6450 + 545 | 7567 + 1540 | +1117 | — |
| 28 | 0.25 | 225.0 ± 7.3 | 223.3 ± 5.6 | −1.7 | 101.3 ± 7.0 | 81.8 ± 7.8 | −19.5 | 3.1 ± 0.5 | 7667 + 1425 | 7400 ± 1172 | −267 | 2.7 ± 2.7 |
| | 0.50 | 228.0 ± 7.1 | 226.3 ± 6.5 | −1.7 | 104.9 ± 8.6 | 79.0 ± 8.0 | −25.9 | 5.8 ± 1.1 | 7567 + 1584 | 6567 ± 899 | −1000 | 10.7 ± 9.7 |
| | 1.00 | 228.0 ± 8.5 | 227.0 ± 7.1 | −1.0 | 109.7 ± 8.9 | 70.0 ± 8.2 | −39.7 | 12.2 ± 3.8 | 7067 + 968 | 5533 ± 835 | −1534 | 23.0 ± 7.0 |
| | 2.50 | 228.3 ± 11.0 | 206.3 ± 9.1 | −22.0 | 103.5 ± 10.2 | 53.2 ± 7.1 | −50.3 | >10 | 6667 ± 667 | 3600 ± 404 | −3067 | >10 |
| 29 | 0.25 | 209.0 ± 6.7 | 204.3 ± 5.9 | −4.7 | 106.8 ± 6.5 | 91.3 ± 8.8 | −15.5 | 3.2 ± 0.5 | 6480 ± 546 | 6000 ± 825 | −480 | 1.6 ± 1.0 |
| | 0.50 | 212.0 ± 6.2 | 204.7 ± 7.5 | −7.3 | 113.5 ± 5.3 | 91.3 ± 7.0 | −22.0 | 4.1 ± 0.6 | 7040 ± 611 | 6000 ± 654 | −1040 | 8.2 ± 5.5 |
| | 1.00 | 209.3 ± 3.5 | 197.7 ± 3.5 | −11.7 | 124.7 ± 5.6 | 90.7 ± 8.6 | −34.0 | 11.2 ± 1.5 | 7360 + 913 | 5000 ± 721 | −2360 | 25.5 ± 6.6 |
| | 2.50 | 205.0 ± 3.4 | 182.0 ± 5.8 | −23.0 | 129.5 ± 6.7 | 80.8 ± 9.0 | −48.7 | >10 | 7500 ± 807 | 3920 ± 728 | −3580 | >10 |
| 30 | 0.25 | 199.7 ± 16.8 | 198.0 ± 17.1 | −1.7 | 105.7 ± 7.4 | 88.2 ± 8.3 | −17.5 | 9.2 ± 3.1 | 9600 ± 1745 | 8340 ± 1674 | −1260 | 10.2 ± 1.9 |
| | 0.50 | 201.0 ± 19.1 | 200.3 ± 17.8 | −0.7 | 106.8 ± 8.9 | 81.8 ± 9.0 | −25.0 | 11.2 ± 3.2 | 9360 ± 1873 | 7540 ± 1571 | −1820 | 13.7 ± 4.7 |
| | 1.00 | 198.3 ± 18.2 | 196.0 ± 16.4 | −2.3 | 106.3 ± 8.6 | 73.3 ± 9.4 | −33.0 | 22.2 ± 8.4 | 8340 ± 1382 | 6160 ± 1129 | −2180 | 23.6 ± 10.1 |
| | 2.50 | 190.3 ± 19.2 | 188.3 ± 20.4 | −2.0 | 106.2 ± 10.4 | 60.3 ± 7.7 | −45.8 | >10 | 7900 ± 1505 | 5840 ± 1738 | −2060 | >10 |
| 34 | 0.25 | 180.3 ± 4.6 | 179.3 ± 3.7 | −1.0 | 95.2 ± 4.8 | 73.7 ± 4.0 | −21.5 | 4.1 ± 0.8 | 5333 + 777 | 4650 ± 660 | −683 | 2.8 ± 1.5 |
| | 0.50 | 179.0 ± 4.9 | 178.0 ± 3.9 | −1.0 | 99.0 ± 5.3 | 74.8 ± 4.6 | −24.2 | 4.2 ± 0.6 | 5500 ± 747 | 4683 ± 729 | −817 | 3,7 ± 1.6 |
| | 1.00 | 175.0 ± 6.7 | 172.0 ± 5.4 | −3.0 | 105.3 ± 5.0 | 74.5 ± 4.3 | −30.8 | 6.5 ± 1.4 | 5433 ± 786 | 4400 ± 686 | −1033 | 4.2 ± 1.9 |
| | 2.50 | 173.0 ± 6.6 | 158.0 ± 3.8 | −15.0 | 108.8 ± 5.2 | 69.2 ± 4.3 | −39.7 | >9.0 | 5300 ± 709 | 3850 ± 610 | −1450 | >6.5 ± 1.7 |
| 36 | 0.25 | 200.3 ± 4.7 | 204.3 ± 4.8 | +4.0 | 114.5 ± 7.1 | 97.7 ± 9.5 | −19.8 | 5.1 ± 0.7 | 7933 ± 556 | 7433 ± 528 | −500 | 3.3 ± 1.3 |
| | 0.50 | 204.0 ± 7.6 | 200.3 ± 5.9 | −3.7 | 112.5 ± 7.8 | 84.5 ± 8.5 | −28.0 | 8.5 ± 1.9 | 7833 ± 605 | 6650 ± 595 | −1183 | 7.9 ± 1.6 |
| | 1.00 | 202.3 ± 6.3 | 194.3 ± 7.2 | −8.0 | 116.8 ± 6.7 | 74.3 ± 5.7 | −42.5 | 14.8 ± 2.3 | 7883 ± 535 | 5467 ± 674 | −2416 | 19.0 ± 2.3 |
| | 2.50 | 197.7 ± 5.8 | 175.3 ± 7.9 | −22.4 | 120.8 ± 6.8 | 62.5 ± 3.4 | −58.3 | >10 | 7883 ± 573 | 4000 ± 732 | −3883 | 10 |
| 47 | 0.25 | 187.3 ± 6.6 | 188.7 ± 6.6 | +1.4 | 125.7 ± 5.2 | 121.7 ± 5.4 | −4.0 | 3.0 ± 1.3 | 8333 ± 741 | 7433 ± 515 | −900 | 3.7 ± 1.7 |
| | 0.50 | 195.7 ± 8.8 | 196.0 ± 0.3 | +0.3 | 125.5 ± 6.0 | 114.2 ± 5.5 | −11.3 | 5.7 ± 1.6 | 8567 ± 947 | 7150 ± 857 | −1417 | 9.5 ± 4.6 |
| | 1.00 | 192.0 ± 8.3 | 187.0 ± 10.3 | −5.0 | 125.2 ± 4.4 | 100.8 ± 4.2 | −24.3 | 8.2 ± 0.8 | 8050 ± 804 | 5067 ± 579 | −2983 | 10.9 ± 3.2 |
| | 2.50 | 192.0 ± 11.7 | 171.7 ± 10.1 | −20.3 | 124.7 ± 3.7 | 79.5 ± 6.0 | −45.2 | >9.0 | 7433 ± 535 | 2933 ± 526 | −4500 | >10 |
| 49 | 0.25 | 200.4 ± 7.0 | 201.2 ± 7.9 | +0.8 | 116.6 ± 9.4 | 113.6 ± 8.9 | −3.0 | 2.8 ± 1.4 | 7840 ± 1007 | 7360 ± 924 | −480 | 3.1 ± 1.9 |
| | 0.50 | 200.0 ± 6.4 | 202.0 ± 7.6 | +2.0 | 119.8 ± 8.8 | 110.6 ± 9.6 | −9.2 | 3.7 ± 1.4 | 7600 ± 916 | 6540 ± 736 | −1060 | 14.0 ± 5.5 |
| | 1.00 | 194.0 ± 12.3 | 188.4 ± 8.8 | −5.6 | 122.6 ± 9.8 | 105.8 ± 12.1 | −16.8 | 11.6 ± 2.3 | 6940 ± 828 | 4680 ± 840 | −2260 | >40 |
| | 2.50 | 191.2 ± 9.0 | 170.4 ± 7.0 | −20.8 | 121.6 ± 12.3 | 86.6 ± 12.8 | −35.0 | >10 | 6680 ± 1037 | 3780 ± 661 | −2900 | >10 |
| 50 | 0.25 | 190.7 ± 7.1 | 195.3 ± 5.1 | +4.6 | 121.0 ± 8.8 | 108.3 ± 10.7 | −12.7 | 8.5 ± 3.0 | 6533 ± 658 | 6033 ± 1055 | −500 | 8.2 ± 1.9 |
| | 0.50 | 192.0 + 6.8 | 195.3 + 6.3 | +3.3 | 120.2 + 8.4 | 102.2 + 11.5 | −18.0 | 9.8 + 2.7 | 6400 + 695 | 5133 + 710 | −1267 | 8.2 + 1.9 |
| | 1.00 | 191.7 ± 6.6 | 191.7 ± 6.1 | 0 | 122.0 ± 7.3 | 94.2 ± 11.7 | −27.8 | 14.8 ± 3.5 | 6267 ± 457 | 4200 ± 596 | −2067 | 14.8 ± 3.7 |
| | 2.50 | 189.0 ± 6.4 | 178.7 ± 7.3 | −10.3 | 123.3 ± 7.2 | 77.5 ± 10.8 | −45.8 | >10 | 6317 ± 322 | 2733 ± 410 | −3584 | >10 |
| 52 | 0.25 | 216.7 ± 9.3 | 216.7 ± 10.4 | 0 | 91.7 ± 7.7 | 77.2 ± 6.7 | −14.5 | 5.6 ± 1.6 | 6150 ± 737 | 5517 ± 837 | −633 | 4.2 ± 2.3 |
| | 0.50 | 217.0 ± 10.8 | 217.0 ± 11.7 | 0 | 94.7 ± 7.2 | 74.8 ± 8.0 | −19.9 | 11.7 ± 2.4 | 5983 ± 677 | 5133 ± 720 | −850 | 10.5 ± 2.7 |
| | 1.00 | 218.3 ± 11.7 | 217.7 ± 12.3 | −1.0 | 95.7 ± 10.0 | 69.2 ± 10.6 | −26.5 | 14.7 ± 2.0 | 5583 ± 628 | 4250 ± 545 | −1333 | 15.3 ± 1.8 |
| | 2.50 | 218.3 ± 12.0 | 204.0 ± 13.9 | −14.3 | 95.0 ± 11.6 | 60.5 ± 10.8 | −34.5 | >10 | 5233 ± 479 | 2733 ± 345 | −2500 | >10 |

TABLE IV-continued

| sub-stance | dose mg/kg | heart frequency before | heart frequency after | Δ | blood pressure before | blood pressure after | Δ | WD min | dp/dt before | dp/dt after | Δ | WD min |
|---|---|---|---|---|---|---|---|---|---|---|---|---|
| 54 | 0.25 | 188.7 ± 5.4 | 187.7 ± 6.0 | −1.0 | 115.2 ± 5.6 | 103.8 ± 4.3 | −11.4 | 1.9 ± 0.8 | 8783 ± 1764 | 8150 ± 1736 | −633 | 3.9 ± 2.1 |
|  | 0.50 | 187.3 ± 5.9 | 186.7 ± 6.2 | −0.7 | 117.7 ± 7.1 | 101.8 ± 4.4 | −15.9 | 3.2 ± 1.0 | 8767 ± 1879 | 6833 ± 1385 | −1934 | 7.6 ± 3.1 |
|  | 1.00 | 184.0 ± 6.4 | 172.0 ± 5.0 | −12.0 | 118.8 ± 8.4 | 91.0 ± 5.8 | −27.8 | 5.6 ± 1.3 | 8333 ± 1793 | 5050 ± 1108 | −3283 | 15.2 ± 3.9 |
|  | 2.50 | 178.3 ± 5.6 | 158.3 ± 4.3 | −20.0 | 123.3 ± 8.7 | 78.5 ± 4.8 | −44.8 | 6.4 ± 1.1 | 8000 ± 1595 | 2817 ± 520 | −5183 | >10 |
| 55 | 0.25 | 161.7 ± 16.8 | 164.7 ± 16.5 | +3.0 | 113.8 ± 6.2 | 107.0 ± 6.1 | −6.8 | 4.8 ± 1.3 | 5633 ± 863 | 5200 ± 757 | −433 | 4.2 ± 2.1 |
|  | 0.50 | 155.3 ± 17.9 | 157.3 ± 17.3 | +2.0 | 111.5 ± 6.1 | 98.8 ± 7.0 | −12.7 | 2.8 ± 0.6 | 5200 ± 759 | 4667 ± 684 | −533 | 5.2 ± 1.6 |
|  | 1.00 | 155.3 ± 18.6 | 154.0 ± 17.2 | −1.3 | 115.0 ± 7.7 | 96.8 ± 8.8 | −18.2 | 5.2 ± 1.0 | 5117 ± 745 | 4000 ± 576 | −1117 | 8.9 ± 2.8 |
|  | 2.50 | 148.0 ± 17.1 | 148.0 ± 12.5 | 0 | 120.3 ± 6.1 | 94.3 ± 7.5 | −26.0 | 6.3 ± 0.8 | 4783 ± 579 | 3517 ± 534 | −1266 | >7.8 ± 1.4 |

Tab. IV (1-6): heart frequency (min$^{-1}$), blood pressure (mm.Hg) and inotropism (mm.Hg/sec) after intravenous administration of the compounds according to the invention to cats. Average values ± standard errors from groups of 6 animals.

TABLE V

| substance + dose | time (min) after admin. | frequency min$^{-1}$ | blood pressure mm.Hg | Δ | dp/dt mm.sec | Δ |
|---|---|---|---|---|---|---|
| ISDN | 0 | 174.3 ± 9.3 | 104.3 ± 7.7 |  | 8800 ± 831 |  |
| 5 mg/kg | 10 | 179.3 ± 7.7 | 90.4 ± 12.5 | −13.9 | 8000 ± 1097 | −800 |
|  | 30 | 177.7 ± 7.7 | 91.2 ± 10.0 | −13.1 | 7667 ± 807 | −1133 |
|  | 60 | 175.0 ± 8.6 | 94.2 ± 9.2 | −10.1 | 7633 ± 743 | −1167 |
|  | 120 | 166.7 ± 9.4 | 95.0 ± 9.6 | −9.3 | 7050 ± 661 | −1750 |
| 52 | 0 | 209.6 ± 15.7 | 113.8 ± 5.8 |  | 6540 ± 631 |  |
| 5 mg/kg | 10 | 212.4 ± 13.8 | 100.4 ± 11.4 | −13.4 | 6200 ± 374 | −340 |
|  | 30 | 212.8 ± 13.1 | 95.6 ± 9.9 | −18.2 | 6120 ± 270 | −440 |
|  | 60 | 216.0 ± 12.3 | 95.8 ± 8.0 | −18.0 | 5480 ± 314 | −1060 |
|  | 120 | 214.4 ± 11.6 | 98.4 ± 9.0 | −15.4 | 5460 ± 768 | −1080 | heart frequency (min$^{-1}$), blood pressure (mm.Hg) and inotropism (mm.Hg/sec) after intraduodenal administration of ISDN or substance No. 52 to cats.
Average values ± standard errors from groups of 6 animals.

For informing examination of acute toxicity of some of the compounds according to the invention, said compounds were intravenously administered in physiological saline solution to female NMRI-albino mice in doses of 50, 100 and 200 mg/kg, respectively. The compounds were injected to at least 3 animals per dose. If no animal had yet been died following to the highest dose which was administered, no more doses of substances were tested. In case of doubt, the examination was repeated with at least 3 more animals applying the same dose.

The rate of death within 24 hours after administration was observed.

In Table VI, the determined rates of death as well as the LD$_{50}$-ranges evaluated therefrom are shown.

TABLE VI

| Compound according to example | Frequency of death with an intravenous dose of 200 mg/kg | 100 mg/kg | 50 mg/kg | Evaluated LD$_{50}$-range (mg/kg) |
|---|---|---|---|---|
| 1 c | 0/3 | — | — | >200 |
| 2 b | 0/3 | — | — | >200 |
| 6 | 0/3 | — | — | >200 |
| 12 b | 0/3 | — | — | >200 |
| 13 b | 6/6 | 0/3 | — | 100–200 |
| 14 b | ⅜ | — | — | ≧200 |
| 15 b | 6/6 | ⅜ | 0/3 | 50–100 |
| 16 b | 0/3 | — | — | >200 |
| 17 b | 0/3 | — | — | >200 |
| 19 | 6/6 | 0/3 | — | 100–200 |
| 21 | 6/6 | 3/3 | 0/3 | 50–100 |
| 22 | 6/6 | 3/3 | ⅜ | ≧50 |
| 25 | 6/6 | 0/3 | — | 100–200 |
| 28 | 3/3 | 5/6 | 0/10 | 50–100 |
| 29 | 3/3 | 5/6 | 5/6 | <50 |
| 32 | — | 10/10 | 1/10 | 50–100 |
| 35 | 3/3 | 2/6 | — | ≧100 |
| 36 | — | 5/6 | 0/3 | 50–100 |
| 37 | 3/3 | 10/10 | 3/10 | ≧50 |
| 42 | 6/6 | ⅜ | 0/3 | 50–100 |
| 43 | 6/6 | 3/3 | ⅜ | ≧50 |
| 44 | ⅜ | 0/3 | — | 100–200 |
| 46 | ⅜ | 0/3 | — | 100–200 |
| 50 | 4/6 | 0/3 | — | 100–200 |
| 51 | 6/6 | 3/3 | 0/3 | 50–100 |
| 52 | 6/6 | ⅜ | — | 100–200 |
| 58 | — | 7/12 | — | ca. 100 |
| 65 | 3/3 | 10/10 | 4/10 | ca. 50 |
| 66 | 3/3 | 2/10 | — | 100–200 |
| 67 | 3/3 | 3/3 | 0/10 | ca. 70 |

TABLE VI-continued

| Compound according to example | Frequency of death with an intravenous dose of | | | Evaluated LD$_{50}$-range (mg/kg) |
|---|---|---|---|---|
| | 200 mg/kg | 100 mg/kg | 50 mg/kg | |
| 68 | — | 4/9 | — | ca. 100 |
| 69 | — | 3/6 | 0/10 | 50–100 |
| 72 | — | 0/6 | — | >100 |
| 73 | 0/3 | 0/3 | — | >200 |

We claim:

1. Aminodesoxy-1.4;3.6-dianhydrohexitol nitrates of the general formula I,

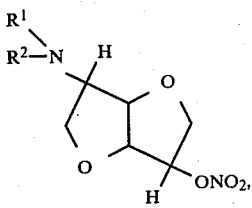

(I)

wherein $R^1$ and $R^2$, independently of one another, signify a hydrogen atom or a lower alkyl group with 1 to 4 C-atoms or wherein $R^1$ signifies a hydrogen atom or a lower alkyl group with 1 to 4 C-atoms and $R^2$ an acyl residue of an aliphatic or singly unsaturated, possibly methyl-substituted monocarboxylic acid with 2 to 8 C-atoms, a nicotinoyl, 2-O-acetylsalicoyl radical or a 1-adamantyl radical; or wherein $R^1$ signifies a hydrogen atom and $R^2$ a 2-hydroxy-3-(subst.)-phenoxyprop-1-yl radical of the general formula Ia

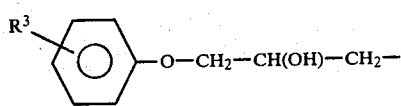

(Ia)

wherein $R^3$ signifies a hydrogen atom, a lower alkyl or lower alkenyl group with 1 to 4 C-atoms, the trifluoromethyl radical, a hydroxyl group, a lower alkoxy or lower alkenyloxy group with 1 to 4 C-atoms, a cyano group or a carbamoylmethyl radical; or wherein $R^1$ signifies a hydrogen atom and $R^2$ a 2-hydroxy-3-(α-naphthyloxy)-prop-1-yl radical, whereby the ring of the naphthalene skeleton which is not etherified with the hydroxypropyl group can be completely or partly hydrogenated or substituted by an oxo group; or wherein $R^1$ signifies a hydrogen atom or a lower alkyl group with 1 to 4 C-atoms and $R^2$ an ω-(subst.)-phenylalkyl group of the general formula Ib

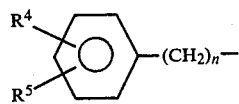

(Ib)

wherein n can be = a whole number from 1 to 6 and $R^4$ and $R^5$, in each case independently of one another, signify a hydrogen atom, a lower alkyl or alkenyl group with 1 to 4 C-atoms, the trifluoromethyl radical, a hydroxyl group, a lower alkoxy or lower alkenyloxy group with 1 to 4 C-atoms or a fluorine or chlorine atom; or wherein $R^1$ signifies a hydrogen atom or a lower alkyl group with 1 to 4 C-atoms and $R^2$ the diphenylmethyl radical or cinnamyl radical; or wherein $R^1$ signifies a hydrogen atom or a lower alkyl group with 1 to 4 C-atoms and $R^2$ an ω-(subst.)-phenoxyalkyl group of the general formula Ic

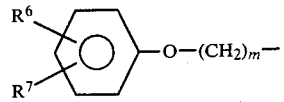

(Ic)

wherein m can be = a whole number from 2–8 and $R^6$ and $R^7$, independently of one another, signify a hydrogen atom, a lower alkyl or lower alkenyl group while 1 to 4 C-atoms, the trifluoromethyl radical, a hydroxyl group, a lower alkoxy or lower alkenyloxy group with 1 to 4 C-atoms, a fluorine or chlorine atom, the amino or acetylamino group, a mono- or di-lower alkylamino group with 1 to 4 C-atoms or $R^6$ and $R^7$, together with the phenyl radical, form the α-naphthyl radical; or wherein $R^1$ and $R^2$, together with the nitrogen atom to which they are attached, represent the residue of a cyclic, non-aromatic secondary amine with 5 to 7 ring atoms which possibly contains a furher hetero atom; or wherein $R^1$ and $R^2$ together signify a pyridoxylidene radical; as well as their pharmacologically acceptable acid-addition salts.

2. 5-Amino-5-desoxy-1.4;3.6-dianhydro-L-iditol 2-nitrates of general formula V, wherein $R^1$ and $R^2$ possess the meanings given in claim 1, as well as their pharmacologically acceptable acid-addition salts.

3. 5-Amino-5-desoxy-1.4;3.6-dianhydro-D-glucitol 2-nitrates of the general formula VI, wherein $R^1$ and $R^2$ possess the meanings given in claim 1, as well as their pharmacologically acceptable acid-addition salts.

4. 2-Amino-2-desoxy-1.4;3.6-dianhydro-D-glucitol 5-nitrates of the general formula VII, wherein $R^1$ and $R^2$ possess the meanings given in claim 1, as well as their pharmacologically acceptable acid-addition salts.

5. 5-Amino-5-desoxy-1.4;3.6-dianhydro-D-mannitol 2-nitrates of the general formula VIII, wherein $R^1$ and $R^2$ possess the meanings given in claim 1, as well as their pharmacologically acceptable acid-addition salts.

6. 5-Amino-5-desoxy-1.4;3.6-dianhydro-L-iditol 2-nitrate.

7. 5-Amino-5-desoxy-1.4;3.6-dianhydro-D-glucitol 2-nitrate.

8. 2-Amino-2-desoxy-1.4;3.6-dianhydro-D-glucitol 5-nitrate.

9. 5-Amino-5-desoxy-1.4;3.6-dianhydro-D-mannitol 2-nitrate.

10. 5-Pivaloylamino-5-desoxy-1.4;3.6-dianhydro-L-iditol 2 nitrate.

11. 5-Acetylamino-5-desoxy-1.4;3.6-dianhydro-L-iditol 2-nitrate.

12. 5-Nicotinoylamino-5-desoxy-1.4;3.6-dianhydro-L-iditol 2-nitrate.

13. 5-(2-Acetoxybenzoylamino)-5-desoxy-1.4;3.6-dianhydro-L-iditol 2-nitrate.

14. 5-Methylamino-5-desoxy-1.4;3.6-dianhydro-L-iditol 2-nitrate.

15. 5-Ethylamino-5-desoxy-1.4;3.6-dianhydro-L-iditol 2-nitrate.

16. 5-Adamant-1-ylamino-5-desoxy-1.4;3.6-dianhydro-L-iditol 2-nitrate.

17. 5-Dimethylamino-5-desoxy-1.4;3.6-dianhydro-L-iditol 2-nitrate.

18. 5-Diethylamino-5-desoxy-1.4;3.6-dianhydro-L-iditol 2-nitrate.

19. 5-Pyrrolidino-5-desoxy-1.4;3.6-dianhydro-L-iditol 2-nitrate.
20. 5-Piperidine-5-desoxy-1.4;3.6-dianhydro-L-iditol 2-nitrate.
21. 5-Morpholino-5-desoxy-1.4;3.6-dianhydro-L-iditol 2-nitrate.
22. 5-(4-Methylpiperazino)-5-desoxy-1.4;3.6-dianhydro-L-iditol 2-nitrate.
23. 5-Pyridoxylideneamino-5-desoxy-1.4;3.6-dianhydro-L-iditol 2-nitrate.
24. 5-(N-Benzyl-N-methylamino)-5-desoxy-1.4;3.6-dianhydro-L-iditol 2-nitrate.
25. 5-[N-(2-Phenylethyl)-N-methylamino]-5-desoxy-1.4;3.6-dianhydro-L-iditol 2-nitrate.
26. 5-[N-Methyl-N-(3-phenylpropyl)-amino]-5-desoxy-1.4;3.6-dianhydro-L-iditol 2-nitrate.
27. 5-[N-(4-Phenylbutyl)-N-methylamino]-5-desoxy-1.4;3.6-dianhydro-L-iditol 2-nitrate.
28. 5-[N-Methyl-N-(5-phenylpentyl)-amino]-5-desoxy-1.4;3.6-dianhydro-L-iditol 2-nitrate.
29. 5-(N-Cinnamyl-N-methylamino)-5-desoxy-1.4;3.6-dianhydro-L-iditol 2-nitrate.
30. 5-Benzylamino-5-desoxy-1.4;3.6-dianhydro-L-iditol 2-nitrate.
31. 5-Diphenylmethylamino-5-desoxy-1.4;3.6-dianhydro-L-iditol 2-nitrate.
32. 5-(2-Phenylethylamino)-5-desoxy-1.4;3.6-dianhydro-L-iditol 2-nitrate.
33. 5-(3-Phenylpropylamino)-5-desoxy-1.4;3.6-dianhydro-L-iditol 2-nitrate.
34. 5-(4-Phenylbutylamino)-5-desoxy-1.4;3.6-dianhydro-L-iditol 2-nitrate.
35. 5-(5-Phenylpentylamino)-5-desoxy-1.4;3.6-dianhydro-L-iditol 2-nitrate.
36. 5-[3-(3,4-Dimethoxyphenyl)-propylamino]-5-desoxy-1.4;3.6-dianhydro-L-iditol 2-nitrate.
37. 5-[4-(4-Methoxyphenyl)-butylamino]-5-desoxy-1.4;3.6-dianhydro-L-iditol 2-nitrate.
38. 5-[N-(2-Phenoxyethyl)-N-methylamino]-5-desoxy-1.4;3.6-dianhydro-L-iditol 2-nitrate.
39. 5-[N-Methyl-N-(3-phenoxypropyl)-amino]-5-desoxy-1.4;3.6-dianhydro-L-iditol 2-nitrate.
40. 5-(2-Phenoxyethylamino)-5-desoxy-1.4;3.6-dianhydro-L-iditol 2-nitrate.
41. 5-(3-Phenoxypropylamino)-5-desoxy-1.4;3.6-dianhydro-L-iditol 2-nitrate.
42. 5-(4-Phenoxybutylamino)-5-desoxy-1.4;3.6-dianhydro-L-iditol 2-nitrate.
43. 5-(5-Phenoxypentylamino)-5-desoxy-1.4;3.6-dianhydro-L-iditol 2-nitrate.
44. 5-(6-Phenoxyhexylamino)-5-desoxy-1.4;3.6-dianhydro-L-iditol 2-nitrate.
45. 5-(7-Phenoxyheptylamino)-5-desoxy-1.4;3.6-dianhydro-L-iditol 2-nitrate.
46. 5-(8-Phenoxyoctylamino)-5-desoxy-1.4;3.6-dianhydro-L-iditol 2-nitrate.
47. 2-(3-Phenoxypropylamino)-2-desoxy-1.4;3.6-dianhydro-D-glucitol 5-nitrate.
48. 2-(4-Phenylbutylamino)-2-desoxy-1.4;3.6-dianhydro-D-glucitol 5-nitrate.
49. 5-[2-Hydroxy-3-(4-methoxyphenoxy)-propylamino]-5-desoxy-1.4;3.6-dianhydro-L-iditol 2-nitrate.
50. 5-[2-Hydroxy-3-(3-methoxyphenoxy)-propylamino)-5-desoxy-1.4;3.6-dianhydro-L-iditol 2-nitrate.
51. 5-[2-Hydroxy-3-(2-methoxyphenoxy)-propylamino]-5-desoxy-1.4;3.6-dianhydro-L-iditol 2-nitrate.
52. 5-[2-Hydroxy-3-(2-ethoxyphenoxy)-propylamino]-5-desoxy-1.4;3.6-dianhydro-L-iditol 2-nitrate.
53. 5-[2-Hydroxy-3-(2-allyloxyphenoxy)-propylamino]-5-desoxy-1.4;3.6-dianhydro-L-iditol 2-nitrate.
54. 5-[2-Hydroxy-3-(2-allylphenoxy)-propylamino]-5-desoxy-1.4;3.6-dianhydro-L-iditol 2-nitrate.
55. 5-[2-Hydroxy-3-(2-cyanophenoxy)-propylamino]-5-desoxy-1.4;3.6-dianhydro-L-iditol 2-nitrate.
56. 5-[2-Hydroxy-3-(3-tolyloxy)-propylamino]-5-desoxy-1.4;3.6-dianhydro-L-iditol 2-nitrate.
57. 5-[2-Hydroxy-3-(3-trifluoromethylphenoxy)-propylamino]-5-desoxy-1.4;3.6-dianhydro-L-iditol 2-nitrate.
58. 5-[2-Hydroxy-3-(4-carbamoylmethylphenoxy)-propylamino]-5-desoxy-1.4;3.6-dianhydro-L-iditol 2-nitrate.
59. 5-[2-Hydroxy-3-(1-naphthyloxy)-propylamino]-5-desoxy-1.4;3.6-dianhydro-L-iditol 2-nitrate.
60. 5-[2-Hydroxy-3-(1-naphthyloxy)-propylamino]-5-desoxy-1.4;3.6-dianhydro-D-glucitol 2-nitrate.
61. 5-[2-Hydroxy-3-(1-oxo-1.2.3.4-tetrahydro-5-naphthyloxy)-propylamino]-5-desoxy-1.4;3.6-dianhydro-L-iditol 2-nitrate.
62. 5-[2-Hydroxy-3-(5.6.7.8-tetrahydro-1-naphthyloxy)-propylamino]-5-desoxy-1.4;3.6-dianhydro-L-iditol 2-nitrate.
63. 5-[3-(3-Trifluoromethylphenoxy)-propylamino]-5-desoxy-1.4;3.6-dianhydro-L-iditol 2-nitrate.
64. 5-[3-(4-Tolyloxy)-propylamino]-5-desoxy-1.4;3.6-dianhydro-L-iditol 2-nitrate.
65. 5-[3-(4-Fluorophenoxy)-propylamino]-5-desoxy-1.4;3.6-dianhydro-L-iditol 2-nitrate.
66. 5-[3-(1-Naphthyloxy)-propylamino]-5-desoxy-1.4;3.6-dianhydro-L-iditol 2-nitrate.
67. 5-[3-(4-Methoxyphenoxy)-propylamino]-5-desoxy-1.4;3.6-dianhydro-L-iditol 2-nitrate.
68. 5-[3-(3-Methoxyphenoxy)-propylamino]-5-desoxy-1.4;3.6-dianhydro-L-iditol 2-nitrate.
69. 5-[3-(2-Methoxyphenoxy)-propylamino]-5-desoxy-1.4;3.6-dianhydro-L-iditol 2-nitrate.
70. 5-[3-(2,6-Dimethoxyphenoxy)-propylamino]-5-desoxy-1.4;3.6-dianhydro-L-iditol 2-nitrate.
71. 5-[3-(3,5-Dimethoxyphenoxy)-propylamino]-5-desoxy-1.4;3.6-dianhydro-L-iditol 2-nitrate.
72. 5-[2,3-Dimethoxyphenoxy)-propylamino]-5-desoxy-1.4;3.6-dianhydro-L-iditol 2-nitrate.
73. 5-[3-(4-Chlorophenoxy)-propylamino]-5-desoxy-1.4;3.6-dianhydro-L-iditol 2-nitrate.
74. 5-[3-(2-Chlorophenoxy)-propylamino]-5-desoxy-1.4;3.6-dianhydro-L-iditol 2-nitrate.
75. 5-[3-(3-Chlorophenoxy)-propylamino]-5-desoxy-1.4;3.6-dianhydro-L-iditol 2-nitrate.
76. 5-[3-(3,4-Dichlorophenoxy)-propylamino]-5-desoxy-1.4;3.6-dianhydro-L-iditol 2-nitrate.
77. 5-[3-(2,4-Dichlorophenoxy)-propylamino]-5-desoxy-1.4;3.6-dianhydro-L-iditol 2-nitrate.
78. 5-[3-(4-Acetamidophenoxy)-propylamino]-5-desoxy-1.4;3.6-dianhydro-L-iditol 2-nitrate.
79. 5-[3-(3-Dimethylaminophenoxy)-propylamino]-5-desoxy-1.4;3.6-dianhydro-L-iditol 2-nitrate.
80. 5-[3-(4-Chlorophenyl)-propylamino]-5-desoxy-1.4;3.6-dianhydro-L-iditol 2-nitrate.

81. 5-[4-(4-Chlorophenyl)-butylamino]-5-desoxy-1.4;3.6-dianhydro-L-iditol 2-nitrate.

82. 5-Nicotinoylamino-5-desoxy-1.4;3.6-dianhydro-D-mannitol 2-nitrate.

83. 5-N-Methyl-N-nicotinoylamino-5-desoxy-1.4;3.6-dianhydro-L-iditol 2-nitrate.

84. A pharmaceutical composition comprising a pharmaceutically effective amount of the aminodesoxy-1.4;3.6-dianhydrohexitol nitrate of claim 1 and conventional carriers and additions therefore.

85. A method for the treatment of coronary disease in humans comprising administering a pharmaceutically effective amount of the composition of claim 84.

* * * * *